US012667276B1

(12) United States Patent
Geraghty et al.

(10) Patent No.: US 12,667,276 B1
(45) Date of Patent: Jun. 30, 2026

(54) MEDICAL DEVICES AND METHODS OF USE

(71) Applicant: MONITORING FOR LIFE, INC., Bradenton, FL (US)

(72) Inventors: Scott P. Geraghty, Peabody, MA (US); Tyler J. Harrington, Westford, MA (US)

(73) Assignee: Monitoring For Life, Inc., Bradenton, FL (US)

( * ) Notice: Subject to any disclaimer, the term of this patent is extended or adjusted under 35 U.S.C. 154(b) by 0 days.

(21) Appl. No.: 19/049,932

(22) Filed: Feb. 10, 2025

Related U.S. Application Data

(60) Provisional application No. 63/658,802, filed on Jun. 11, 2024.

(51) Int. Cl.
 *A61M 16/08* (2006.01)
 *A61B 5/00* (2006.01)
 (Continued)

(52) U.S. Cl.
 CPC .............. *A61B 5/097* (2013.01); *A61B 5/082* (2013.01); *A61M 16/085* (2014.02); *A61M 16/14* (2013.01); *A61M 2205/0216* (2013.01)

(58) Field of Classification Search
 CPC ............ A61B 1/00045; A61B 1/00082; A61B 1/00124; A61B 1/00154; A61B 1/0017;
 (Continued)

(56) References Cited

U.S. PATENT DOCUMENTS

| | | | |
|---|---|---|---|
| 2,797,683 A | 7/1957 | Aiken | |
| 3,856,051 A | 12/1974 | Bain | |

(Continued)

FOREIGN PATENT DOCUMENTS

| | | | |
|---|---|---|---|
| WO | 2014004762 A1 | 1/2014 | |
| WO | 2015109229 A1 | 7/2015 | |
| WO | 2016172555 A1 | 10/2016 | |

OTHER PUBLICATIONS

International Search Report and Written Opinion from corresponding PCT Appln. No. PCT/US2015/011818, dated May 6, 2015. 7 pages.

(Continued)

*Primary Examiner* — Annette Dixon
(74) *Attorney, Agent, or Firm* — Secant IP, PLLC; Michael J. Gallagher

(57) ABSTRACT

A medical device, comprising a breathing tube apparatus having a proximal end and a distal end, the breathing tube apparatus further comprising a ventilation tube; a connection fitting body connected to the ventilation tube; a ventilation passageway, wherein the ventilation passageway is disposed in the connection fitting body and disposed in the ventilation tube; an exhaled gas(es) sampling port; wherein the exhaled gas(es) sampling port comprises an elastically deformable tube having a tube passageway and at least one sample inlet to the tube passageway, the tube passageway in fluid communication with the ventilation passageway in the connection fitting body via the at least one sample inlet; wherein the elastically deformable tube extends from the connection fitting body into the ventilation passageway in the connection fitting body.

41 Claims, 25 Drawing Sheets

(51) Int. Cl.
  *A61B 5/08*         (2006.01)
  *A61B 5/097*        (2006.01)
  *A61M 16/14*        (2006.01)

(58) Field of Classification Search
  CPC ........... A61B 1/015; A61B 1/05; A61B 1/051;
    A61B 1/0607; A61B 1/0669; A61B
    1/0676; A61B 1/0684; A61B 1/07; A61B
    1/126; A61B 1/127; A61B 1/233; A61B
    1/267; A61B 1/2676; A61B 17/12022;
    A61B 17/12109; A61B 17/1214; A61B
    17/12145; A61B 17/12172; A61B 5/0075;
    A61B 5/0084; A61B 5/0205; A61B
    5/029; A61B 5/08; A61B 5/082; A61B
    5/0836; A61B 5/097; A61B 5/1459; A61B
    5/4821; A61M 1/7413; A61M 11/00;
    A61M 16/0078; A61M 16/009; A61M
    16/0096; A61M 16/04; A61M 16/0404;
    A61M 16/0422; A61M 16/0425; A61M
    16/0434; A61M 16/0438; A61M 16/0443;
    A61M 16/0445; A61M 16/0459; A61M
    16/0463; A61M 16/0479; A61M 16/0484;
    A61M 16/0486; A61M 16/0488; A61M
    16/049; A61M 16/0493; A61M 16/0495;
    A61M 16/06; A61M 16/08; A61M
    16/0816; A61M 16/0825; A61M 16/0833;
    A61M 16/085; A61M 16/0858; A61M
    16/105; A61M 16/1065; A61M 16/209;
    A61M 2016/0027; A61M 2016/0413;
    A61M 2025/018; A61M 2202/203; A61M
    2205/02; A61M 2205/0238; A61M
    2205/051; A61M 2205/3306; A61M
    2205/3313; A61M 2205/3331; A61M
    2205/3553; A61M 2205/3569; A61M
    2205/3592; A61M 2205/50; A61M
    2205/502; A61M 2205/587; A61M
    2205/7536; A61M 2205/8206; A61M
    2230/205; A61M 2230/432; A61M
    2230/435; A61N 2005/0604; A61N
    2005/0609; A61N 2005/0651; A61N
    2005/0661; A61N 5/0601; A61N 5/0603;
    A61N 5/0624; B29C 2045/1724; B29C
    45/1704; F16L 11/20; F16L 11/22; Y10S
    128/26; Y10S 128/911; Y10S 128/912;
    Y10T 29/49826
  See application file for complete search history.

(56)                References Cited

U.S. PATENT DOCUMENTS

| | | | |
|---|---|---|---|
| 4,072,146 A | | 2/1978 | Howes |
| 4,326,569 A | | 4/1982 | Vaillancourt |
| 4,334,534 A | | 6/1982 | Ozaki |
| 4,351,328 A | * | 9/1982 | Bodai ............... A61M 16/0463 |
| | | | 128/207.14 |
| 4,409,977 A | | 10/1983 | Bisera et al. |
| 4,456,014 A | | 6/1984 | Buck et al. |
| 4,488,548 A | | 12/1984 | Agdanowski |
| 4,558,709 A | | 12/1985 | Aida et al. |
| 4,567,882 A | | 2/1986 | Heller |
| 4,669,463 A | | 6/1987 | Mcconnell |
| 4,677,987 A | | 7/1987 | Choksi |
| 4,834,087 A | | 5/1989 | Coleman et al. |
| 4,850,371 A | | 7/1989 | Broadhurst et al. |
| 4,919,132 A | | 4/1990 | Miser |
| 4,945,918 A | | 8/1990 | Abernathy |
| 5,000,175 A | | 3/1991 | Pue |

| | | | |
|---|---|---|---|
| 5,060,646 A | * | 10/1991 | Page ................. A61M 16/0463 |
| | | | 128/207.14 |
| 5,062,420 A | | 11/1991 | Levine |
| 5,193,544 A | | 3/1993 | Jaffe |
| 5,357,946 A | | 10/1994 | Kee et al. |
| 5,421,821 A | | 6/1995 | Janicki et al. |
| 5,657,750 A | | 8/1997 | Colman et al. |
| 5,855,203 A | | 1/1999 | Matter |
| 5,857,461 A | | 1/1999 | Levitsky et al. |
| 6,422,240 B1 | | 7/2002 | Levitsky et al. |
| 6,437,316 B1 | | 8/2002 | Colman et al. |
| 6,568,388 B2 | | 5/2003 | Christopher |
| 6,843,769 B1 | | 1/2005 | Gandarias |
| 6,926,005 B1 | | 8/2005 | Colman et al. |
| 7,036,501 B2 | * | 5/2006 | Wall .................... A61B 5/0836 |
| | | | 128/207.14 |
| 7,503,328 B2 | | 3/2009 | Kolobow et al. |
| 8,074,649 B2 | | 12/2011 | Dhuper et al. |
| 8,323,207 B2 | | 12/2012 | Popov et al. |
| 10,010,690 B1 | | 7/2018 | Geraghty |
| 10,112,024 B2 | | 10/2018 | Geraghty et al. |
| 11,219,728 B2 | * | 1/2022 | Geraghty .......... A61M 16/0486 |
| 12,502,500 B2 | | 12/2025 | Geraghty |
| 2003/0078476 A1 | | 4/2003 | Hill |
| 2003/0199807 A1 | | 10/2003 | Dent et al. |
| 2004/0120156 A1 | | 6/2004 | Ryan |
| 2004/0138531 A1 | | 7/2004 | Bonner et al. |
| 2004/0210114 A1 | | 10/2004 | Simon |
| 2004/0215061 A1 | | 10/2004 | Kimmel et al. |
| 2005/0039754 A1 | | 2/2005 | Simon |
| 2005/0279354 A1 | | 12/2005 | Deutsch et al. |
| 2007/0088317 A1 | | 4/2007 | Hyde |
| 2007/0129603 A1 | | 6/2007 | Hirsh |
| 2007/0221229 A1 | | 9/2007 | Rahaghi et al. |
| 2007/0277828 A1 | | 12/2007 | Ho et al. |
| 2010/0137732 A1 | | 6/2010 | Haveri |
| 2010/0168599 A1 | | 7/2010 | Esposito et al. |
| 2010/0229863 A1 | | 9/2010 | Enk |
| 2010/0249639 A1 | | 9/2010 | Bhatt |
| 2010/0280362 A1 | | 11/2010 | Li et al. |
| 2011/0178419 A1 | | 7/2011 | Wood et al. |
| 2011/0300505 A1 | | 12/2011 | Jessop et al. |
| 2012/0002427 A1 | | 1/2012 | Moon et al. |
| 2012/0101343 A1 | | 4/2012 | Duffy et al. |
| 2012/0172664 A1 | | 7/2012 | Hayman et al. |
| 2012/0321509 A1 | | 12/2012 | Bak |
| 2013/0053636 A1 | | 2/2013 | Hayman et al. |
| 2013/0092171 A1 | | 4/2013 | Sederstrom et al. |
| 2013/0303849 A1 | | 11/2013 | Allyn et al. |
| 2014/0180252 A1 | | 6/2014 | Gabriel |
| 2015/0190649 A1 | | 7/2015 | Gelfand et al. |
| 2016/0296719 A1 | | 10/2016 | Geraghty et al. |
| 2019/0060595 A1 | | 2/2019 | Geraghty et al. |
| 2022/0126044 A1 | | 4/2022 | Geraghty |

OTHER PUBLICATIONS

International Search Report and Written Opinion from corresponding PCT Appln. No. PCT/US2016/028949, dated Jul. 26, 2016. 10 pages.
Office Action dated Nov. 2, 2016, issued in U.S. Appl. No. 15/136,587, 17 pages.
Office Action mailed Dec. 19, 2017, issued in U.S. Appl. No. 15/136,587, 29 pages.
Office Action dated Aug. 2, 2016, issued in U.S. Appl. No. 14/209,706, 11 pages.
Office Action dated Feb. 24, 2021, issued in U.S. Appl. No. 16/173,739, 28 pages.
Office Action dated Mar. 23, 2022, issued in U.S. Appl. No. 16/021,943, 22 pages.
Office Action dated May 6, 2024, issued in U.S. Appl. No. 16/021,943, 15 pages.
Office Action dated Jan. 12, 2023, issued in U.S. Appl. No. 16/021,943, 11 pages.
Office Action dated Aug. 17, 2023, issued in U.S. Appl. No. 16/021,943, 14 pages.

(56) References Cited

OTHER PUBLICATIONS

Office Action dated Dec. 12, 2024, issued in U.S. Appl. No. 17/572,158, 14 pages.
Non-Final Office Action of U.S. Appl. No. 19/428,901; Mail date Apr. 3, 2026; 55 pages.

* cited by examiner

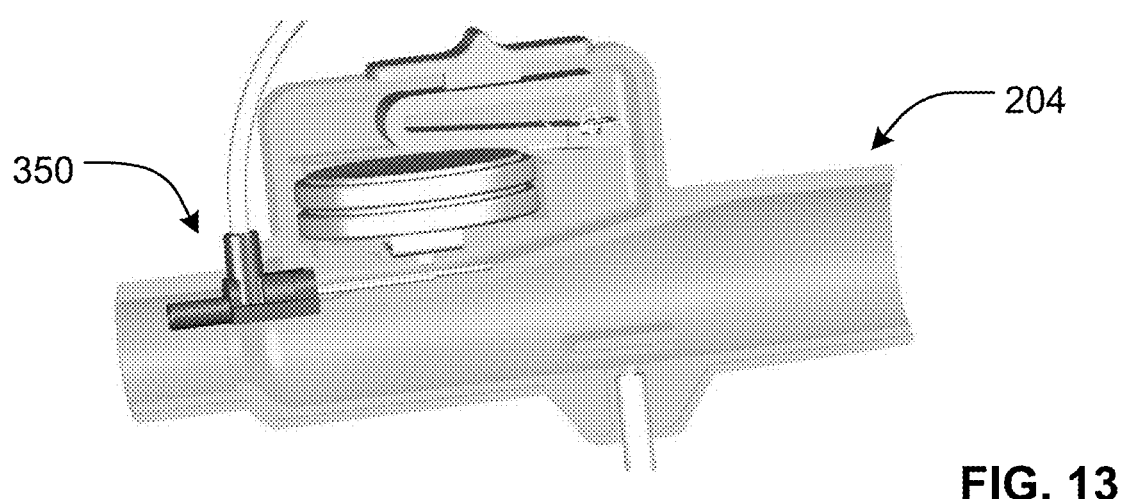
FIG. 13
FIG. 14
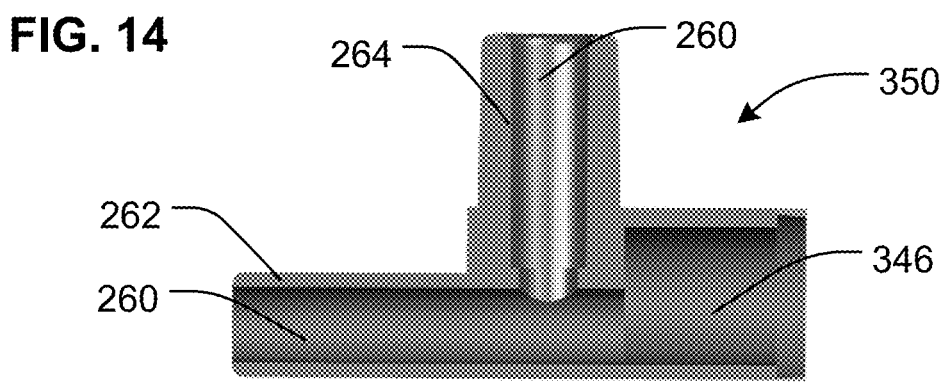
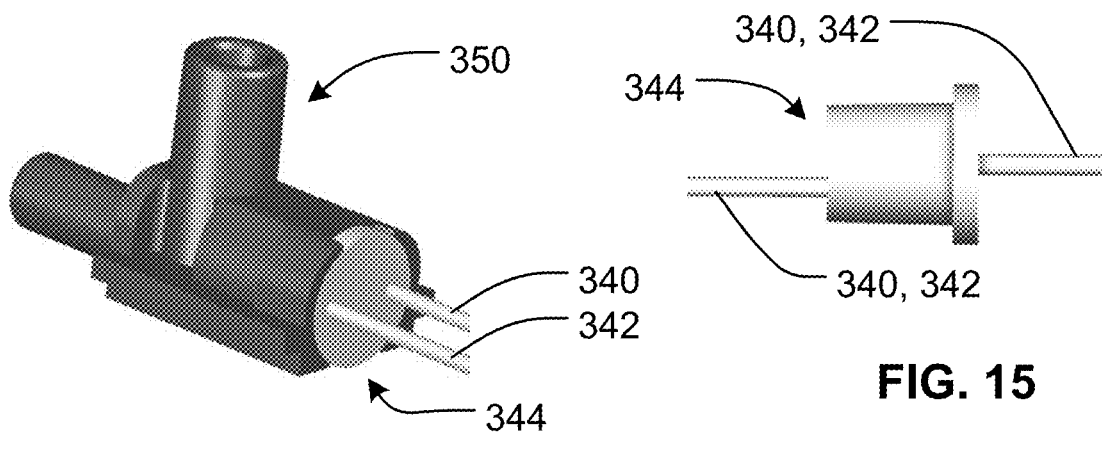
FIG. 15
FIG. 16

FIG. 27
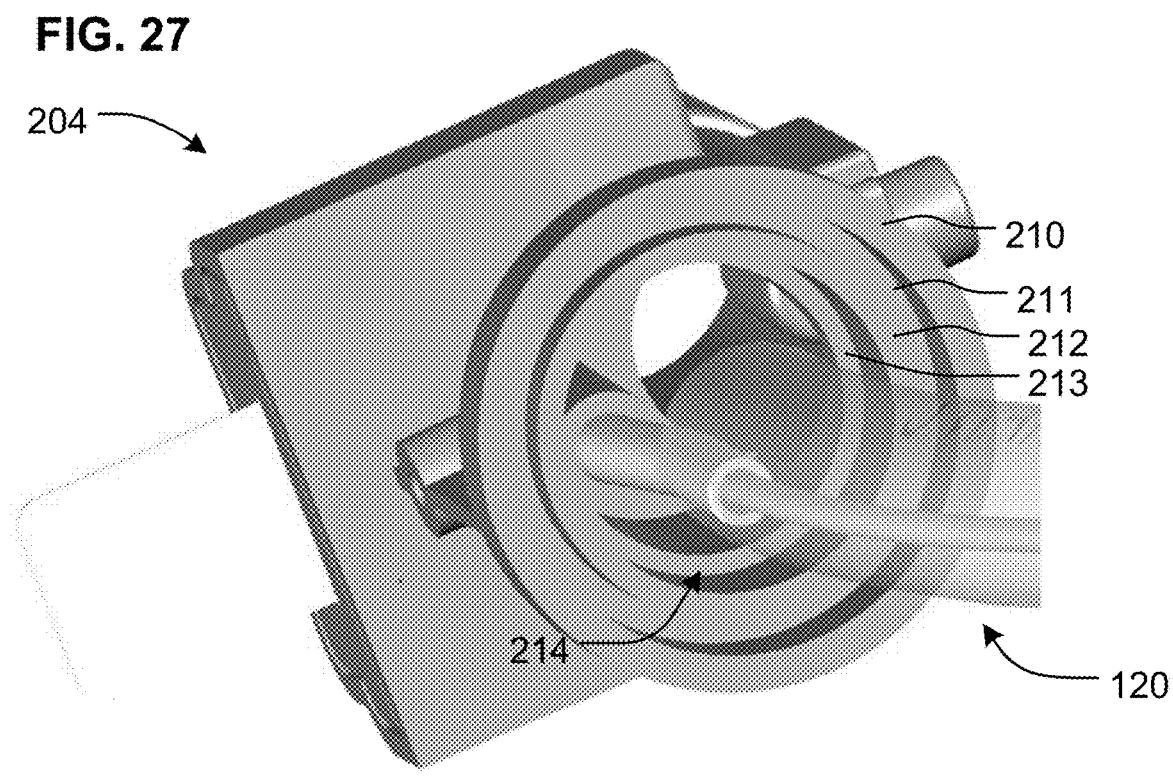
FIG. 28     FIG. 29
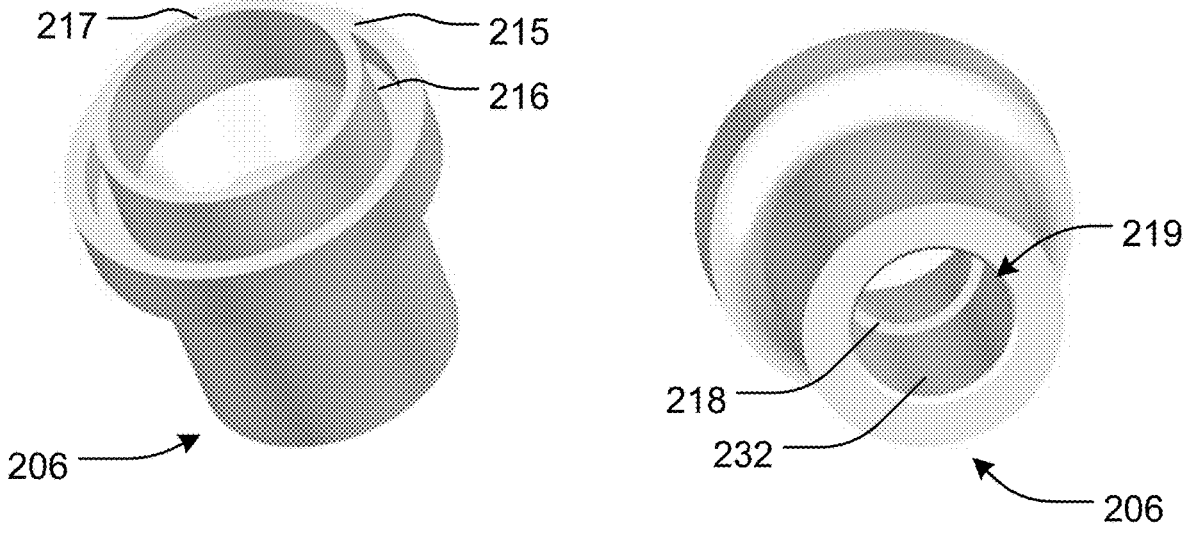

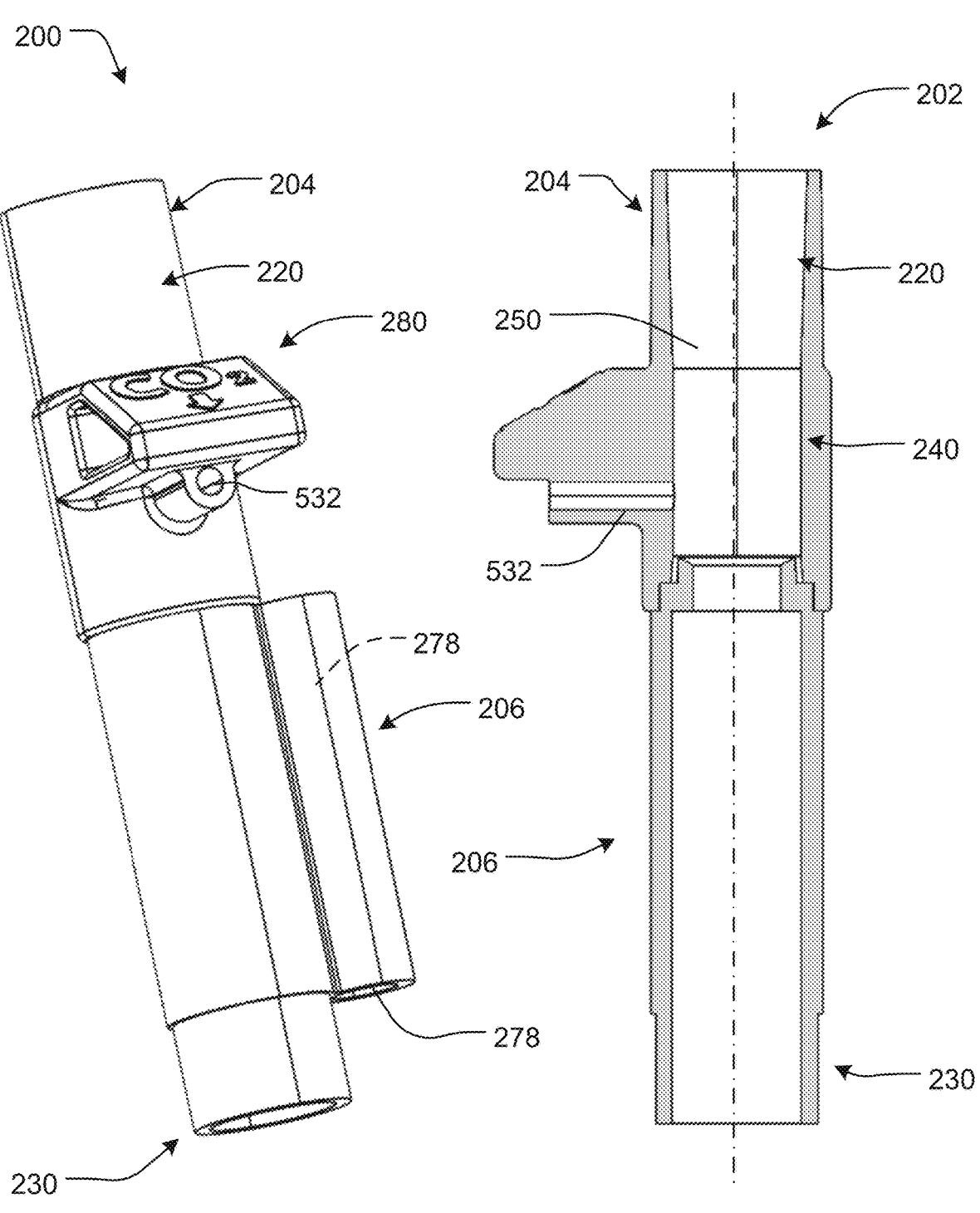
FIG. 53                                    FIG. 54

MEDICAL DEVICES AND METHODS OF USE

CROSS-REFERENCE TO RELATED APPLICATIONS

This application claims the benefit of the filing date of U.S. provisional application Ser. No. 63/658,802, filed Jun. 11, 2024, which is incorporated by reference.

FIELD

This disclosure relates generally to the field of medical devices, and more specifically to a medical tube apparatus, particularly a ventilation (breathing) tube apparatus, such as an endotracheal tube apparatus, to be used on a human body.

BACKGROUND

Artificial respiration involves assisting or stimulating a person's natural respiration, a metabolic process referring to an exchange of gases within the body by pulmonary ventilation, external respiration and internal respiration. Pulmonary ventilation is achieved through insufflation (e.g. manual or automated) of a person's lungs by causing air or oxygen to flow in and out of a person's lungs, generally when natural breathing has stopped or is otherwise inadequate.

One method of pulmonary ventilation involves intubation, or entubation, which pertains to the insertion of a tube generally into an external orifice of the body. One particular method of intubation is tracheal intubation, in which a flexible plastic tube is inserted into the trachea (windpipe) of a person to provide or maintain an open airway, and to serve as a conduit through which to administer certain drugs via a drug delivery port. Tracheal intubation is often performed in critically injured or anesthetized patients to facilitate pulmonary ventilation and to prevent the possibility of asphyxiation or airway obstruction. Tracheal intubation is most often orotracheal, in which an endotracheal tube is passed through the mouth and voice box (vocal cords) of a person and into the trachea.

During an endotracheal intubation, the person's mouth is opened and the endotracheal tube is inserted down the throat. To better ensure the endotracheal tube is properly positioned, a laryngoscope may be used to bring the vocal cords and larynx into view prior to inserting the endotracheal tube. The tube may then be inserted in the trachea through the vocal cords to the point that an inflation cuff surrounding a distal end portion of the tube rests just below the vocal cords. Finally, after the inflation cuff is inflated to inhibit leakage, a bag valve mask in fluid communication with the ventilation passageway of the tube is squeezed to pass air and/or oxygen though the ventilation tube of the tube to the lungs. A stethoscope may then be used by medical personnel to listen for breathing sounds to ensure proper placement of the tube.

Often endotracheal intubation must be performed away from a clinic and in the field, particularly during a trauma and other emergency situations. Unfortunately, under such adverse conditions, it may not be possible to use a laryngoscope or a stethoscope to ensure proper placement of the endotracheal tube in the trachea, in which case the endotracheal tube may enter the esophagus.

With endotracheal tubes in the art, often the drug delivery port and the cuff inflation port include tubing which is spliced from the outside into a sidewall of the endotracheal tube. Unfortunately, because the spliced tubing is located between the endotracheal tube and the person's mouth during use, the tubing of the ports may be damaged during use, such as being severed by the person's teeth in response to a seizure. Also, the spliced ports may become compressed between the person's mouth and the endotracheal tube, and not function as intended.

Also in the art, a sampling port may be provided as part of a separate adapter, to be located upstream of the proximal end connector of the endotracheal tube, to sample gases of the person being intubated. More particularly, the sampling port may be a carbon dioxide sampling port which is connectable to a carbon dioxide analyzer/monitor (e.g. a capnograph).

SUMMARY

The present disclosure provides medical devices comprising a ventilation tube apparatus, which may particularly be an endotracheal tube apparatus, of a medical (respiratory) system. The ventilation tube apparatus, such as an endotracheal tube apparatus, may incorporate one or more ports which are less susceptible to damage by a patient during use of the ventilation (e.g. endotracheal) tube by virtue of the one or more ports not being spliced into the sidewall of the ventilation tube. The ventilation tube apparatus, such as an endotracheal tube apparatus, may also incorporate a lighting apparatus to provide visual aid during intubation to better ensure proper placement of the ventilation tube, such as in the trachea.

In addition to, or alternatively to, the foregoing benefits, the medical devices comprising a ventilation tube apparatus, and more particularly an endotracheal tube apparatus, of a medical (respiratory) system according to the present disclosure, may reduce stack-up of multiple components and associated air leaks occurring there between by combining multiple features into a hub connection fitting of the ventilation tube apparatus.

In addition to, or alternatively to, the foregoing benefits, the medical devices comprising a ventilation tube apparatus, and more particularly an endotracheal tube apparatus, of a medical (respiratory) system according to the present disclosure, may have exhaled gas(es) sampling port which comprises an elastically deformable tube having a tube passageway in fluid communication with a ventilation passageway and the elastically deformable tube extends into the ventilation passageway.

In at least one embodiment, a medical device may comprise a breathing tube apparatus having a proximal end and a distal end, and further comprising a ventilation tube having a proximal end and a distal end, wherein the ventilation tube is configured to be inserted into an airway of a human body; a connection fitting body connected to the ventilation tube, wherein the connection fitting body is disposed adjacent the proximal end of the ventilation tube proximal to the proximal end of the ventilation tube, and wherein the connection fitting body provides the proximal end of the breathing tube apparatus; a ventilation passageway, wherein the ventilation passageway is disposed in the connection fitting body and disposed in the ventilation tube; an exhaled gas(es) sampling port, wherein the exhaled gas(es) sampling port is configured to be connected to an exhaled gas(es) sampling device configured to detect a presence of carbon dioxide in an exhaled gas(es) sample; wherein the exhaled gas(es) sampling port comprises an elastically deformable tube having a tube passageway and at least one sample inlet to the tube passageway, the tube passageway in fluid communication with the ventilation passageway in the connection fitting body via the at least one sample inlet; wherein the elastically deformable tube extends from the connection fitting body into the ventilation passageway in the connection fitting body.

In at least one embodiment, a medical device may comprise wherein the elastically deformable tube extends from the connection fitting body into the ventilation passageway in the connection fitting body at a distance of at least 0.5 mm; and/or wherein the at least one sample inlet extends from the connection fitting body into the ventilation passageway in the connection fitting body at a distance of at least 0.5 mm.

In at least one embodiment, a medical device may comprise wherein the elastically deformable tube is sufficiently elastically deformable to elastically deform when contacted by the elongated medical instrument in the ventilation passageway to provide clearance for the elongated medical instrument to pass by the elastically deformable tube.

In at least one embodiment, a medical device may comprise the elongated medical instrument, wherein the elongated medical instrument is a guide, an introducer, a bougie, a stylet or a catheter.

In at least one embodiment, a medical device may comprise wherein the elastically deformable tube is elastically deformable towards at least one of the distal end of the breathing tube apparatus, the proximal end of the breathing tube apparatus, or a sidewall which forms the ventilation passageway in the connection fitting body.

In at least one embodiment, a medical device may comprise wherein the elastically deformable tube is moveable from a first position in the ventilation passageway in the connection fitting body to a second position in the ventilation passageway in the connection fitting body by elastic deformation of the tube; and wherein the elastically deformable tube is moveable from the second position in the ventilation passageway in the connection fitting body towards the first position in the ventilation passageway in the connection fitting body by elastic recovery of the tube.

In at least one embodiment, a medical device may comprise wherein the elastically deformable tube is elastically deformable in the ventilation passageway in the connection fitting body at a deformation distance; and wherein the deformation distance is greater than or equal to 0.5 mm.

In at least one embodiment, a medical device may comprise wherein the elastically deformable tube is elastically deformable in the ventilation passageway in the connection fitting body at a deformation angle; and wherein the deformation angle is greater than or equal to 5 degrees.

In at least one embodiment, a medical device may comprise wherein the ventilation passageway in the connection fitting body has a longitudinal axis; wherein the ventilation passageway in the connection fitting body has a total cross-sectional area transverse to the longitudinal axis; wherein the total cross-sectional area has an inner cross-sectional area region and an outer cross-sectional area region; wherein the outer cross-sectional area region forms an enclosed ring around the inner cross-sectional area region; wherein the inner cross-sectional area region is in a range of 5% to 95% of the total cross-sectional area; wherein the at least one sample inlet is disposed in the inner cross-sectional area region.

In at least one embodiment, a medical device may comprise wherein the ventilation passageway in the connection fitting body has a longitudinal axis; wherein the ventilation passageway in the connection fitting body has a cross-sectional dimension perpendicular to the longitudinal axis; and wherein the tube and/or the sample inlet extends into the ventilation passageway in the connection fitting body at a distance in a range of 5% to 95% of the cross-sectional dimension of the ventilation passageway in the connection fitting body.

In at least one embodiment, a medical device may comprise wherein the elastically deformable tube is extruded tubing.

In at least one embodiment, a medical device may comprise wherein the elastically deformable tube has an outer diameter in a range of 0.50 mm to 3 mm; and/or wherein the tube passageway has a diameter of in a range of 0.25 mm to 2 mm.

In at least one embodiment, a medical device may comprise wherein the elastically deformable tube is formed of a thermoplastic polymer composition.

In at least one embodiment, a medical device may comprise wherein the elastically deformable tube has a Shore A durometer hardness, as measured by ASTM D2240-15 (2021), in a range of 40-95 Shore A durometer hardness.

In at least one embodiment, a medical device may comprise wherein the ventilation passageway in the connection fitting body has a longitudinal axis; wherein the elastically deformable tube has a longitudinal axis; and wherein the longitudinal axis of the elastically deformable tube is substantially transverse to the longitudinal axis of the ventilation passageway in the connection fitting body.

In at least one embodiment, a medical device may comprise wherein the longitudinal axis of the elastically deformable tube is perpendicular to the longitudinal axis of the ventilation passageway in the connection fitting body.

In at least one embodiment, a medical device may comprise wherein the elastically deformable tube and the connection fitting body are connected as to form a hermetic seal.

In at least one embodiment, a medical device may comprise wherein the elastically deformable tube and the connection fitting body are at least one of interference fit, bonded or welded together.

In at least one embodiment, a medical device may comprise wherein the elastically deformable tube has a circular, annular wall which surrounds the tube passageway; and wherein the circular, annular wall of the elastically deformable tube extends through a bore in the connection fitting body.

In at least one embodiment, a medical device may comprise wherein the breathing tube apparatus is an endotracheal breathing tube apparatus, an extraglottic breathing tube apparatus or a supraglottic breathing tube apparatus.

In at least one embodiment, a medical treatment method may comprise obtaining a breathing tube apparatus having a proximal end and a distal end, and further comprising a ventilation tube having a proximal end and a distal end, wherein the ventilation tube is configured to be inserted into an airway of a human body; a connection fitting body connected to the ventilation tube, wherein the connection fitting body is disposed adjacent the proximal end of the ventilation tube proximal to the proximal end of the ventilation tube, and wherein the connection fitting body provides the proximal end of the breathing tube apparatus; a ventilation passageway, wherein the ventilation passageway is disposed in the connection fitting body and disposed in the ventilation tube; an exhaled gas(es) sampling port, wherein the exhaled gas(es) sampling port is configured to be connected to an exhaled gas(es) sampling device configured to detect a presence of carbon dioxide in an exhaled gas(es) sample; wherein the exhaled gas(es) sampling port comprises an elastically deformable tube having a tube passageway and at least one sample inlet to the tube passageway, the tube passageway in fluid communication with the ventilation passageway in the connection fitting body via the at least one sample inlet; wherein the elastically deformable tube extends from the connection fitting body into the ventilation passageway in the connection fitting body; inserting an elongated medical instrument into the ventilation passageway in the connection fitting body; contacting the elastically deformable tube with the elongated medical instrument; and moving the elastically deformable tube with the elongated medical instrument when the elongated medical instrument is disposed in the ventilation passageway of the connection fitting body.

In at least one embodiment, the medical treatment method may comprise wherein, during moving of the elastically deformable tube with the elongated medical instrument, the elastically deformable tube moves from a first position to a second position; and wherein, as the elastically deformable tube moves from the first position to the second position, the elastically deformable tube undergoes elastic deformation.

In at least one embodiment, the medical treatment method may comprise moving the elastically deformable tube from the second position towards the first position.

In at least one embodiment, the medical treatment method may comprise wherein, as the elastically deformable tube moves from the second position towards the first position, the elastically deformable tube undergoes elastic recovery.

In at least one embodiment, the medical treatment method may comprise wherein moving the elastically deformable tube from the second position towards the first position occurs during and/or after withdrawing the elongated medical instrument from the ventilation tube apparatus.

In at least one embodiment, the medical treatment method may comprise wherein moving the elastically deformable tube from the second position towards the first position occurs upon and/or after removing the elongated medical instrument from contact with the elastically deformable tube.

In at least one embodiment, the medical treatment method may comprise wherein, as the elastically deformable tube moves, the elastically deformable tube moves laterally in the ventilation passageway.

In at least one embodiment, the medical treatment method may comprise wherein, as the elastically deformable tube moves, the elastically deformable tube moves distally in the ventilation passageway.

In at least one embodiment, the medical treatment method may comprise wherein, as the elastically deformable tube moves, the elastically deformable tube moves proximally in the ventilation passageway.

FIGURES

The above-mentioned and other features of this disclosure, and the manner of attaining them, will become more apparent and better understood by reference to the following description of embodiments described herein taken in conjunction with the accompanying drawings, wherein:

FIG. 13 is a perspective view of the hub connection fitting of FIG. 10 with a cuff inflation port fitment of the hub connection fitting body with another portion of the hub connection fitting body shown transparent;

FIG. 14 is a cross-sectional view of the cuff inflation port fitment of FIG. 13 of the hub connection fitting body;

FIG. 15 is a side view of a plug which is configured to be assembled with the cuff inflation port fitment of FIG. 14;

FIG. 16 is a perspective view of the cuff inflation port fitment of FIG. 14 and the plug of FIG. 15 assembled;

FIG. 27 is another close-up perspective view of the hub connection fitting of the ventilation tube apparatus of FIG.

7

Figures 1, 2:
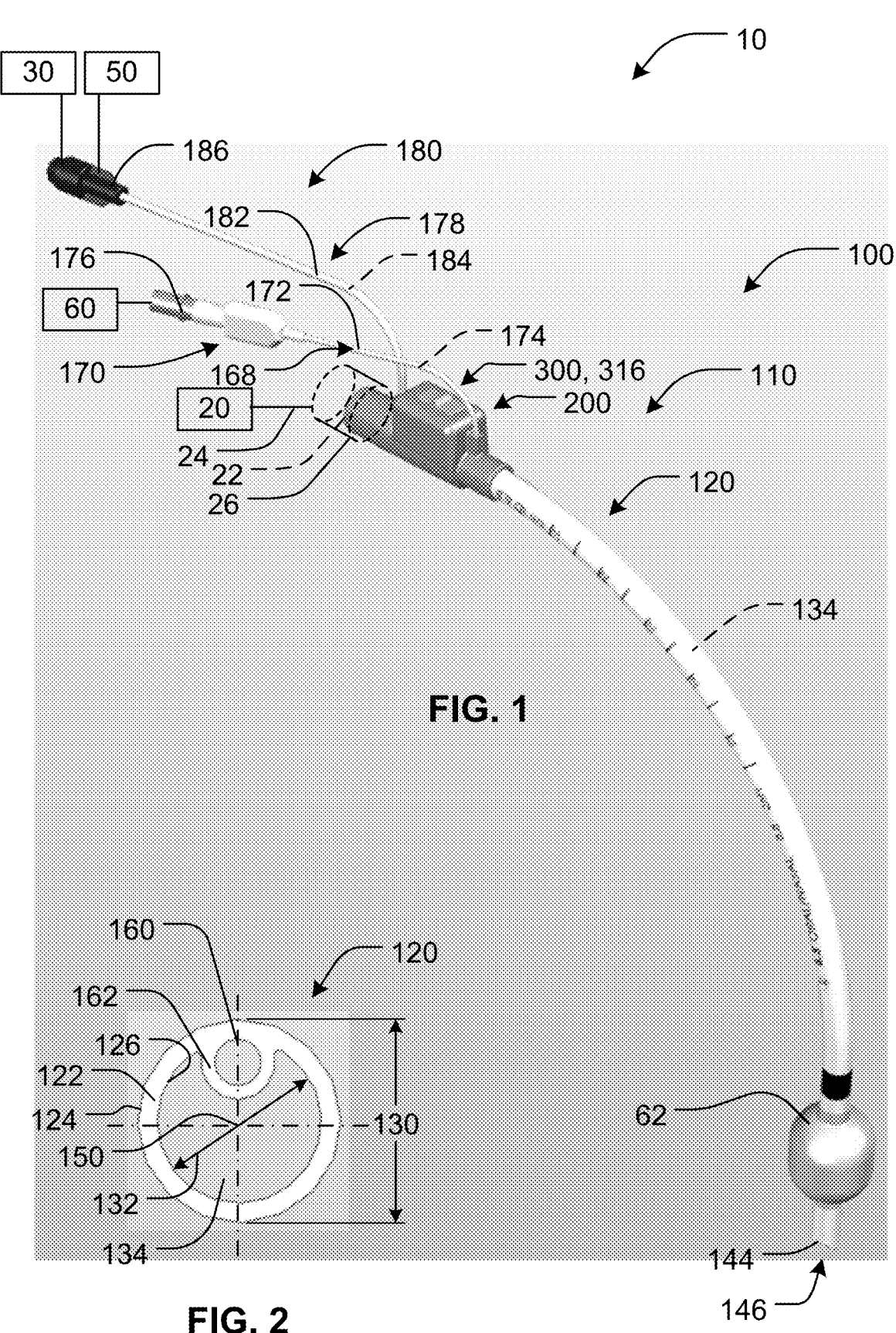
FIG. 1 is a perspective view of a medical system including a medical device comprising a ventilation (breathing) tube apparatus, and more particularly an endotracheal tube apparatus, according to the present disclosure.
FIG. 2 is an enlarged cross-sectional view of a ventilation (endotracheal) tube of the endotracheal tube apparatus of FIG. 1.
Figure 3:
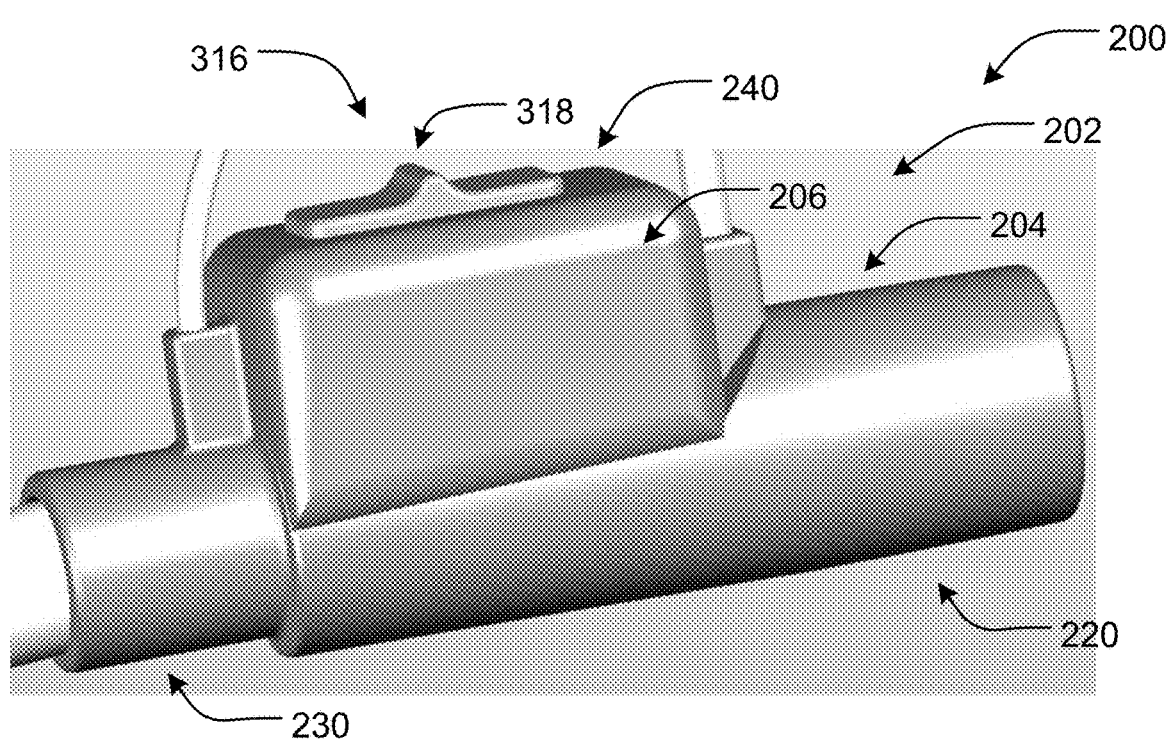
FIG. 3 is a close-up perspective view of a hub connection fitting of the ventilation tube apparatus of FIG. 1.
Figure 4:
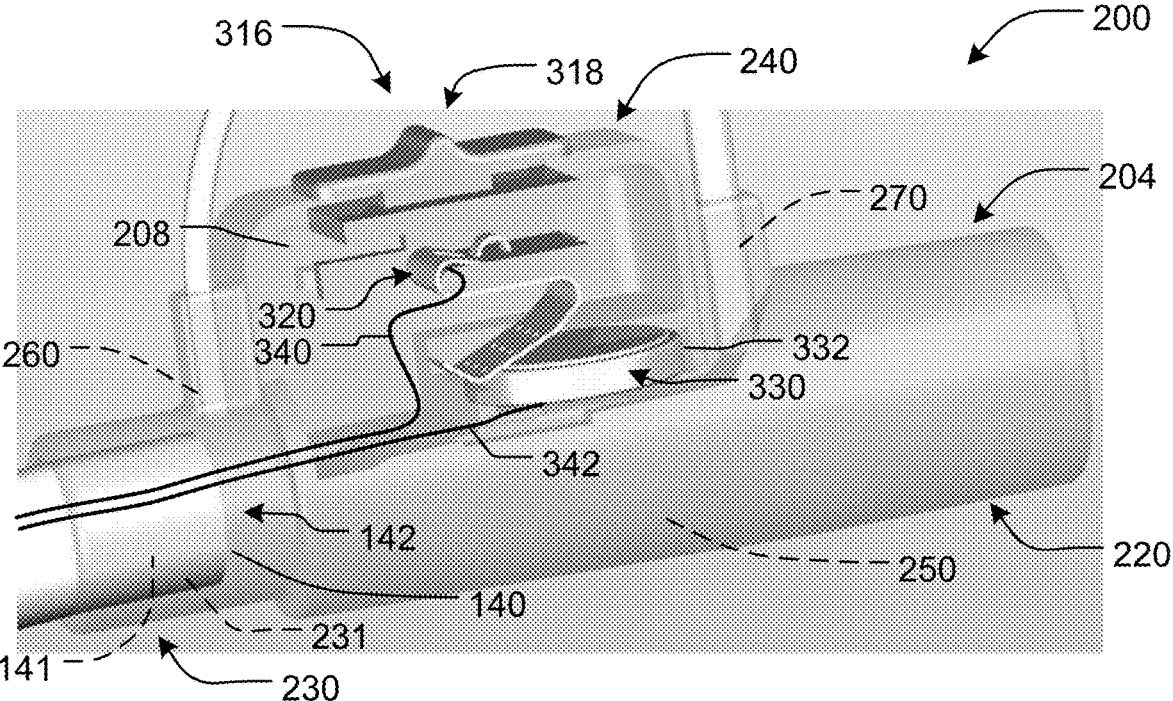
FIG. 4 is a close-up perspective view of the hub connection fitting of FIG. 3 with a portion of the hub connection fitting body shown transparent and another portion of the hub connection fitting body removed.
Figure 5:
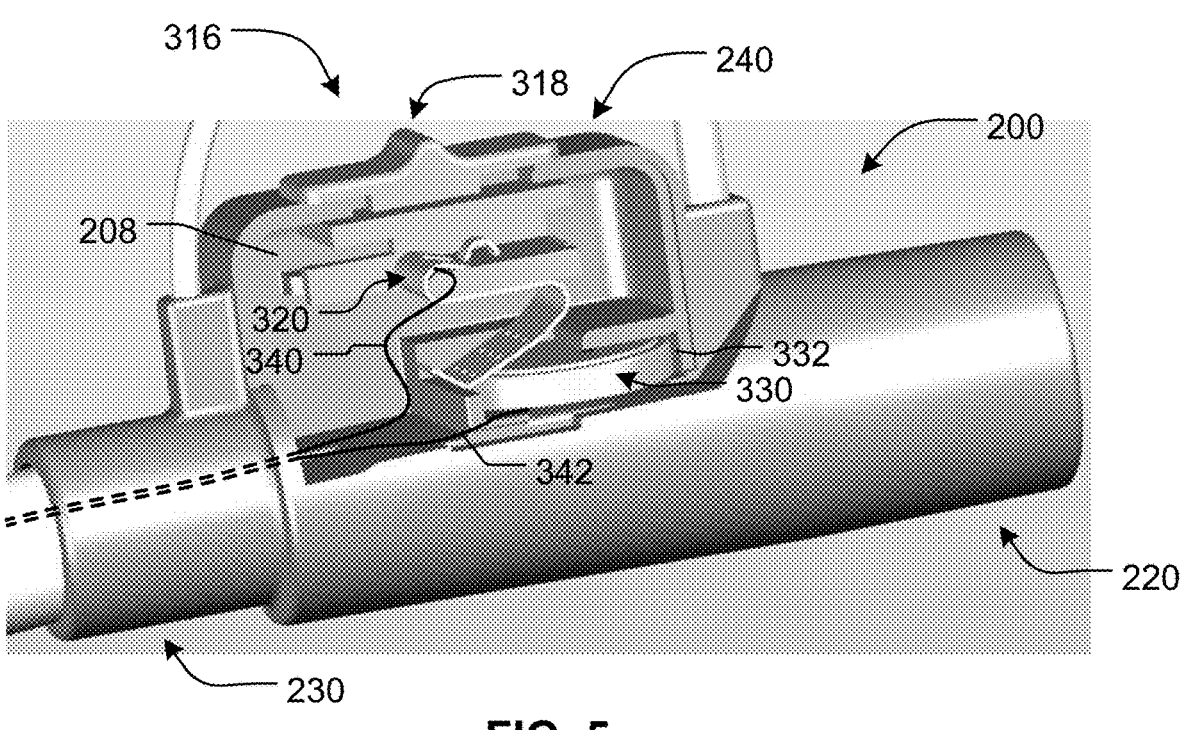
FIG. 5 is a close-up perspective view of the hub connection fitting of FIG. 3 with a portion of the hub connection fitting body removed and a light switch in a first (off) position.
Figure 6:
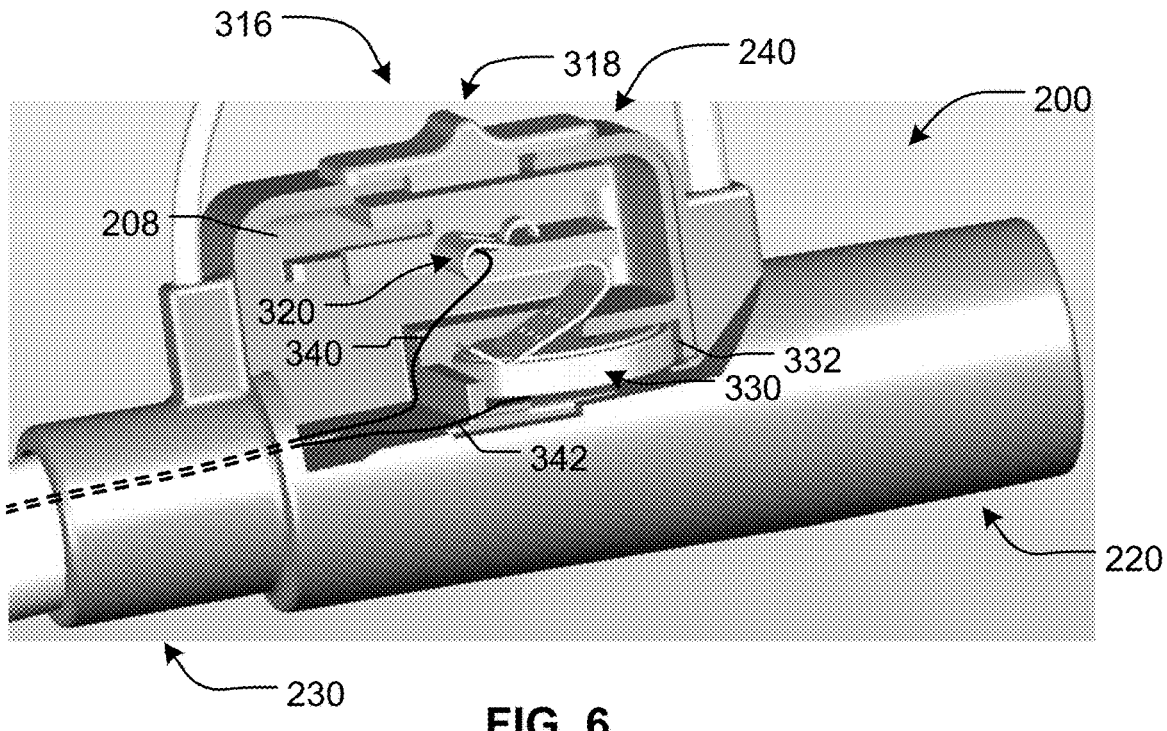
FIG. 6 is a close-up perspective view of the hub connection fitting of FIG. 3 with a portion of the hub connection fitting body removed and the light switch in a second (on) position.
Figure 7:
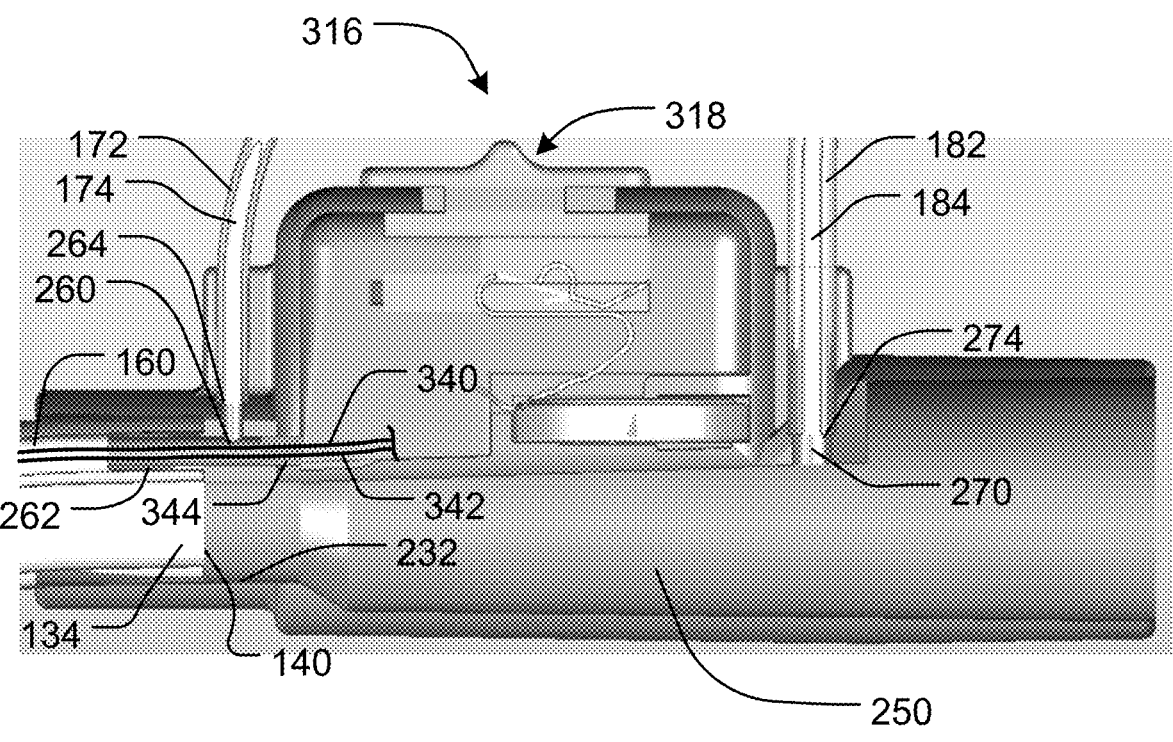
FIG. 7 is a close-up cross-sectional side view of the hub connection fitting of FIG. 3.
Figure 8:
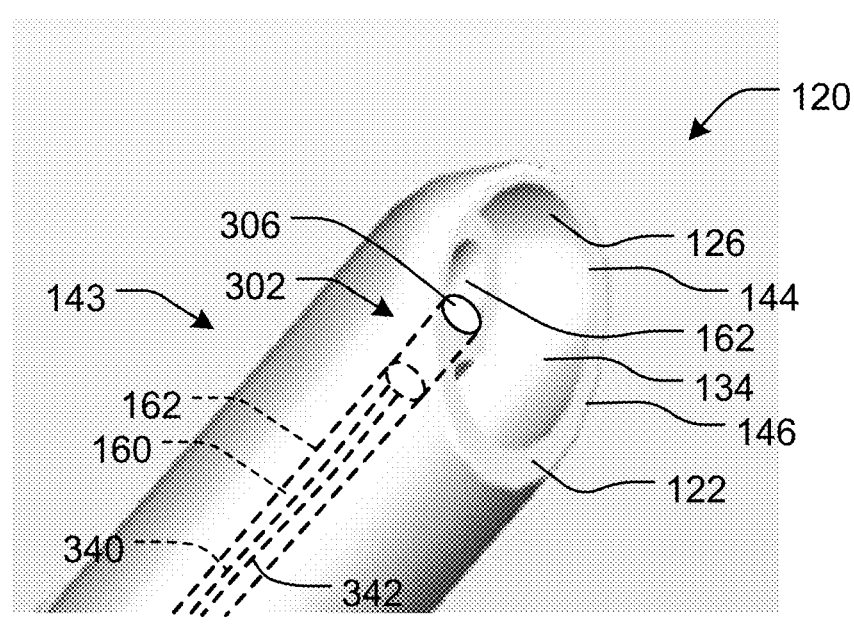
FIG. 8 is a close-up perspective view of a distal region the ventilation tube of the ventilation tube apparatus of FIG. 1.
Figure 9:
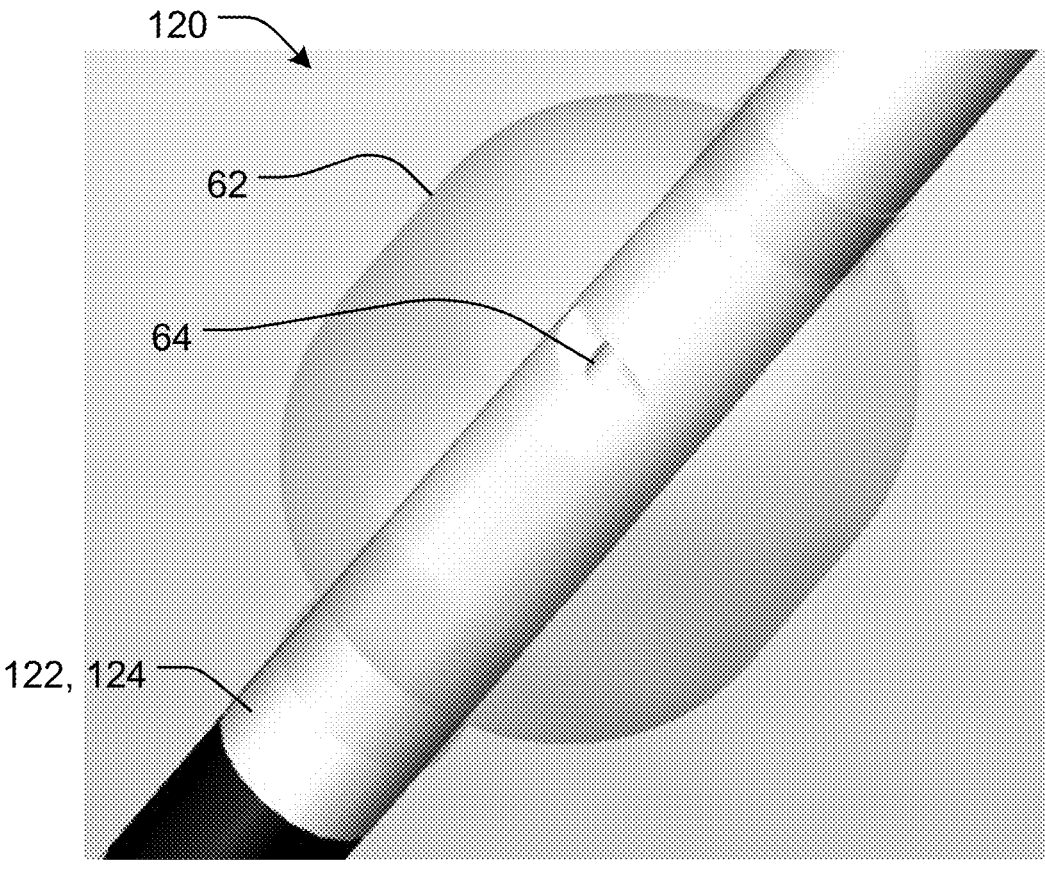
FIG. 9 is a close-up perspective view of the inflation cuff of the ventilation tube of the ventilation tube apparatus of FIG. 1.
Figure 10:
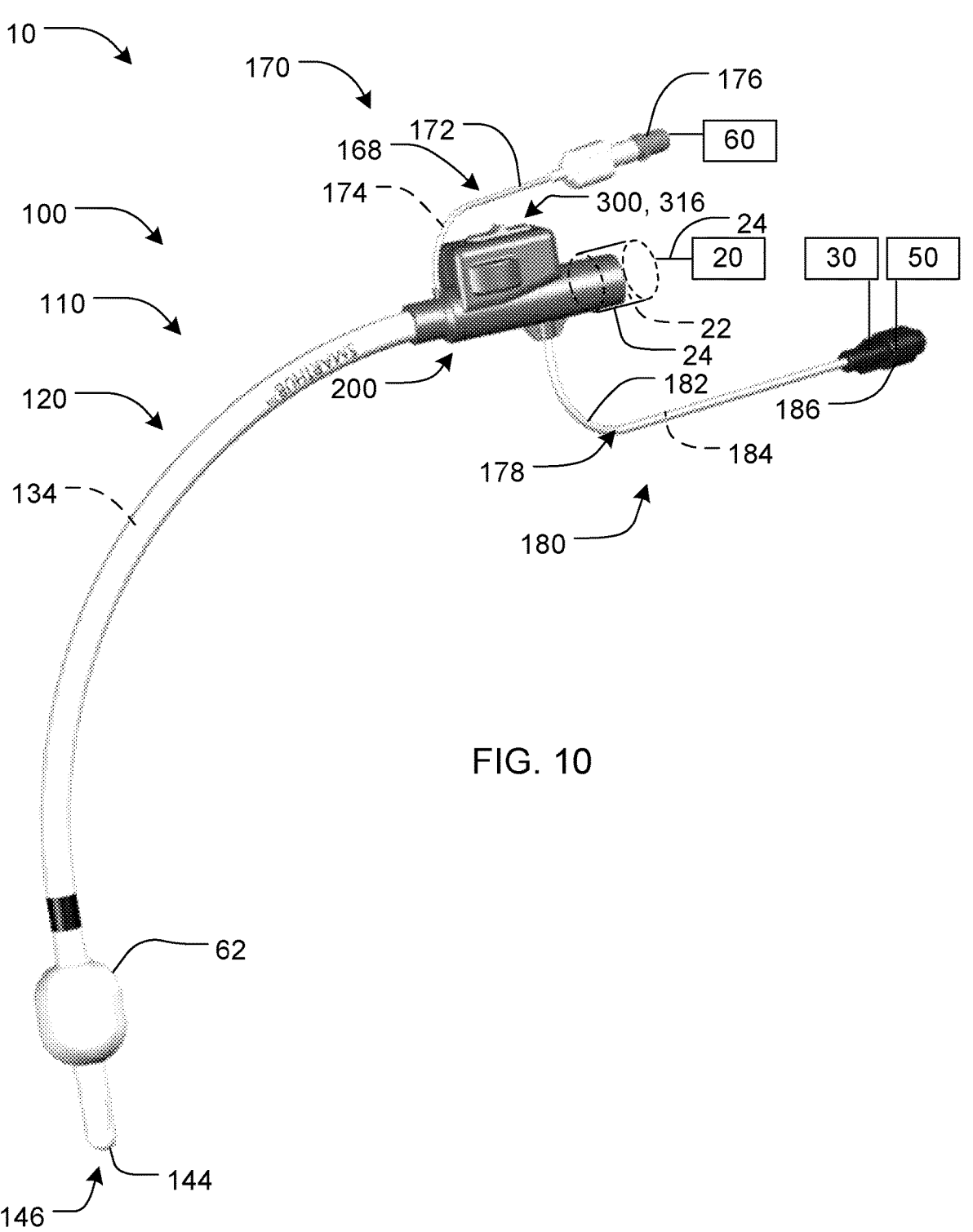
FIG. 10 is a perspective view of another medical system including a medical device comprising a ventilation tube apparatus, and more particularly an endotracheal tube apparatus, according to the present disclosure.
Figure 11:
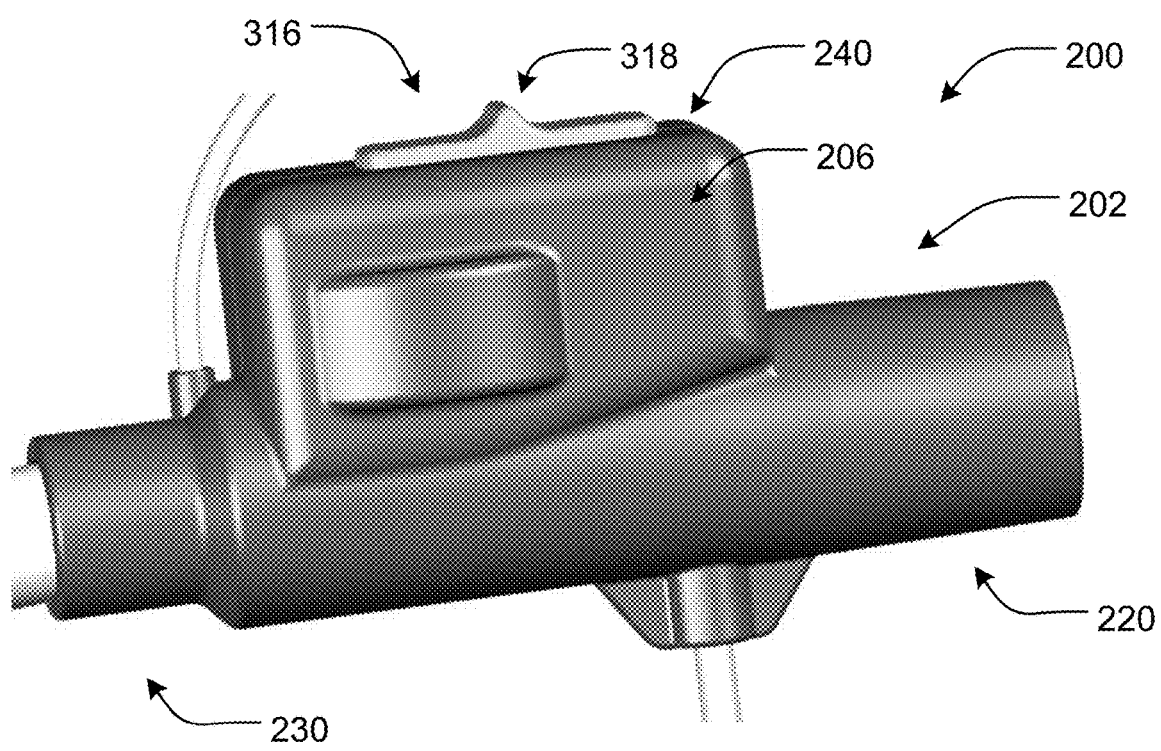
FIG. 11 is a close-up perspective view of a hub connection fitting of the ventilation tube apparatus of FIG. 10.
Figure 12:
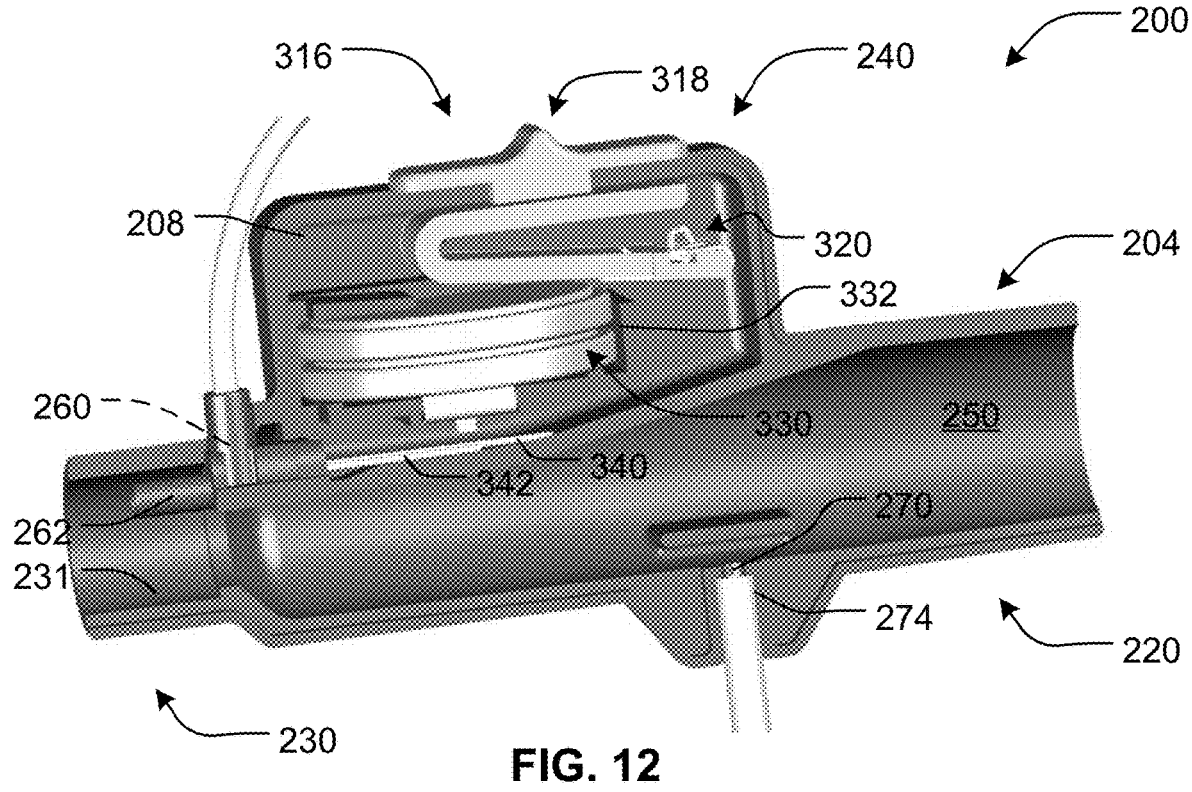
FIG. 12 is a close-up perspective view of the hub connection fitting of FIG. 10 with a portion of the hub connection fitting body removed.
Figure 17:
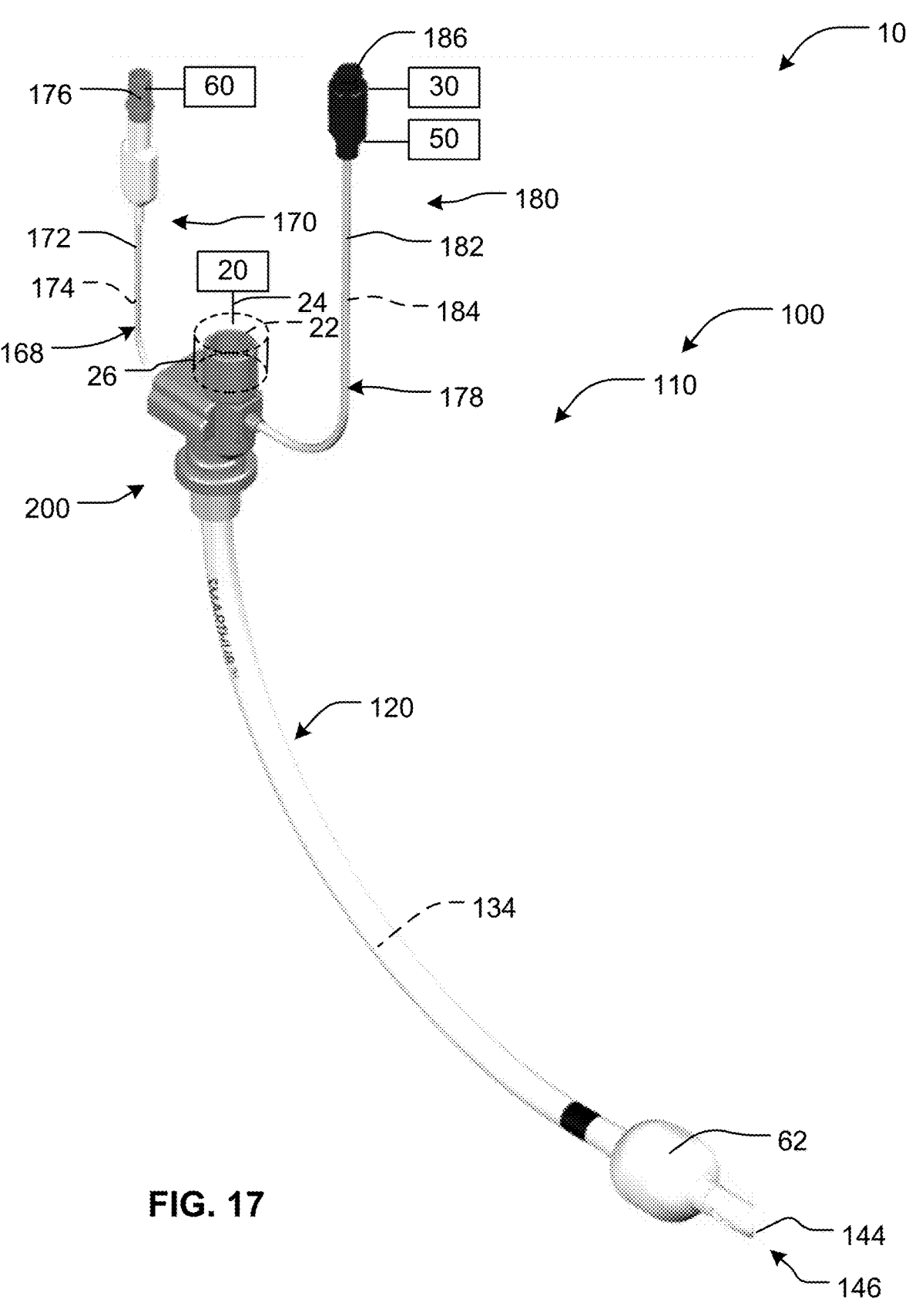
FIG. 17 is a perspective view of another medical system including a medical device comprising a ventilation tube apparatus, and more particularly an endotracheal tube apparatus, according to the present disclosure.
Figure 30A:
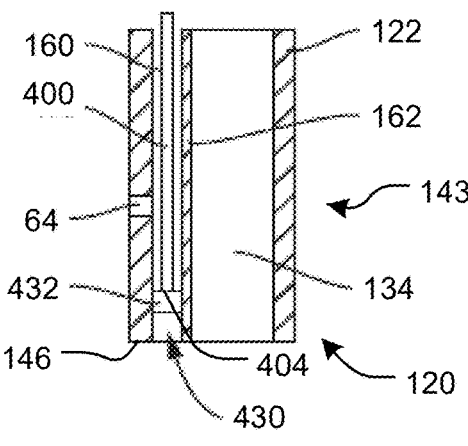
Figure 30B:
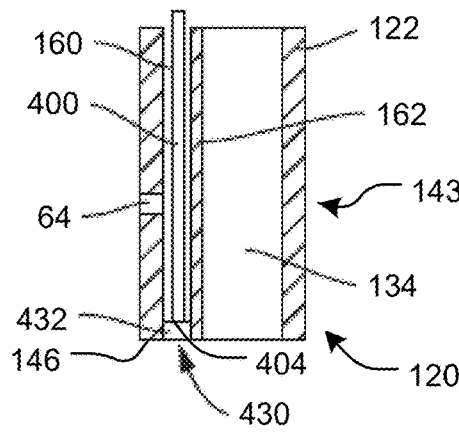
Figure 30C:
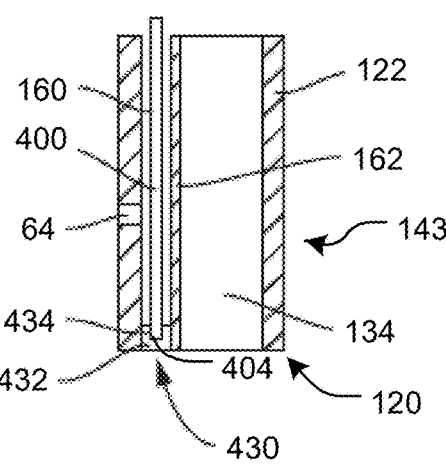
Figure 30D:
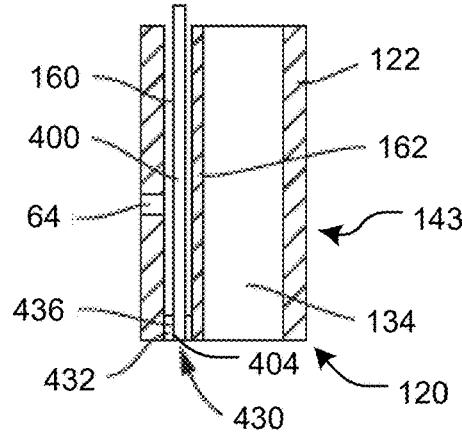
Figure 30E:
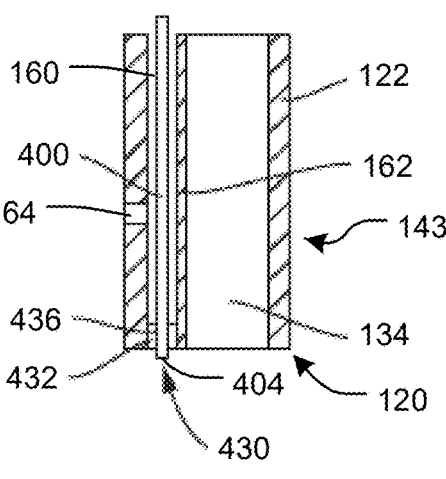
Figure 30F:
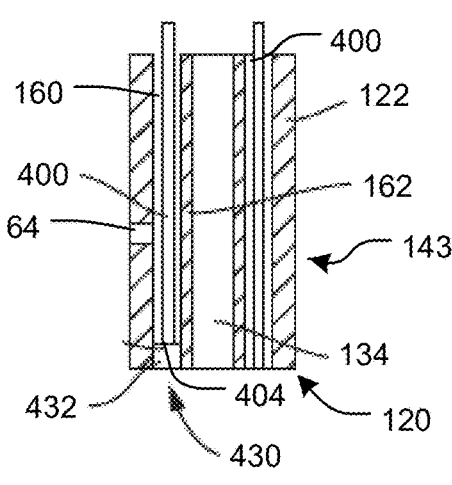
Figure 31:
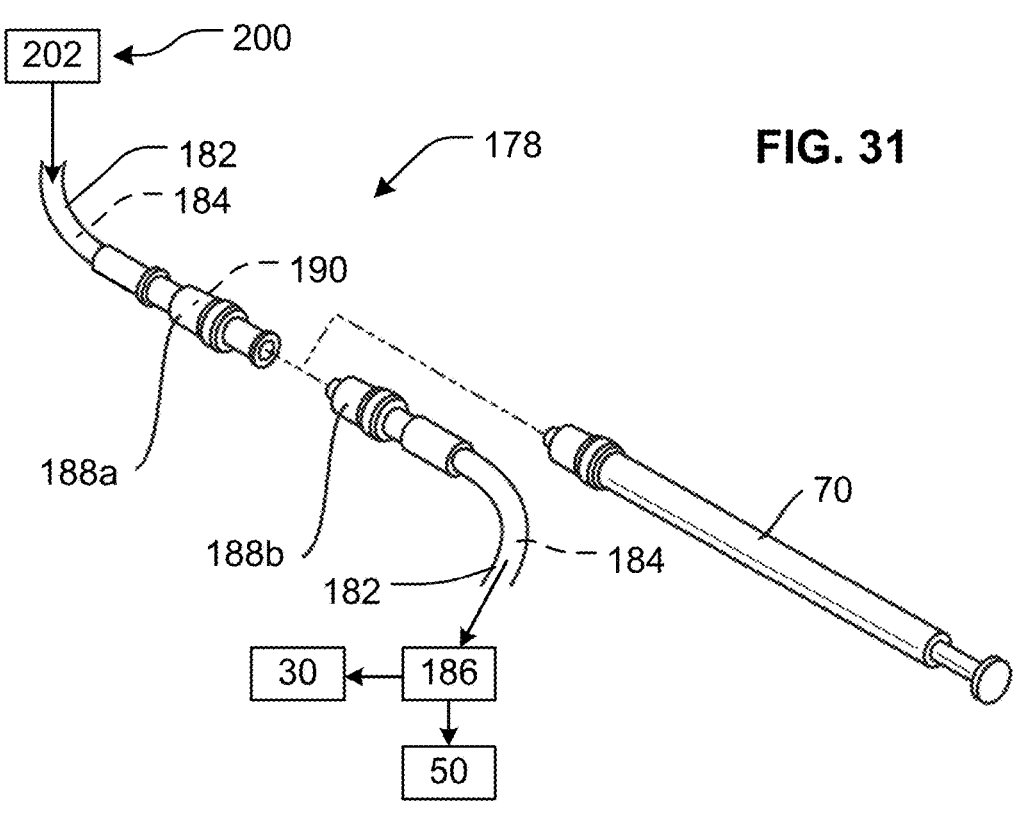
Figure 32A:
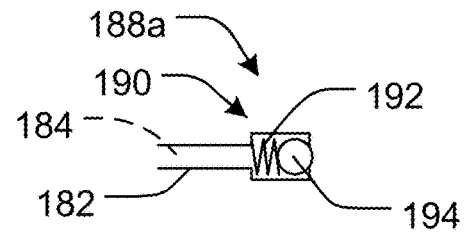
Figure 32B:
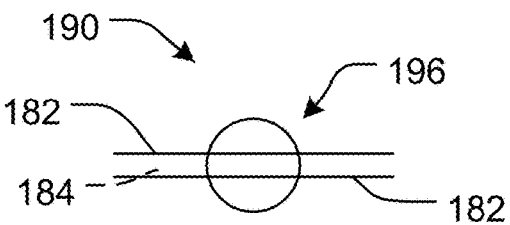
Figure 32C:
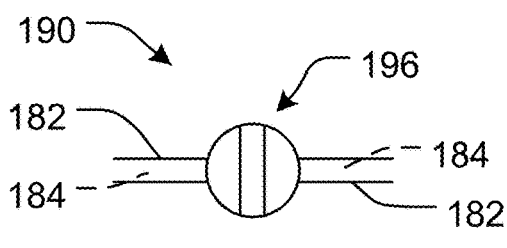
Figure 32D:
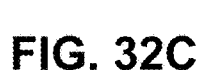
Figures 33, 34:
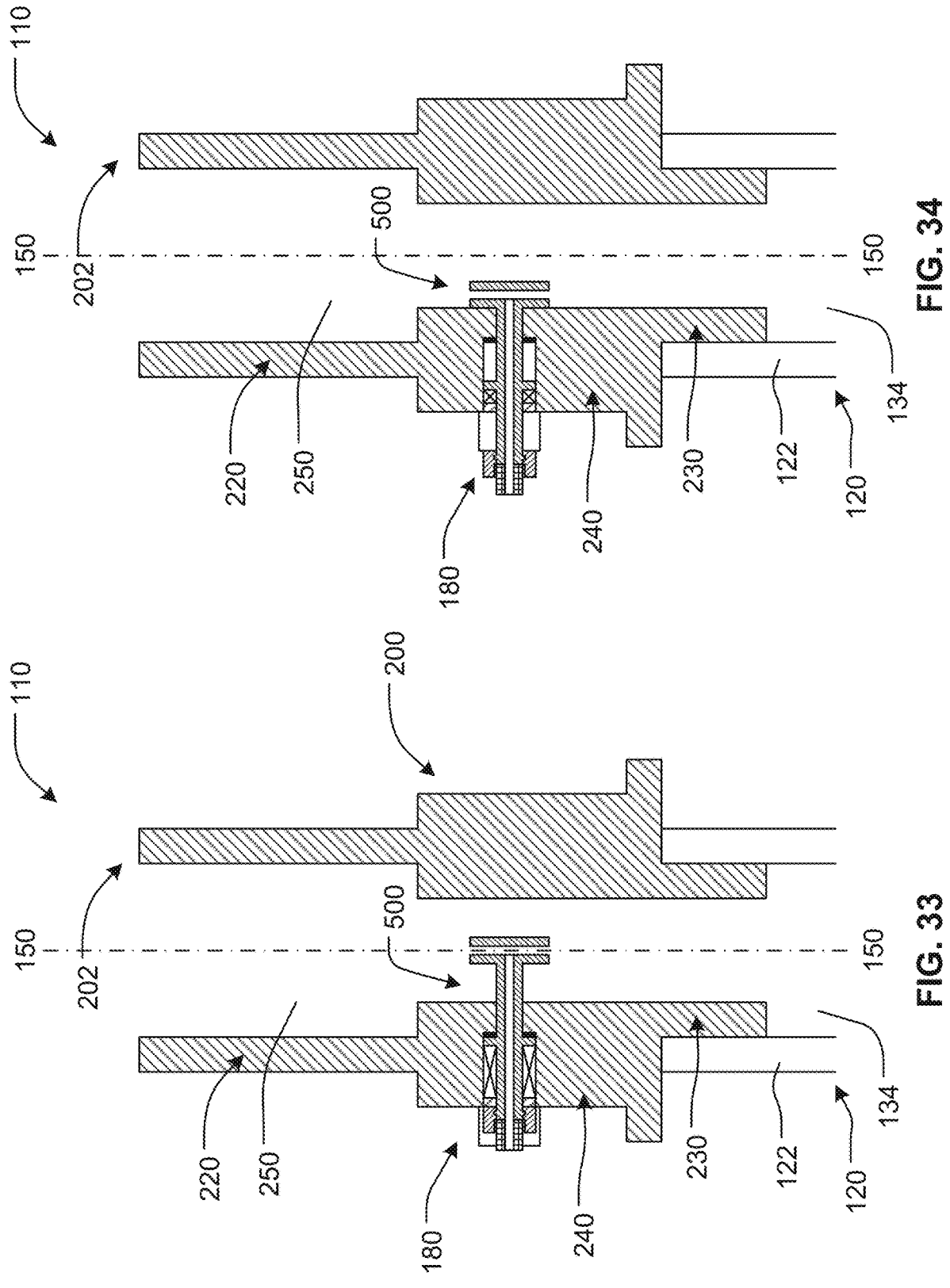
Figures 35, 36, 37:
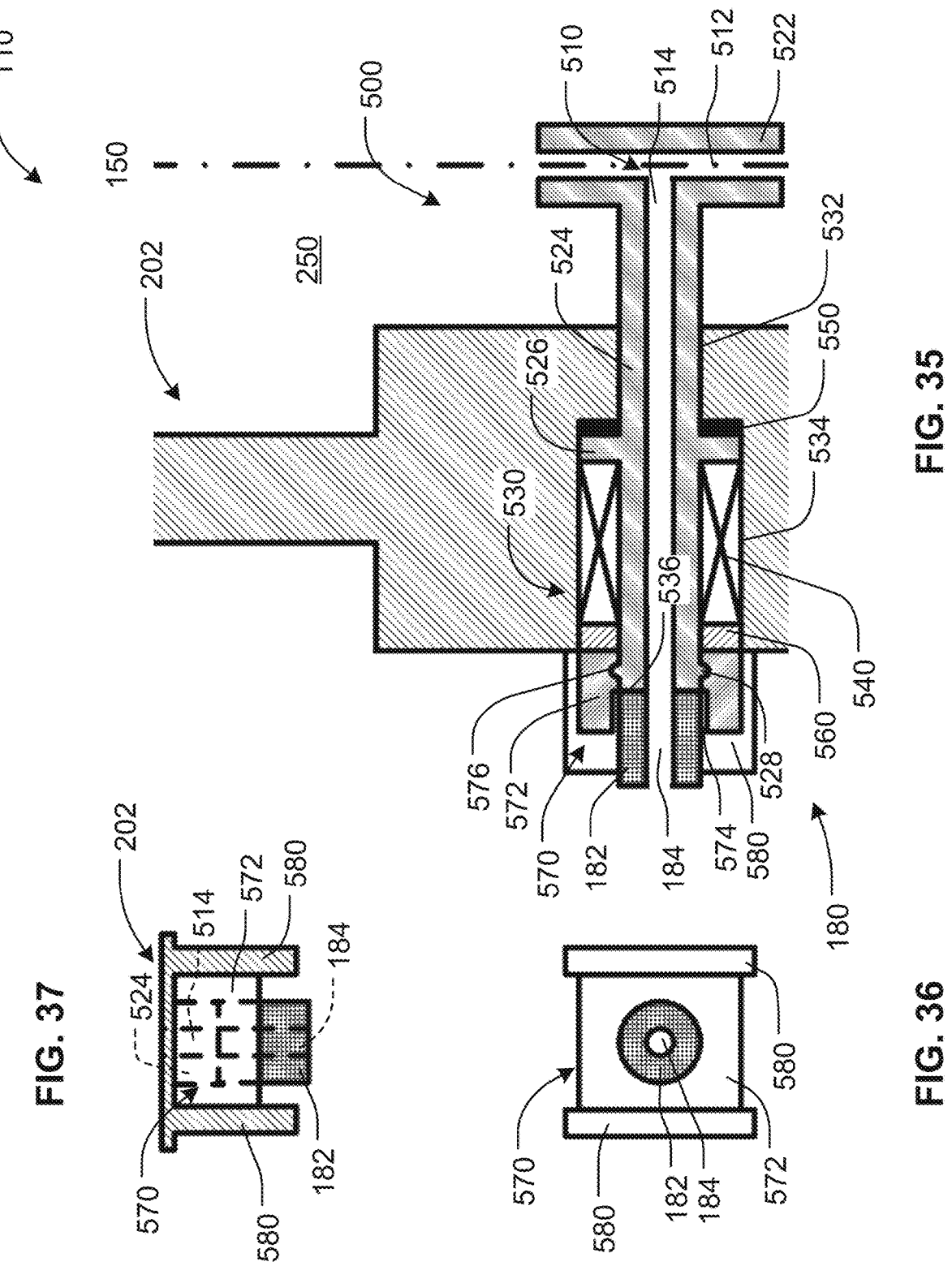
Figures 38, 39, 40:
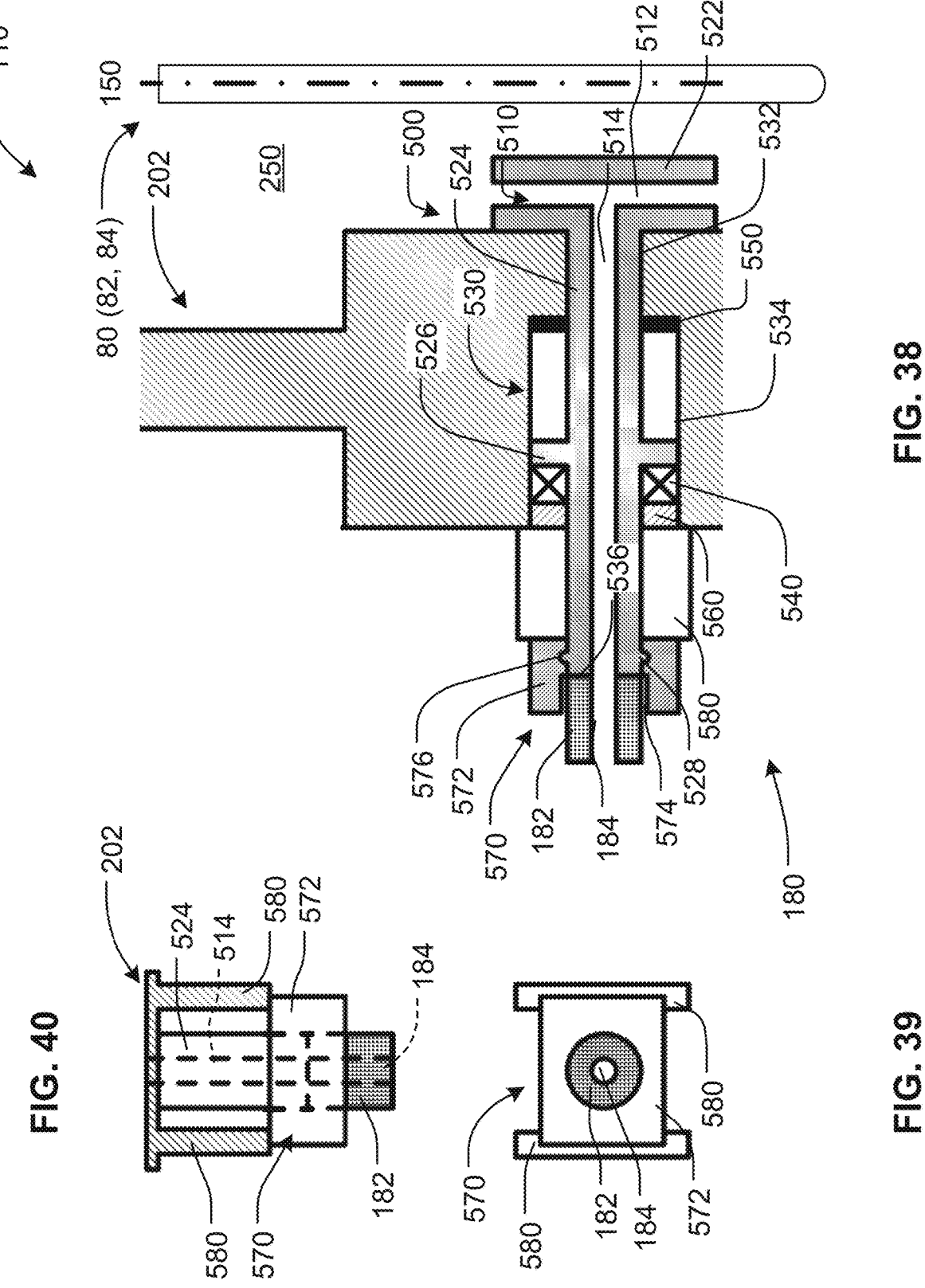
Figures 41, 42:
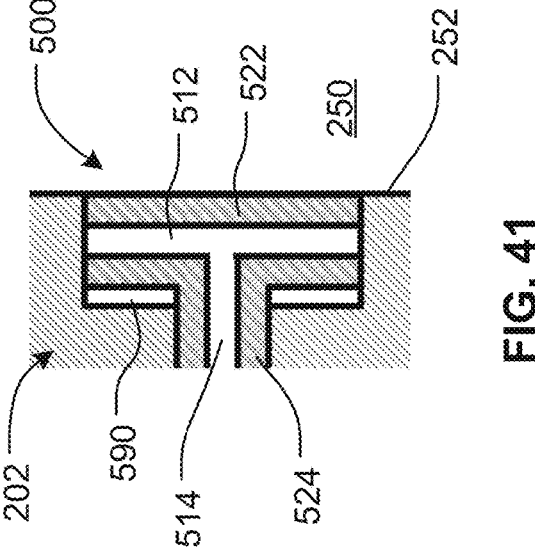

17 with a second body portion of the hub connection fitting body removed and the ventilation tube transparent;

FIG. 28 is a close-up perspective view of the hub connection fitting of the ventilation tube apparatus of FIG. 17 with a first body portion of the hub connection fitting body removed;

FIG. 29 is another close-up perspective view of the hub connection fitting of the ventilation tube apparatus of FIG. 17 with a first body portion of the hub connection fitting body removed;

FIG. 30A is a cross-sectional side view of a distal end region of the ventilation tube apparatus of FIG. 17;

FIG. 30B is a cross-sectional side view of a distal end region of another embodiment of the ventilation tube apparatus of FIG. 17;

FIG. 30C is a cross-sectional side view of a distal end region of another embodiment of the ventilation tube apparatus of FIG. 17;

FIG. 30D is a cross-sectional side view of a distal end region of another embodiment of the ventilation tube apparatus of FIG. 17;

FIG. 30E is a cross-sectional side view of a distal end region of another embodiment of the ventilation tube apparatus of FIG. 17;

FIG. 30F is a cross-sectional side view of a distal end region of another embodiment of the ventilation tube apparatus of FIG. 17;

FIG. 31 is a perspective view of the fluid sampling port including a two-piece (separable) mating connector with a valve;

FIG. 32A is a cross sectional view of a valve in a closed position;

FIG. 32B is a cross sectional view of the valve of FIG. 32A in an opened position;

FIG. 32C is a cross sectional view of another valve in a closed position;

FIG. 32D is a cross sectional view of the valve of FIG. 32C in an opened position;

FIG. 33 is a cross-sectional side view of another ventilation tube apparatus of the present disclosure, particularly an endotracheal tube apparatus, with a movable fluid sampling port fitment of a fluid sampling port in a first position;

FIG. 34 is a cross-sectional side view of the ventilation tube apparatus of FIG. 33, with the movable fluid sampling port fitment in a second position;

FIG. 35 is a close-up cross-sectional view of the movable fluid sampling port fitment in the first position of FIG. 33;

FIG. 36 is a close-up front view of the movable fluid sampling port fitment in the first position of FIG. 33;

FIG. 37 is a close-up cross-sectional top view of the movable fluid sampling port fitment in the first position of FIG. 33;

FIG. 38 is a close-up cross-sectional view of the movable fluid sampling port fitment in the second position of FIG. 34;

FIG. 39 is a close-up front view of the movable fluid sampling port fitment in the second position of FIG. 34;

FIG. 40 is a close-up cross-sectional top view of the movable fluid sampling port fitment in the second position of FIG. 34;

FIG. 41 is a close-up cross-sectional top view of the movable fluid sampling port fitment in another second position of another embodiment;

FIG. 42 is a is a cross-sectional side view of another ventilation tube apparatus, particularly an endotracheal tube apparatus, of the present disclosure, with a deformable fluid sampling port fitment in a first position;

8

Figures 43, 44:
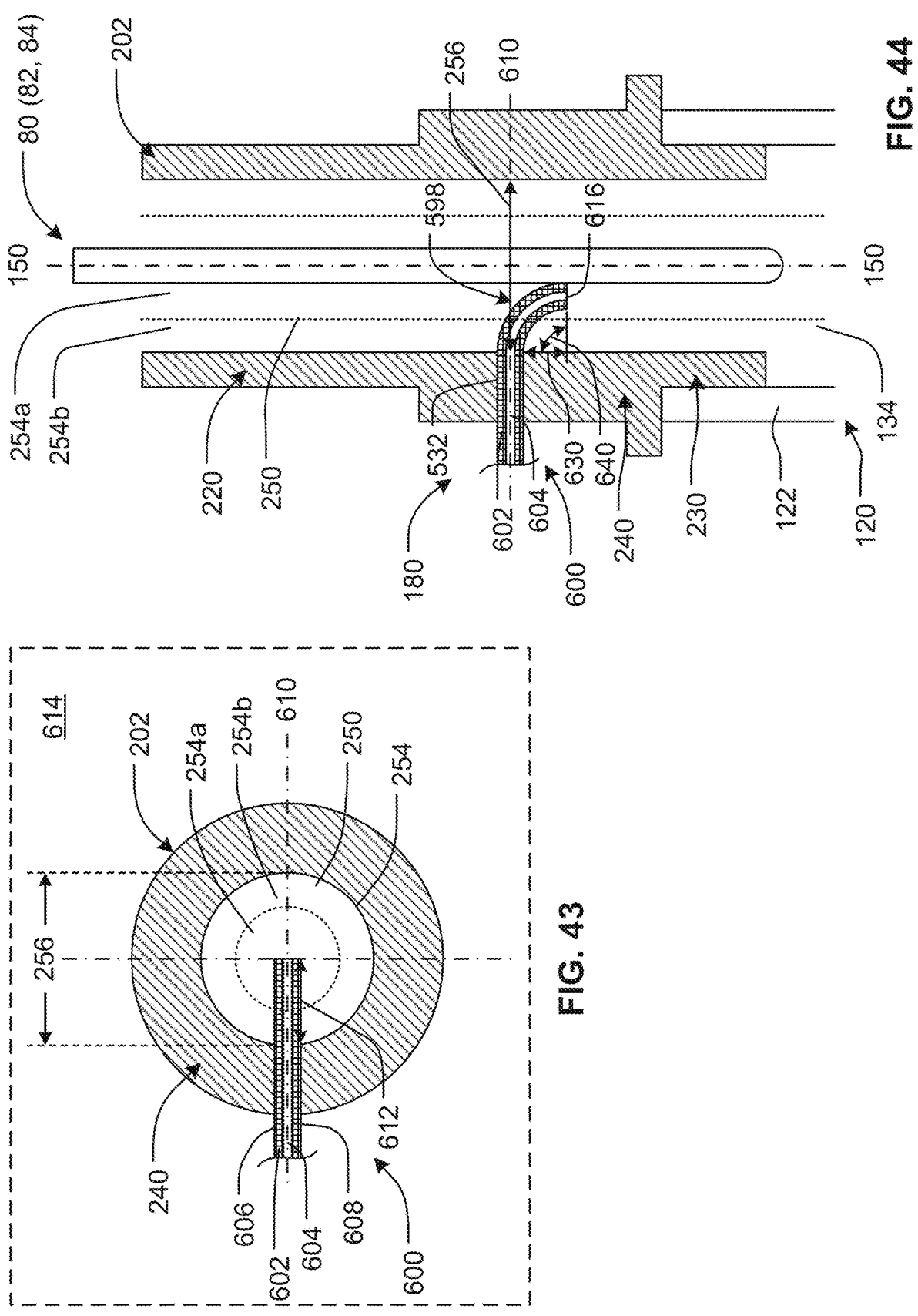
Figures 45, 46, 47, 48:
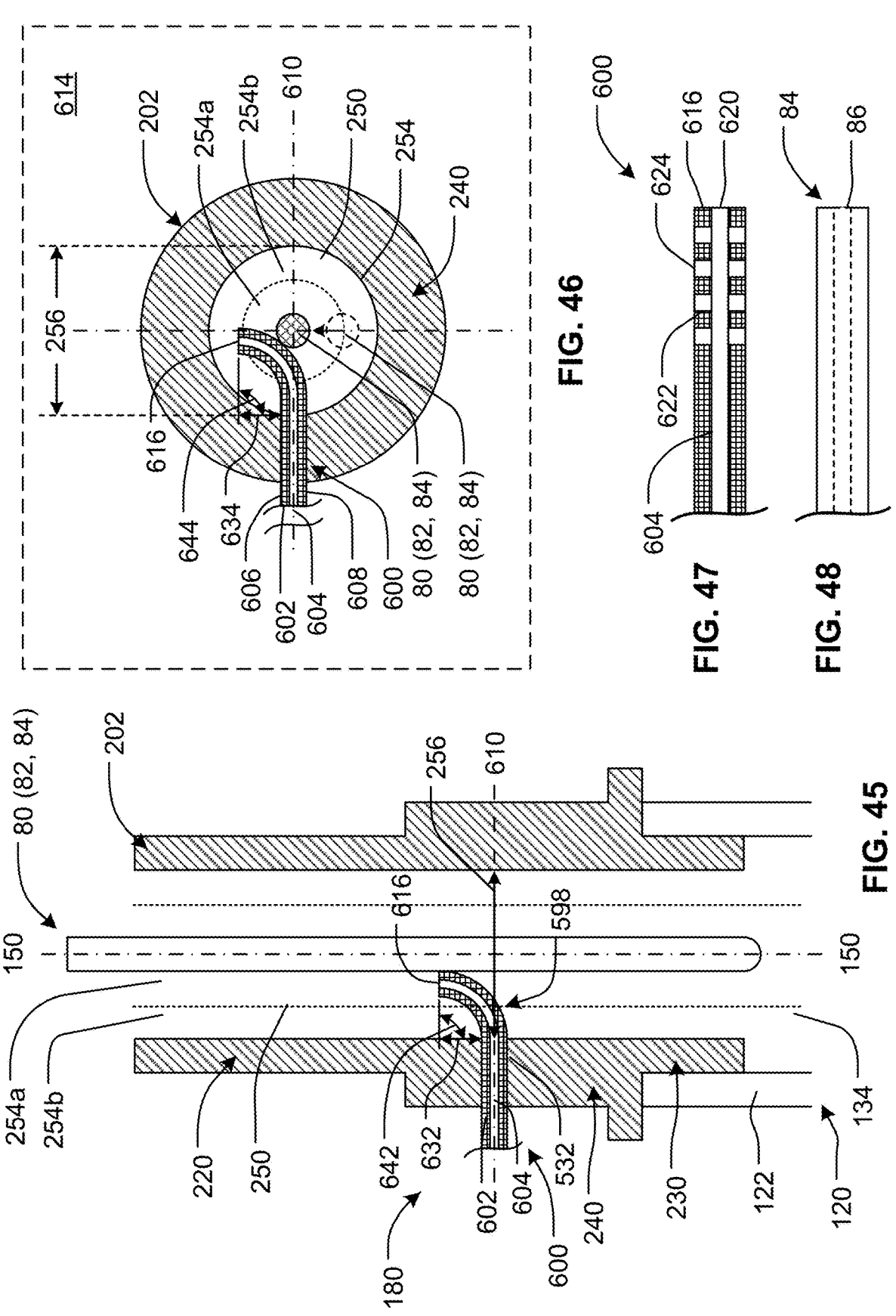
Figures 49, 50:
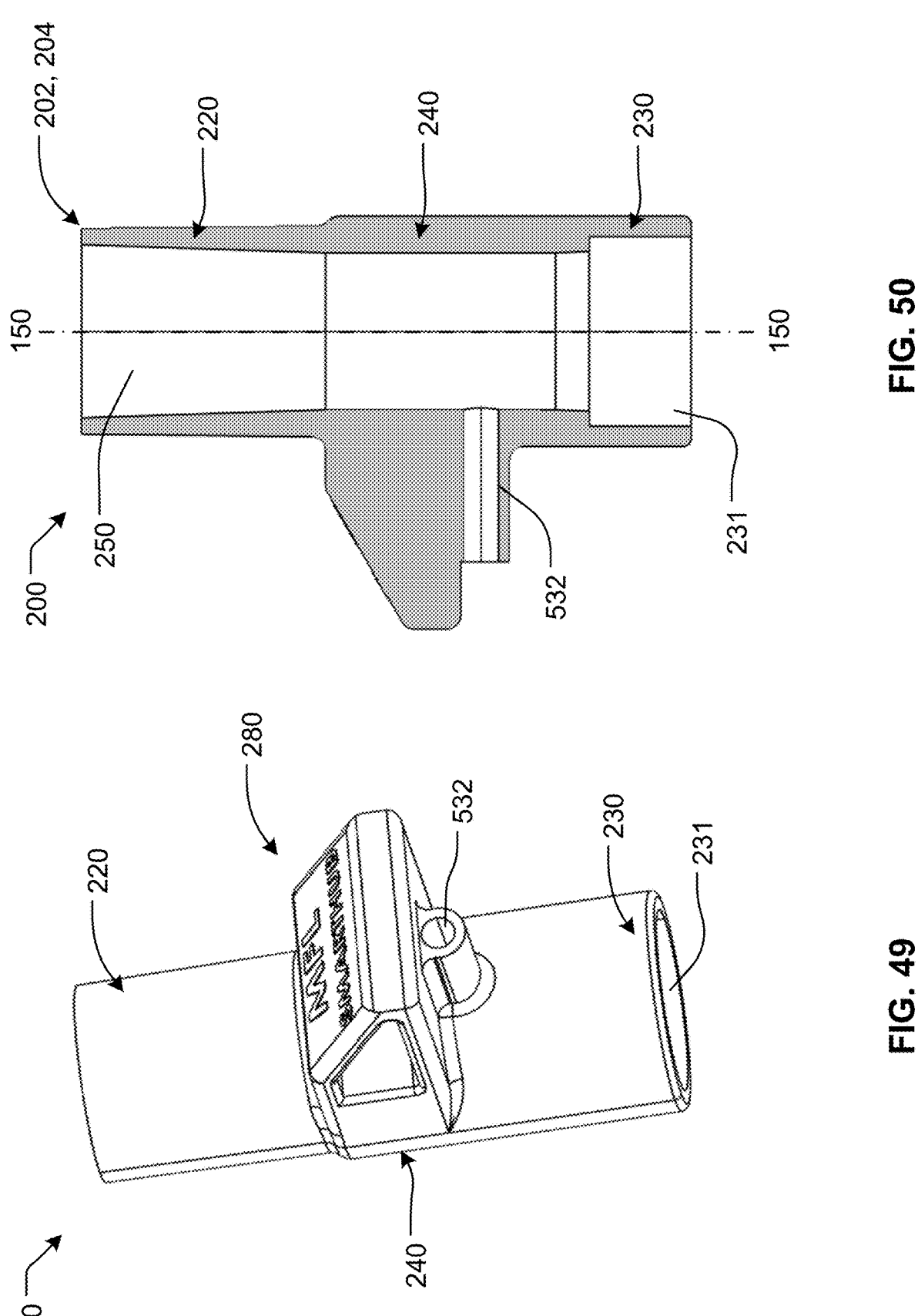
Figures 51, 52:
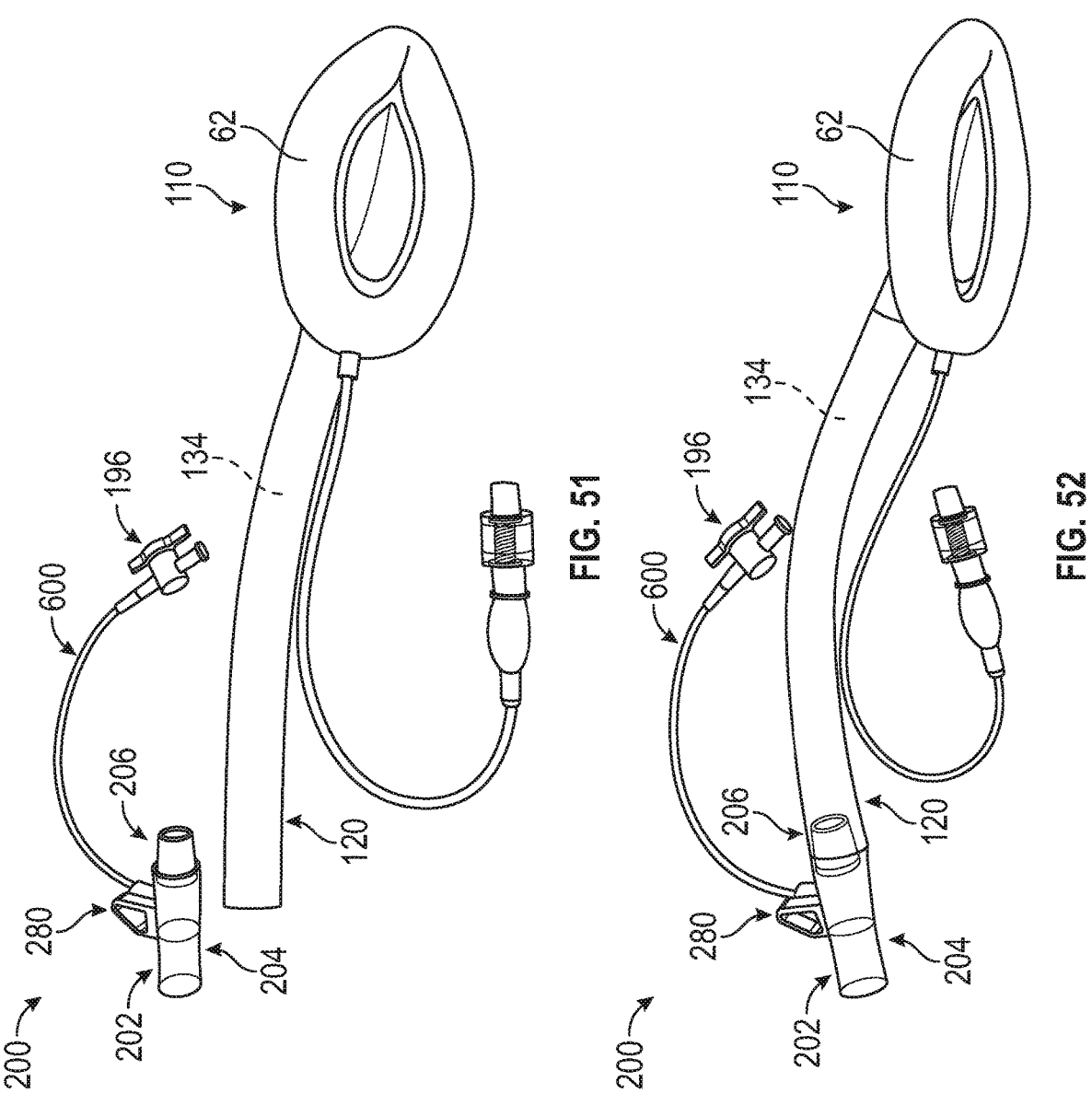

FIG. 43 is a cross-sectional view of the ventilation tube apparatus of FIG. 42 taken along section line 43-43;

FIG. 44 is a is a cross-sectional side view of the ventilation tube apparatus of FIG. 42, with the deformable fluid sampling port fitment in a second position;

FIG. 45 is a is a cross-sectional side view of the ventilation tube apparatus of FIG. 42, with the deformable fluid sampling port fitment in another second position;

FIG. 46 is a is a cross-sectional side view of the ventilation tube apparatus of FIG. 42, with the deformable fluid sampling port fitment in another second position;

FIG. 47 is a cross-sectional side view of another deformable fluid sampling port fitment according to the present disclosure;

FIG. 48 is a side view of an elongated medical instrument in a form of a catheter;

FIG. 49 is a close-up perspective view of another hub connection fitting according to the present disclosure;

FIG. 50 is a cross-sectional side view of the hub connection fitting of FIG. 49;

FIG. 51 is a perspective view of another ventilation (breathing) tube apparatus, according to the present disclosure, before assembly;

FIG. 52 is a perspective view of the ventilation (breathing) tube apparatus of FIG. 51, after assembly;

FIG. 53 is a close-up perspective view of another hub connection fitting according to the present disclosure; and FIG. 54 is a cross-sectional side view of the hub connection fitting of FIG. 51.

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art. Furthermore, throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this disclosure as suitable. In other words, features between the various exemplary embodiments described herein are interchangeable as suitable, and not exclusive.

Referring now to FIGS. 1-9, there is shown a medical system 10 according to the present disclosure, which comprises medical device 100. More particularly, medical device 100 comprises an airway management medical device 110, particularly a ventilation (breathing) tube apparatus in a form of an endotracheal tube apparatus, and more particularly an endotracheal tube apparatus of a medical respiratory system.

While the disclosure may refer to a ventilation/breathing tube apparatus as being an endotracheal tube apparatus, particularly for single-use (disposable) applications as understood in the art (i.e. which are not intended to be re-useable), it should be understood that the present disclosure is not limited to an endotracheal tube apparatus, and the present tube apparatus may have other medical applications other than that of endotracheal tube apparatus.

For example, a medical device 100, comprising a hub connection fitting 200 and ventilation tube 120 may be another airway management medical device, such as an extraglottic medical device (EAD), and more particularly a supraglottic airway device (SAD) as disclosed herein. Also, while endotracheal tube apparatus may be described herein for oral intubation, the apparatus may also be used for tracheal intubation (e.g. cricothyrotomy tube, tracheostomy tube). In still other applications, the tube apparatus may have non-medical applications.

As shown, the airway management medical device 110 is a ventilation (breathing) tube apparatus, and more particularly an endotracheal tube apparatus, insertable into the airway of a host/patient. The ventilation tube apparatus 110 comprises a flexible, elongated, hollow ventilation tube 120, and more particularly an endotracheal tube. As shown, a distal end of the ventilation tube 120 provides a distal end of the ventilation tube apparatus 110 and a proximal end of the hub connection fitting 200 provides a proximal end of the ventilation tube apparatus 110.

Ventilation tube 120 may be extruded (thermoplastic) tubing, which may be referred to as an extrudate, having a constant profile along its length, to be inserted into the trachea of a human host, such as a patient. Exemplary thermoplastic polymer compositions for the ventilation tube 120 may include plasticized polyvinyl chloride or polyolefins (e.g. polypropylene, polyethylene). Ventilation tube 120 may also be formed of an elastomer.

As used herein, an elastomer may be characterized as a material that has an elongation at 23° C. of at least 100%, and which, after being stretched to twice its original length and being held at such for one minute, may recover in a range of 50% to 100% within one minute after release from the stress. More particularly, the elastomer may recover in a range of 75% to 100% within one minute after release from the stress, and even more particularly recover in a range of 90% to 100% within one minute after release from the stress. The elastomer may be comprised of any polymer, including natural or synthetic polymers, and thermoplastic or thermoset polymers. Thus, the elastomer may be either a natural or synthetic elastomer.

Ventilation tube 120 is preferably light transmissive to visible light and substantially transparent. As used herein, substantially transparent may be understood as providing integral transmission of at least 60% of incident light in the visible spectrum (about 400-700 nm wavelength), and more preferably at least 70% of incident light in the visible spectrum, and even more preferably, at least 80% or moreover at least 90% of incident light in the visible spectrum. Also, substantially transparent may be understood to include translucent in accordance with the above.

In certain embodiments, the ventilation tube 120 may have a (longitudinal) length in a range of 7.5 cm to 50 cm (including all ranges and increments there between), and more particularly a length in a range of 17 cm to 23 cm (including all ranges and increments there between). As shown, outer surface 124 of ventilation tube 120 is cylindrical, with a constant diameter, however in other embodiments ventilation tube 120 may not necessarily be cylindrical or have a constant diameter.

Ventilation tube 120 has an outer cylindrical sidewall 122 having the outer surface 124 and an inner surface 126. In certain embodiments, the ventilation tube 120 may have an outer diameter 130 in a range of 5 mm to 15 mm (including all ranges and increments there between), and more particularly in a range of 9 mm to 13 mm (including all ranges and increments there between). The thickness of the outer cylindrical sidewall 122 may be in a range from 0.75 mm to 3 mm (including all ranges and increments there between) and more particularly in a range of 1 mm to 2 mm (including all ranges and increments there between).

Ventilation tube 120 includes a centrally disposed ventilation passageway 134, in the form of a lumen, which extends along the overall length of the ventilation tube 120 from a proximal end opening 140 at a proximal end 142 of the ventilation tube 120 to a distal end opening 144 at a distal end 146 of the ventilation tube 120. As shown, the ventilation passageway 134 shares a common longitudinal axis 150 (shown as the center axis) with the ventilation tube 120. Ventilation passageway 134 may be understood as the ventilation passageway for (endotracheal) intubation and subsequent use of an upstream respirator apparatus 20 (device for maintaining artificial respiration including a ventilator), such as a bag valve mask or a mechanical ventilator as known in the art, connected to ventilation tube apparatus 110 to provide mechanical ventilation to the patient.

Respirator apparatus 20 may also include an impedance threshold device (ITD) as known in the art that selectively prevents unnecessary air from enter the chest/lungs of a patient during the chest wall recoil phase of cardiopulmonary resuscitation (CPR). The ITD may be used in conjunction with a bag valve mask/mechanical ventilator arranged upstream, and the ventilation tube apparatus 110 arranged downstream, as known in the art. Use of the ITD device results in greater vacuum (negative pressure) in the chest/lungs during the chest wall recoil phase. An exemplary ITD is the ResQPOD impedance threshold device. The ITD maintains lower airway pressure and reduces the pressure inside the patient's chest. This reduced pressure draws more blood back to the heart during the decompression phase of CPR. As a result, a greater volume of blood may flow out of the heart during the next compression, which may improve overall blood circulation as compared to standard CPR.

The maximum diameter of the ventilation passageway 134, which is also an inner diameter 132 of ventilation tube 120, may be in a range of 3 mm to 13 mm (including all ranges and increments there between), and more particularly in a range of 7 mm to 11 mm (including all ranges and increments there between).

Ventilation tube 120 includes at least one secondary passageway 160 (which is not a ventilation passageway, hence a non-ventilation passageway). As explained in greater detail below, secondary passageway 160 may be a cuff inflation passageway in fluid communication with an inflation cuff 62, as well as a pneumatic (air) cuff inflation fluid line 168 and cuff inflation port connector 176 of a cuff inflation port 170. For purposes of this disclosure, it should be understood that a cuff inflation port 170 may include all the structures, apart from the ventilation tube 120, which are necessary to affect operation of the inflation cuff 62.

As shown, secondary passageway 160 is provided by a lumen, which has a semi-circular sidewall 162 which is formed unitary (i.e. formed as a single piece monolithic) with the outer cylindrical sidewall 122. As shown, semi-circular sidewall 162 defines a portion of the ventilation passageway 134, along with the outer cylindrical sidewall 122. While the secondary passageway 160 is shown to have a circular (cylindrical) cross-sectional profile (360 degree), it may have a different profile.

As shown, the semi-circular sidewall 162 has a circumference which extends over an arc of approximately 200 degrees. However, the circumference of the arc may range from, for example, 180 degrees to 330 degrees (including all ranges and increments there between), and more particularly 200 degrees to 300 degrees (including all ranges and increments there between). Semi-circular sidewall 162 may have a thickness in a range from 0.5 mm to 2 mm (including all ranges and increments there between) and more particularly in a range of 0.75 mm to 1.5 mm (including all ranges and increments there between).

As shown, the secondary passageway 160 extends parallel with ventilation passageway 134 in ventilation tube 120. As shown, the ventilation passageway 134 and the secondary passageway 160 have a different longitudinal axis (i.e. ventilation passageway 134 and secondary passageway 160 are not coaxial), with the longitudinal axis of the secondary passageway 160 parallel with the longitudinal axis 150 of ventilation passageway 134.

As shown, the overall inner diameter and radius of the secondary passageway 160 is smaller than the overall inner diameter and radius of the ventilation passageway 134, and in a range of 10%-50% of the inner diameter and radius of the ventilation passageway 134 (including all ranges and increments there between) and more particularly in a range of 20%-40% (including all ranges and increments there between) of the inner diameter and radius of the ventilation passageway 134, such as 25-35% of the inner diameter and radius of the ventilation passageway 134 (including all ranges and increments there between).

In addition to ventilation tube 120, ventilation tube apparatus 110 further comprises hub connection fitting 200 that operatively connects the ventilation tube 120 to the respirator apparatus 20. The hub connection fitting 200 comprises a hub connection fitting body 202, which comprises a hub connection fitting first body 204 and a hub connection fitting second body 206, which may both be formed of injection molded thermoplastic, such as polypropylene, polyethylene, polyamide or polyacetal.

The hub connection fitting first body 204 and a hub connection fitting second body 206 are assembleable and mate with one another, with the hub connection fitting second body 206 providing a cover which overlies and covers a hub connection fitting body cavity 208 of the hub connection fitting body 202 formed predominately in the hub connection fitting first body 204, which contains additional components and may be referred to as a component cavity, of the hub connection fitting 200. The hub connection fitting body cavity 208 provides a receptacle for one or more components of a lighting apparatus 300 described in further detail below. The hub connection fitting first body 204 and the hub connection fitting second body 206 are both shown and formed as single (one-piece) bodies having a unitary (monolithic) structure.

The hub connection fitting first body 204 and the hub connection fitting second body 206 are preferably permanently assembled/fastened together, particularly by welding (e.g. ultrasonic welding) to inhibit assess to the hub connection fitting body cavity 208 and the components therein after assembly. In this manner, the hub connection fitting first body 204 and the hub connection fitting second body 206 are not intended to be dissembled and may not be separable/disassembled (inseparable) without breaking or other damage to the hub connection fitting body 202. As used herein, components are considered to be permanently assembled/fastened when such components would be plausibly damaged as a result of separation or are otherwise not intended to be separated during prescribed use thereof.

Hub connection fitting body 202, and more particularly hub connection fitting first body 204, comprises a proximal body portion 220, which provides a male connector portion shown to be cylindrical, and a distal body portion 230, which provides a female connector portion shown to be cylindrical, separated by an intermediate/middle body portion 240. Hub connection fitting body 202, and more particularly hub connection fitting first body 204, further comprises a ventilation passageway 250, which extends through the proximal body portion 220, intermediate/middle body portion 240 and distal body portion 230, which, as shown, are defined solely by the hub connection fitting first body 204, without the hub connection fitting second body 206. Ventilation passageway 250 is to provide fluid communication between ventilation passageway 134 of ventilation tube 120 and the respirator apparatus 20.

The outer diameter of the proximal body portion 220 of the hub connection fitting 200 is dimensioned to be inserted into a passageway 22 formed by circular sidewall 26 of a respirator tube 24 of the respirator apparatus 20, which also may be referred to as a ventilator tube of a ventilator) and interference (frictionally) fit with the inside diameter of the sidewall thereof.

In addition to ventilation passageway 250, hub connection fitting body 202, and more particularly hub connection fitting first body 204, includes a secondary passageway 260 which is arranged to connect and provide fluid communication with the secondary passageway 160 of ventilation tube 120. More particularly, secondary passageway 260 defines a portion of the cuff inflation passageway in fluid communication with the inflation cuff 62 and the cuff inflation port connector 176 of the cuff inflation port 170. As shown, secondary passageway 260 is formed solely by the hub connection fitting first body 204, without the hub connection fitting second body 206.

Hub connection fitting 200 also includes a secondary passageway 270 which connects and provides fluid communication with the ventilation passageway 250 of the hub connection fitting 200 and the ventilation passageway 134 of the ventilation tube 120. More particularly, secondary passageway 270 defines a portion of a fluid (exhaled gas(es) from the patient) sampling passageway in fluid communication with a connector 186 of a port 180, which may be referred to as a fluid sampling port connector and a fluid sampling port, respectively. Alternatively, or additionally, secondary passageway 270 defines a portion of a drug delivery passageway in fluid communication with connector 186 of port 180, which may be referred to as a drug delivery port connector and a drug delivery port, respectively. In other words, port 180 may be a fluid sampling port and/or a drug delivery port. As shown, secondary passageway 270 is formed solely by the hub connection fitting first body 204, without the hub connection fitting second body 206.

For purposes of this disclosure, it should be understood that port 180 may include all the structures, apart from the ventilation tube 120, which are necessary to affect operation of fluid sampling and/or drug delivery, respectively.

Longitudinal (parallel) to the longitudinal axis of the hub connection fitting 200/body 202, and more particularly hub connection fitting first body 204, distal body portion 230 includes a cylindrical recess 231 into which a cylindrical proximal end region 141 of the ventilation tube 120 is inserted/disposed in and overlaps against, particularly with the outer surface 124 of the cylindrical proximal end region 141 in contact with the inner cylindrical surface 232 of the cylindrical recess 231. As shown, cylindrical recess 231 is formed solely by the hub connection fitting first body 204, without the hub connection fitting second body 206.

It should be understood that any combination of interference fits, adhesive bonding and welding may be used to mechanically (positive mechanical and/or friction) and/or adhesively join the cylindrical proximal end region 141 of the ventilation tube 120 within cylindrical recess 231, particularly with the outer surface 124 of the cylindrical proximal end region 141 of the ventilation tube 120 in contact with the inner cylindrical surface 232 of the cylindrical recess 231. For example, the outer surface 124 of the cylindrical proximal end region 141 of the ventilation tube 120 may be at least one of interference fit, adhesive bonded and welded with the inner cylindrical surface 232 of the cylindrical recess 231. It should be understood that any combination of interference fits, adhesive bonding and welding may be used for any of the connections alone or in conjunction with another joining method.

Within cylindrical recess 231, distal end of the secondary passageway 260 may be formed by a circular (e.g. cylindrical) sidewall, which provides a distal male connector portion 262, which is dimensioned to be inserted into secondary passageway 160 of ventilation tube 120 and interference (frictionally) fit with the inside diameter of the semi-circular sidewall 162. As shown, the male connector portion 262 may be formed as one piece with the hub connection fitting first body 204. Alternatively, such may be formed separately from the hub connection fitting first body 204 as a separate piece. In such regard, the male connector portion 262 may be made of metal or a plastic different than that of the hub connection fitting first body 204 for increased strength. When formed as a separate piece, such may be joined to the hub connection fitting first body 204 by threaded engagement and/or ultrasonic welding, similar to threaded insert.

Thus, the hub connection fitting 200 includes a cuff inflation passageway connector, provided by male connector portion 262, which connects to the secondary passageway 160 of the ventilation tube 120 for cuff inflation. In the foregoing manner, the secondary passageway 160 may be sealed between ventilation tube 120 and hub connection fitting body 202, and more particularly hub connection fitting first body 204, with a fluid (air) tight seal, i.e. a hermetic seal. In certain alternative embodiments, alternatively or in addition to, the male connector portion 262 may be adhesively bonded and/or welded with the inside diameter of the semi-circular sidewall 162 of secondary passageway 160 in addition to being interference fit.

The proximal end of each secondary passageway 260, 270 includes a counter-bore 264, 274, respectively. Counter-bore 264 is configured to receive the distal end portion of a tube 172 of cuff inflation fluid line 168, which may be an extruded flexible/bendable (elastically deformable and recoverable) tubing segment of extruded (thermoplastic) tubing having a constant profile along its length, in fluid communication with the inflation cuff 62 and the cuff inflation port connector 176 of the cuff inflation port 170.

Counter-bore 274 is configured to receive the distal end portion of a tube 182 of fluid line 178, which may be referred to as a fluid sampling and/or drug delivery fluid line and also be an extruded flexible/bendable (elastically deformable and recoverable) tubing segment, in fluid communication with the connector 186 of the port 180. In order to join the two components together, the distal end portion of tubes 172, 182 may be interference fit with counter-bore 264, 274, respectively. Alternatively, or in conjunction with the interference fit, the distal end portion of tubes 172, 182 may be adhesive bonded with counter-bore 264, 274, respectively, with an adhesive and/or the distal end portion of tubes 172, 182 may be welded with counter-bore 264, 274, respectively. Exemplary thermoplastic polymer compositions for tubes 172, 182 may include plasticized polyvinyl chloride, polyolefins (e.g. polypropylene, polyethylene) and elastomers. Alternatively, or in addition to, the tubes 172, 182 may be formed of a polymer composition having a Shore A durometer hardness, as measured by ASTM D2240-15 (2021), in a range of 40-95 Shore A durometer hardness, and more particularly in the range of 50-90 Shore A durometer hardness.

As shown, the tube 182, in fluid communication with the connector 186 of the port 180, includes a tube passageway 184, shown as a lumen, which forms part of the passageway, which may be referred to as a fluid sampling and/or drug delivery passageway, which extends through hub connection fitting first body 204 (as secondary passageway 270) and ventilation passageway 250, 134 of the hub connection fitting first body 204 and ventilation tube 120, respectively. As shown, the proximal end of tube 182 is connected to connector 186, which is shown as a threaded connector. When port 180 provides a fluid sampling port, connector 186 connects to an analyzing/monitoring apparatus 30. In certain embodiments, port 180 as a fluid sampling port may be a carbon dioxide sampling port, and analyzing/monitoring apparatus 30 may be a carbon dioxide analyzer/monitor (e.g. a capnograph).

With use of ventilation tube apparatus 110, gases exhaled by the patient may enter ventilation passageway 134 of ventilation tube 120 at the distal end opening 144 of ventilation tube 120, and then flow through ventilation passageway 134 of ventilation tube 120 and ventilation passageway 250 of hub connection fitting 200 and then thereafter flow through secondary passageway 270 of hub connection fitting 200 and passageway 184 of tube 182, and thereafter through connector 186 and into analyzing/monitoring apparatus 30.

Alternatively, or additionally, when port 180 provides a drug delivery port, connector 186 connects to a drug delivery device 50, such as a syringe, which delivers a drug/fluid through connector 186, passageway 184 of tube 182, secondary passageway 270 of hub connection fitting 200, and into the ventilation passageway 250 of hub connection fitting 200 and the ventilation passageway 134 of ventilation tube 120.

Tube 172 in fluid communication with the inflation cuff 62 and the cuff inflation port connector 176 of the cuff inflation port 170 includes a tube passageway 174, shown as a lumen, which forms part of the cuff inflation passageway, which extends through hub connection fitting first body 204 (as secondary passageway 260) and ventilation tube 120 (as secondary passageway 160). As shown, the proximal end of tube 172 is connected to cuff inflation port connector 176, which connects with a cuff inflation device 60.

As shown, unlike secondary passageway 270, secondary passageway 260 of hub connection fitting 200 is not in fluid communication with ventilation passageway 250 within the hub connection fitting 200. Also, at a distal end region 143 of the ventilation tube 120, the secondary passageway 160 is sealed/occluded distal to an inflation cuff inlet/outlet opening aperture 64. The secondary passageway 160 is sealed/occluded particularly by a light-emitting device 302 of the lighting apparatus 300, explained in greater detail below. The light-emitting device 302 comprises a light source 306, such as a light-emitting diode (LED), which is dimensioned to be disposed within secondary passageway 160 of ventilation tube 120 and interference (frictionally) fit with the inside diameter of the semi-circular sidewall 162 as to form a fluid (air) light seal, i.e. a hermetic seal, between the light-emitting device 302 and the ventilation tube 120.

The light source 306 may then be used to emit light from the distal end 146 of the ventilation tube 120 as explained in greater detail below.

Also as shown, the inflation cuff inlet/outlet opening aperture 64 is formed in the outer cylindrical sidewall 122 to the secondary passageway 160 (proximal to the distal end), such that air from cuff inflation device 60 may flow through cuff inflation port connector 176, passageway 174 of tube 172, secondary passageway 260 of hub connection fitting 200, secondary passageway 160 of ventilation tube 120, through inflation cuff inlet/outlet opening aperture 64 and to inflation cuff to inflate such, and vise-versa to deflate such.

Turning now to the lighting apparatus 300, in addition to the light-emitting device 302 and light source 306 mentioned above, lighting apparatus 300 further comprises a slide switch 316, which comprises a slide switch body 318 which carries a elastically deformable slide switch electrical contact 320. Slide switch 316, and more particularly slide switch body 318, is configured to move in a first direction (proximally) to elastically deform the slide switch electrical contact 320 upon contact with power source 330, shown to comprise a battery, and place the slide switch electrical contact 320 in electrical contact/communication with power source 330 of the lighting apparatus 300. Slide switch 316, and more particularly slide switch body 318, is also configured to move in a second direction (distally) to remove the slide switch electrical contact 320 from electrical contact/communication with power source 330 and elastically recover the slide switch electrical contact 320 from its contact position to its non-contact position. As shown, slide switch body 318, slide switch electrical contact 320 and power source 330 are all disposed in the hub connection fitting body cavity 208 of hub connection fitting 200. Power source 330 is held in a power source holder 332, which may also be referred to as a battery power source holder, within hub connection fitting body cavity 208.

As such, when slide switch 316 is in the distal (off) position, the slide switch electrical contact 320 is not in contact with power source 330 and, hence, the light source 306 does not receive power from power source 330.

Alternately, when slide switch 316 is in the proximal (on) position, the slide switch electrical contact 320 is in contact with power source 330 and, hence, the light source 306 receives power from power source 330 to emit light upon forming of a closed circuit with electrical (wire) conductors 340, 342. As shown, the electrical (wire) conductors 340, 342 extend through wall 344 disposed at the proximal end of the secondary passageway 160, particularly provided by a plug formed of an elastomer, which forms an interference (frictional) fit with the electrical (wire) conductors 340, 342 as well as the inside diameter of the secondary passageway 260 as to form a fluid (air) light seal, i.e. a hermetic seal therebetween.

When ventilation tube apparatus 110 is provided by the manufacturer, the power source 330 may be positioned distally (off) out of electrical contact with slide switch electrical contact 320 to inhibit the lighting apparatus 300 from powering prior to desired use. In other words, the electrical (wire) conductors 340, 342 are initially arranged in an open circuit.

During the insertion of ventilation tube apparatus 110 into a patient, the lighting apparatus 300 may be activated to assist in proper positioning of the ventilation tube apparatus 110 in the trachea as opposed to the esophagus. In doing so, light emitted from lighting apparatus 300, and more particularly light source 306 of light-emitting device 302, may be observed through the chest of the patient to further aid in proper positioning.

Light emitted from light source 306 may generally be white (colorless) light, which may be understood as a mixture of all of the wavelengths of the visible spectrum, i.e. the visible portion of the electromagnetic spectrum. White light may also have a correlated color temperature (CCT) of between about 3000 and 8000 K. White light with a CCT of 4000 or less may have a yellowish/reddish color, while white light with a CCT of 8000 K may be bluish in color.

In certain applications, the light emitted from light source 306 may include ultraviolet light, which has a frequency of between 10 nm to 380 nm. More particularly, the ultraviolet light may be UV-C light having a frequency of between 100 nm to 280 nm. The UV-C light emitted from light source 306 may be used for ultraviolet germicidal irradiation (UVGI), which may be understood as a disinfection method which uses short-wavelength ultraviolet (UV-C) light to kill or inactivate microorganisms (e.g. mucus build-up on and/or in the ventilation tube or other tubing, as well as the patient).

Referring now to FIGS. 10-16, there is shown another embodiment of a ventilation tube apparatus 110, and more particularly an endotracheal tube apparatus, according to the present disclosure. Hub connection fitting 200 again comprises a hub connection fitting body 202 having a proximal body portion 220, which provides a male connector portion shown to be cylindrical, and a distal body portion 230, which provides a female connector portion shown to be cylindrical, separated by an intermediate/middle body portion 240. Also, again, hub connection fitting 200 further comprises a ventilation passageway 250, which extends through the proximal body portion 220, intermediate/middle body portion 240 and distal body portion 230.

However, unlike the prior embodiment, the proximal body portion 220, distal body portion 230 and the intermediate/middle body portion 240 are defined by both the hub connection fitting first body 204 and the hub connection fitting second body 206. In doing so, as shown, the hub connection fitting first body 204 and the hub connection fitting second body 206 separate along a parting line which extends along a full longitudinal length of the hub connection fitting body 202, which separates the hub connection fitting body 202 into two half bodies. Similar to the prior embodiment, the hub connection fitting first body 204 and the hub connection fitting second body 206 are permanently assembled/fastened together, particularly by welding (e.g. ultrasonic welding) to inhibit assess to the hub connection fitting body cavity 208 and the components therein after assembly.

As shown, the power source 330 also comprises a plurality of 3 volt batteries arranged electrically in series, particularly to provide a power output of 6 volts, and an output of 1500-2500 lux by the light source 306.

Also, the male connector portion 262 (to be inserted into the secondary passageway 160 of ventilation tube 120) and the counter-bore 264, which provides a female connector (to receive the distal end portion of tube 172), are formed by a separate, injection molded (plastic), T-shaped, cuff inflation port fitment 350, which is joined with the hub connection fitting first body 204 and the hub connection fitting second body 206, particularly by being sandwiched and welded therebetween. Similar to the prior embodiment, when assembled, the wall 344, again in a form of a plug, forms an interference (frictional) fit with the electrical (wire) conductors 340, 342 as well as the inside diameter of plug receptacle 346 of the secondary passageway 260 as to form a fluid (air) light seal, i.e. a hermetic seal therebetween.

Referring to FIGS. 17-30, there is shown another embodiment of a ventilation tube apparatus 110 according to the present disclosure.

Similar to the prior embodiments, ventilation tube apparatus 110 comprises a ventilation tube 120, and more particularly an endotracheal tube, and hub connection fitting 200 that operatively connects the ventilation tube 120 to a respirator apparatus 20. The hub connection fitting 200 comprises a hub connection fitting body 202, which comprises a hub connection fitting first body 204 and a hub connection fitting second body 206, which may both be formed of injection molded thermoplastic, such as polypropylene, polyethylene, polyamide or polyacetal.

The hub connection fitting first body 204 and the hub connection fitting second body 206 are assembleable and mate with one another, as described in greater detail below, with the hub connection fitting second body 206 joined directly and intermediately to the hub connection fitting first body 204 and the ventilation tube 120. The hub connection fitting first body 204 and the hub connection fitting second body 206 are both shown and formed as single (one-piece) bodies having a unitary (monolithic) structure.

The hub connection fitting first body 204 and the hub connection fitting second body 206 are permanently assembled/fastened together, particularly by welding (e.g. ultrasonic welding) or use of adhesive. As explained in greater detail below, the hub connection fitting first body 204 and the hub connection fitting second body 206 are shown formed as separate bodies, particularly so that the hub connection fitting first body 204 can be fastened to one of a plurality of different hub connection fitting second bodies 206 each having a different diameter of the hub connection fitting second body counter-bore recess 219 to facilitate use of a different diameter ventilation tube 120 (e.g. pediatric, adolescent, adult), respectively, which may have different colors to facilitate quick identification of the size of the ventilation tube 120.

In such regards, the hub connection fitting first body 204 may be used universally with different hub connection fitting second bodies 206 sized to a particular host/patient. However, it should be understood that for the present embodiment, hub connection fitting first body 204 and hub connection fitting second body 206 may be formed as single (one-piece) body having a unitary (monolithic) structure (requiring no assembly) rather than as two separate bodies which are subsequently assembled.

With regards to assembly, as shown by FIG. 27, hub connection fitting first body 204 comprises a hub connection fitting first body outer annular ring 210 separated from a hub connection fitting first body inner annular ring 212 by a hub connection fitting first body annular recess 211. The inner side of hub connection fitting first body inner annular ring 212, along with hub connection fitting first body circular shoulder 213, form a hub connection fitting first body counter-bore recess 214. As shown by FIG. 28, hub connection fitting second body 206 comprises a hub connection fitting second body outer annular ring 215 separated from a hub connection fitting second body inner annular ring 217 by a hub connection fitting second body annular recess 216.

Figures 20, 21:
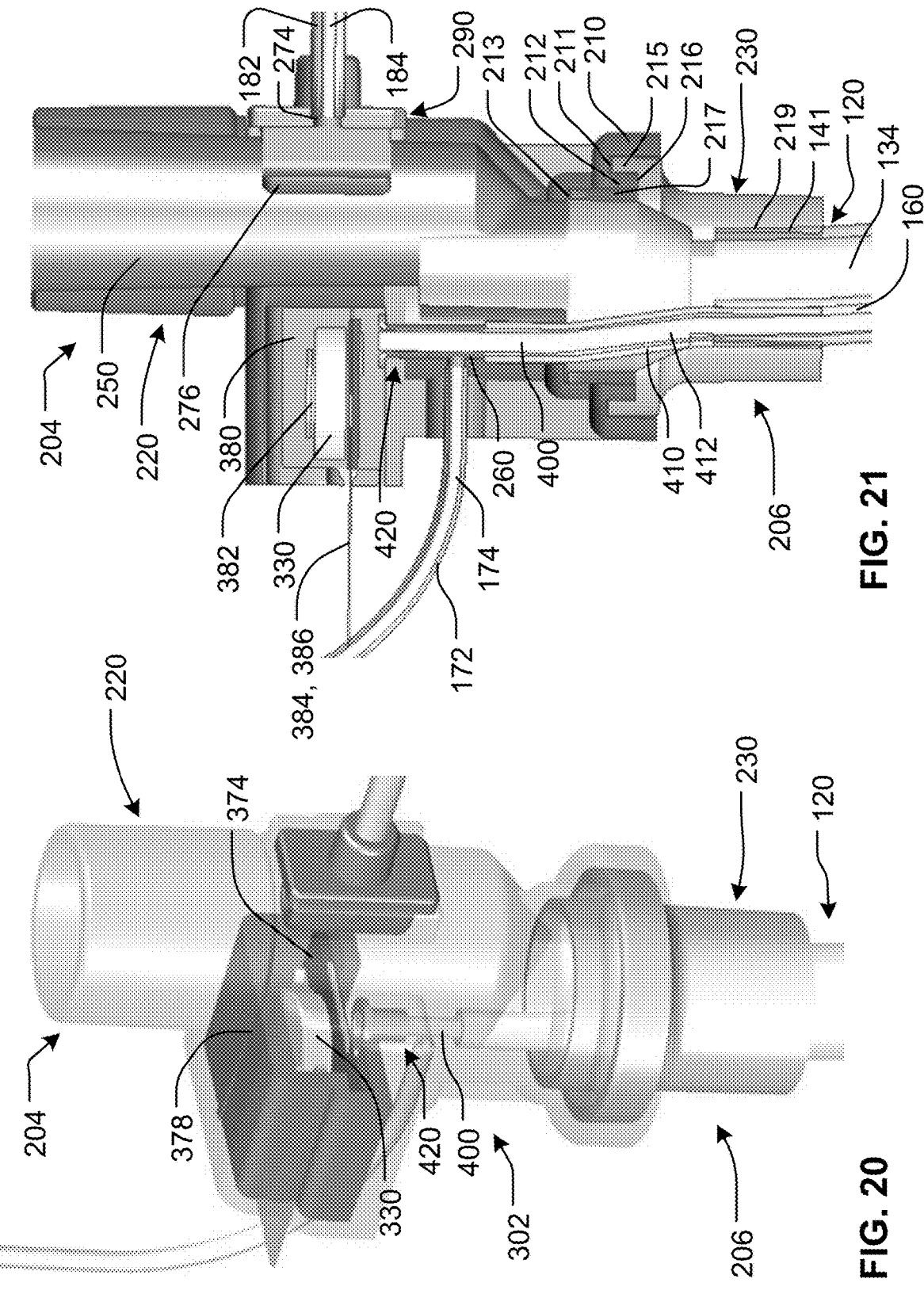
FIG. 20 is a close-up perspective view of the hub connection fitting of FIG. 18 with a portion of the hub connection fitting body shown transparent.
FIG. 21 is a close-up cross-sectional side view of the hub connection fitting of FIG. 18.

As shown by FIG. 21, when hub connection fitting first body 204 and hub connection fitting second body 206 are assembled, hub connection fitting first body inner annular ring 212 is disposed in hub connection fitting second body annular recess 216, and hub connection fitting second body outer annular ring 215 is disposed in the hub connection fitting first body annular recess 211, while hub connection fitting second body inner annular ring 217 is disposed in hub connection fitting first body counter-bore recess 214 and abutting hub connection fitting first body circular shoulder 213. Upon being assembled, hub connection fitting first body inner annular ring 212 may be (permanently) bonded, particularly ultrasonically welded against separation, to hub connection fitting second body 206 within hub connection fitting second body annular recess 216 and/or hub connection fitting second body outer annular ring 215 may be (permanently) bonded, particularly ultrasonically welded against separation, to hub connection fitting first body 204 within the hub connection fitting first body annular recess 211.

Ventilation tube 120 is inserted/disposed in and overlaps against hub connection fitting second body counter-bore recess 219, particularly with the outer surface 124 of the cylindrical proximal end region 141 in contact with inner cylindrical surface 232 of the hub connection fitting second body counter-bore recess 219, with the proximal end 142 of the ventilation tube 120 abutting hub connection fitting second body circular shoulder 218.

In contrast to the prior embodiments where the secondary passageway 270 and the counter-bore 274 to receive tube 182 was formed solely by the hub connection fitting first body 204, or by the hub connection fitting first body 204 and the hub connection fitting second body 206, the secondary passageway 270 and the counter-bore 274 are formed by a separate, injection molded (plastic), fluid sampling port fitment 290, which is joined with the hub connection fitting first body 204 particularly by being welded to a frame 246 defining an aperture 244. As shown, secondary passageway 270 of the fluid sampling port fitment 290 is T-shaped, extending though the counter-bore 274 and the tubular wall 276 substantially transverse (e.g. within 20 degrees of being perpendicular), and more particularly perpendicular, thereto.

Figures 18, 19:
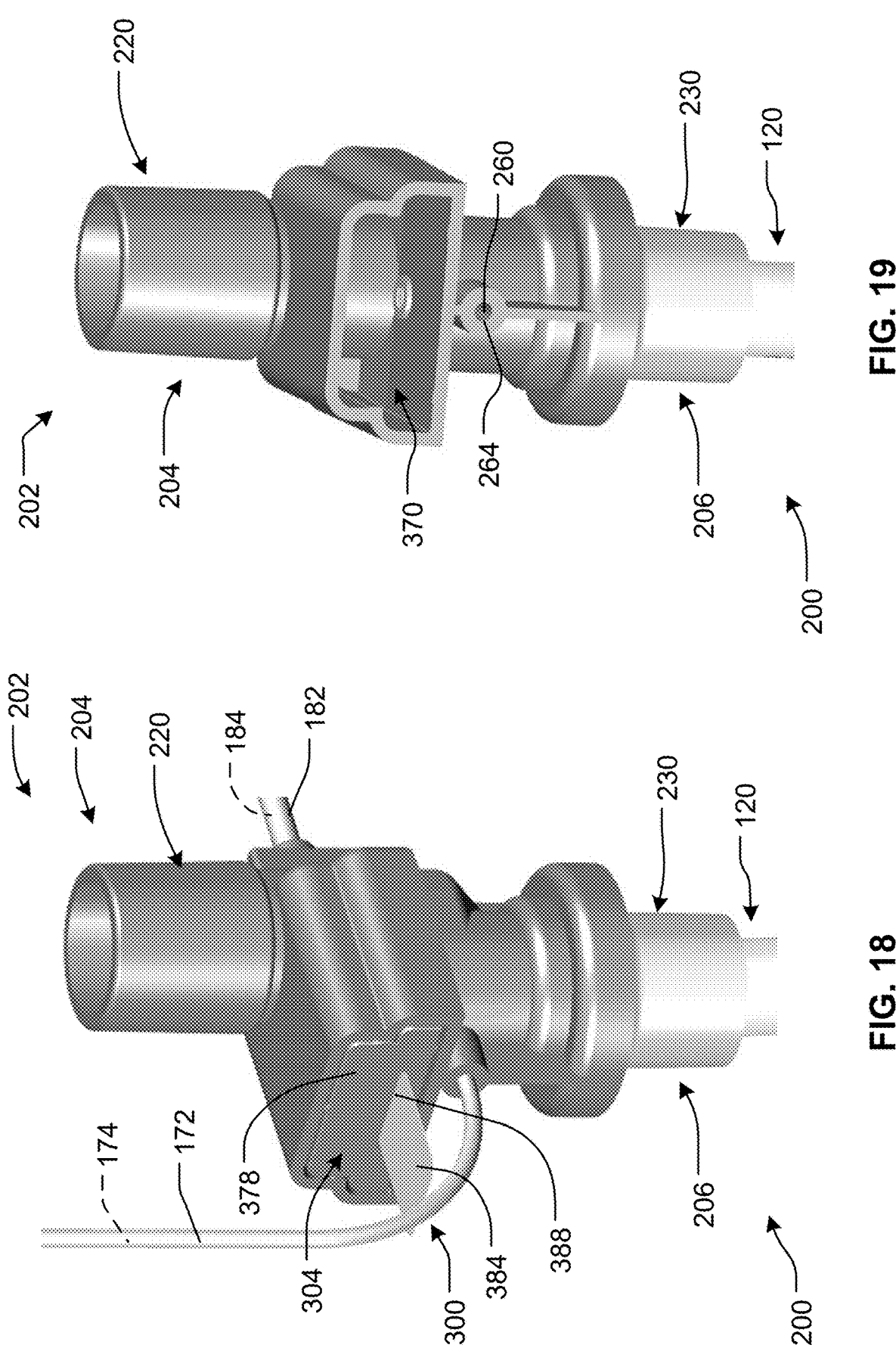
FIG. 18 is a close-up perspective view of a hub connection fitting of the ventilation tube apparatus of FIG. 17.
FIG. 19 is a close-up perspective view of the hub connection fitting of FIG. 18 with a portion of the hub connection fitting body removed.

Similar to the prior embodiments, the ventilation tube apparatus 110 comprises a lighting apparatus 300. Lighting apparatus 300 may comprise a light-emitting device 302, which may include a light-source module 304, coupled with hub connection fitting first body 204. As best shown in FIG. 19, light-source module 304 may be insertable into and removable from a light-source module cavity/receptacle 370 formed in the hub connection fitting first body 204. Also as shown, the light-source module 304 is isolated from the ventilation passageway 250 of the hub connection fitting 200.

Figures 22, 23, 24:
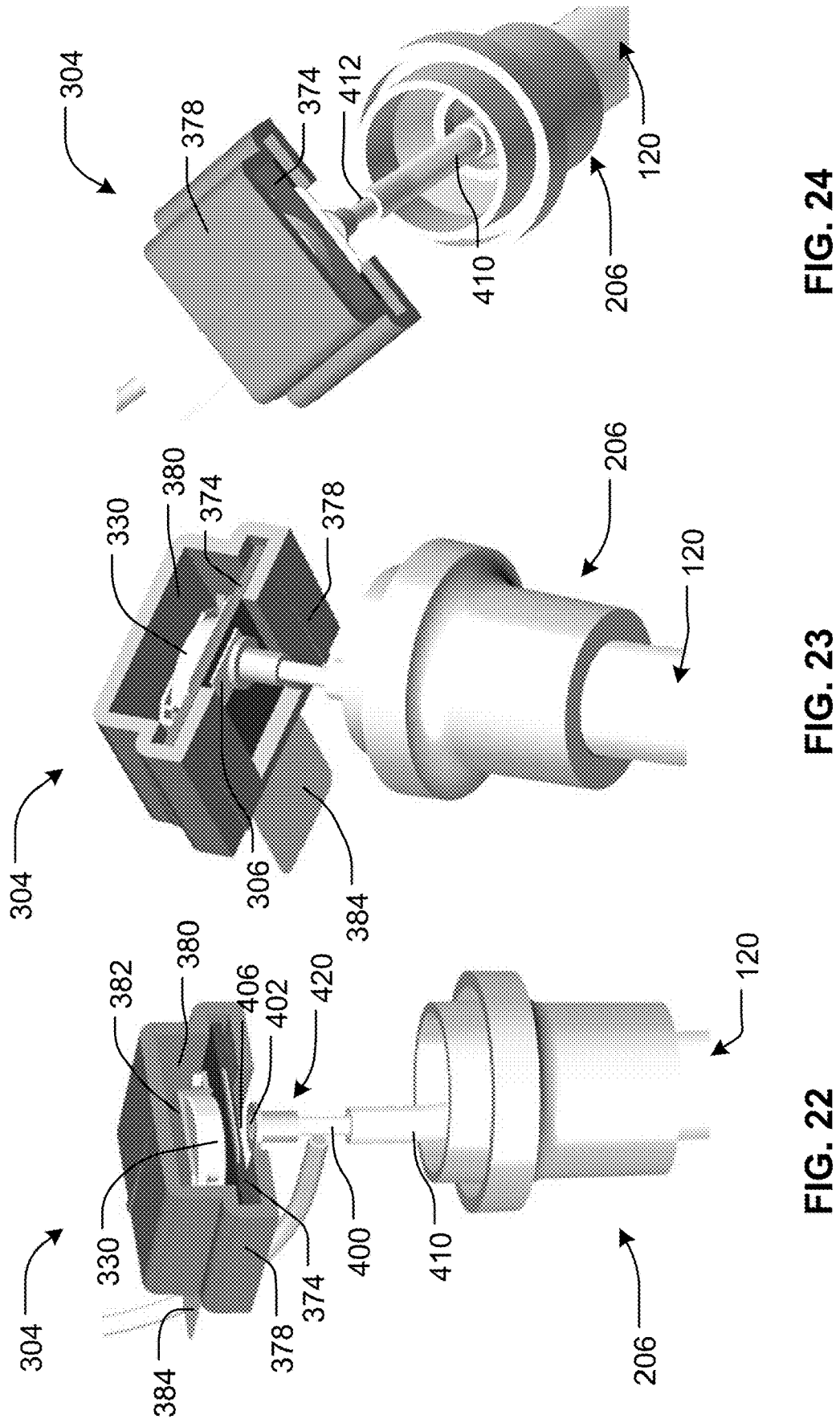
FIG. 22 is a close-up perspective view of certain components of the hub connection fitting of FIG. 18.
FIG. 23 is another close-up perspective view of the components of the hub connection fitting of FIG. 22.
FIG. 24 is another close-up perspective view of the components of the hub connection fitting of FIG. 22.
Figures 25, 26:
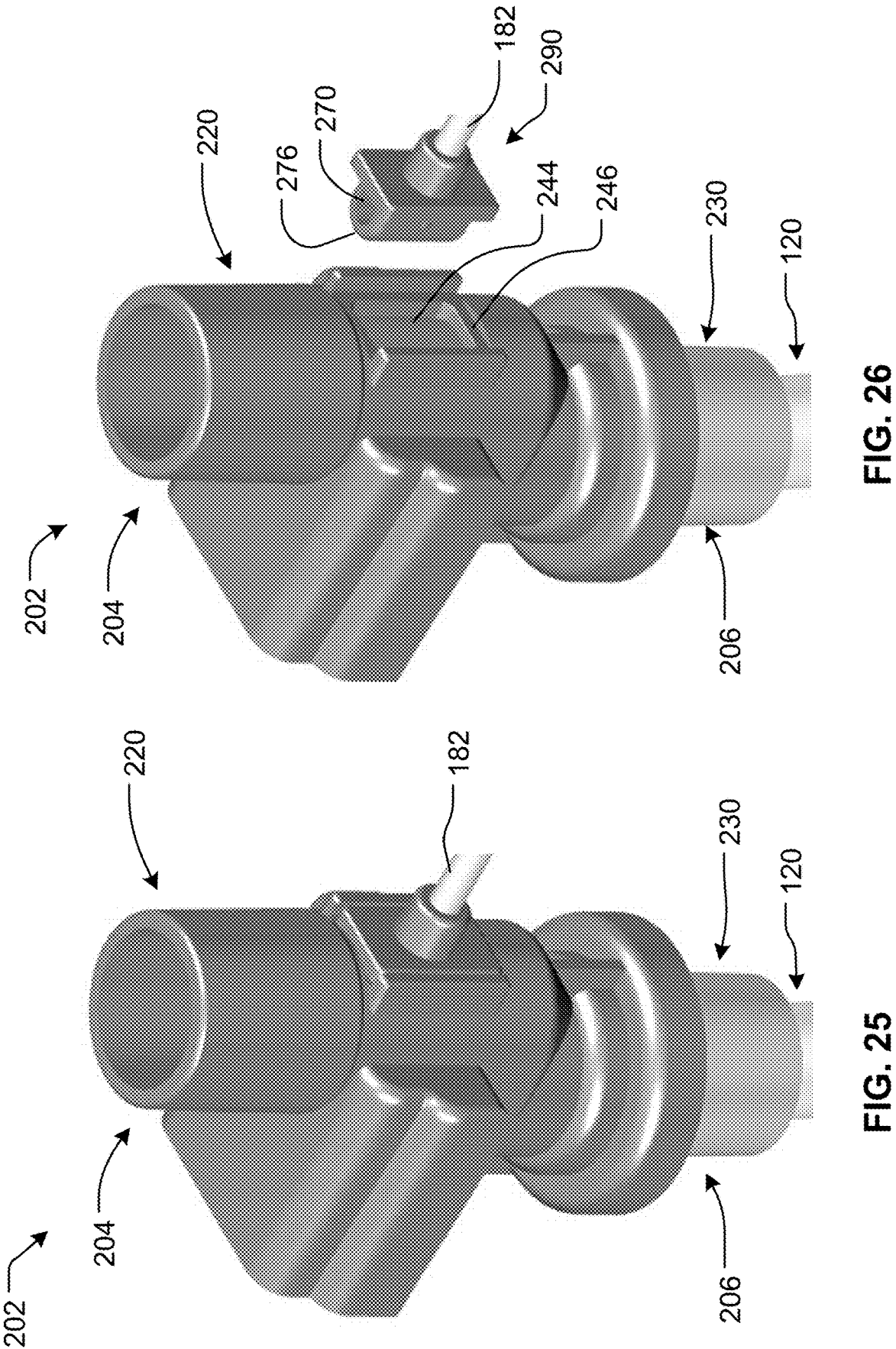
FIG. 25 is another close-up perspective view of the hub connection fitting of the ventilation tube apparatus of FIG. 17.
FIG. 26 is an exploded close-up perspective view of the hub connection fitting of the ventilation tube apparatus of FIG. 17 with a fluid sampling port fitment separated from a remainder of the hub connection fitting body.

As best shown by FIGS. 23, light-source module 304 may comprise one or more light sources 306, particularly in the form of a lamp such as one or more light-emitting diodes (LEDs). The light source 306 may be arranged as part of a light engine, which may comprise an LED driver including a printed circuit board 374 to which the LED light source 306 is mounted as well as the electrical wiring/circuitry to control and provide power/signals to the light source 306.

Light-source module 304 may further comprise a housing 378, providing a light-source housing, which forms a cavity 380 to receive the printed circuit board 374, as well as power source 330 (battery), battery holder 382 and removable non-conductive liner 384, which extends through elongated aperture 388. While not shown, light source 306 and battery holder 382 each provide conductive terminals to electrically couple light source 306 and power source 330, respectively, to printed circuit board 374 in a known manner to establish an electrical circuit there between.

As with the prior embodiments, when ventilation tube apparatus 110 is provided by the manufacturer, the power source 330 may be out of electrical communication with light source 306 to inhibit the light source 306 from powering prior to desired use. In such regard, the removable non-conductive liner 384 with a pull tab 386 may be initially positioned between the light source 306 and the power source 330 to temporarily disconnect the electrical circuit.

Thereafter, when ventilation tube apparatus 110 is to be used, the removable non-conductive liner 384 may be removed from hub connection fitting 200 by simply pulling on pull tab 386, which extends through elongated aperture 388, with a pulling force, which may remove the removable non-conductive liner 384 from hub connection fitting 200, thus establishing electrical contact between power source 330 and the printed circuit board 374 and light source 306.

As such, it should be understood that lighting apparatus 300, and more particularly light-source module 304, makes use of a switchless design with no "on-off switch." More particularly, the lighting apparatus 300 is configured for single use and will continue to operate until power from the power source 330 will no longer provide power to light the light source 306. However, it should be understood that lighting apparatus 300 may also make use of an on-off switch, which may be similar to the prior embodiments.

Once the light-source module 304 is assembled, e.g. as shown in FIGS. 22-24, it may be assembled to hub connection fitting first body 204 by being inserted into light-source module cavity/receptacle 370 formed in the hub connection fitting first body 204 by sliding light-source module 304 into light-source module cavity/receptacle 370.

In certain embodiments, after a single use of light-source module 304 and the associated power drain of power source 330 upon removal of removable non-conductive liner 384, it may be possible to detachably remove light-source module 304 from hub connection fitting body 202 by sliding the light-source module 304 out of light-source module cavity/receptacle 370. Thereafter, power source 330 and removable non-conductive liner 384 may be replaced with a new replacement power source 330 (e.g. charged battery) and a new removable non-conductive liner 384 for reuse of light-source module 304 in another (unused) ventilation tube apparatus 110.

In other embodiments, it may be desirable to inhibit removal of light-source module 304 from hub connection fitting first body 204 to deter reuse of hub connection fitting 200. In such regard, light-source module 304 and hub connection fitting first body 204 may be adhesively bonded to each other, particularly by applying an adhesive (e.g. cyanoacrylate, epoxy) to an exterior surface of the housing 378 to be in contact with the hub connection fitting first body 204 prior to inserting the light-source module 304 into light-source module cavity/receptacle 370. Thereafter, before the adhesive sets (e.g. cures and/or cools), the light-source module 304 may be slid into light-source module cavity/receptacle 370 after which time the adhesive may set. Alternatively, or in addition to the use of a separate adhesive, once the light-source module 304 is slid into light-source module cavity/receptacle 370, the housing 378 and the hub connection fitting first body 204 may be permanently welded together, such as by ultrasonic welding.

As shown, light source 306 is arranged to direct light down the longitudinal length of the ventilation tube 120 along the longitudinal axis 150, while the thickness of the printed circuit board 374 and the power source 330 are arranged transverse to the longitudinal axis 150.

In order to provide increased light emittance from the distal end 146 of the ventilation tube 120, lighting apparatus 300, and more particularly, light-emitting device 302 may further comprise a tubular light guide 400 (which is cylindrical and may also be referred to as a light tube or pipe) which extends along the length of ventilation tube 120. As shown, the proximal end 402 of the tubular light guide 400 may be adjacent (or in contact) and aligned with the light source 306 such that the light source 306 overlies the proximal end 402 of the tubular light guide 400 and is optically coupled therewith. As shown, a narrow gap 406, e.g. 0.1 mm to 3 mm, may exist between the light source 306 and the proximal end 402 of the tubular light guide 400.

Tubular light guide 400 may be formed of a bendable, light transmissive (e.g. substantially transparent) cylinder of extruded thermoplastic polymer (e.g. polycarbonate) or glass. Tubular light guide 400 may comprise a fiber optic cable having a single elongated optical fiber or a plurality of elongated optical fibers (i.e. a multi-fiber fiber optic cable). Tubular light guide 400 may be a solid cylinder, which may contain and transmit light by total internal reflection, or a hollow cylinder which may contain and transmit light along a reflective lining. As shown, tubular light guide 400 is a solid, cylindrical elongated optical fiber, particularly formed of glass, which may have a diameter in a range of 0.1 mm to 2 mm (including all ranges and increments there between) and more particularly in a range of 0.4 mm to 1.1 mm (including all ranges and increments there between).

Tubular light guide 400 is located within secondary passageway 160, which as set forth above may also be a cuff inflation passageway, to emit light at and/or adjacent the distal end opening 144 of ventilation tube 120. As shown, tubular light guide 400 is arranged in secondary passageway 260 of hub connection fitting first body 204 which is in fluid communication with secondary passageway 160 of ventilation tube 120. In the foregoing manner, air pressure to inflate the inflation cuff 62 and light to illuminate beyond the distal end 146 of the ventilation tube 120 may be extended through a single secondary passageway 160, 260 of the ventilation tube 120 and the hub connection fitting body 202, respectively.

As set forth herein, secondary passageways 160, 260 define a portion of the cuff inflation passageway in fluid communication with inflation cuff 62, as well as the cuff inflation fluid line 168 and cuff inflation port connector 176 of the cuff inflation port 170. In addition, the secondary passageway 160 of ventilation tube 120 and the secondary passageway 260 hub connection fitting first body 204 are joined by an intermediate elastically deformable tube 410 having a tube passageway 412, shown as a lumen. Tube 410 be an extruded flexible/bendable (elastically deformable and recoverable) tubing segment of extruded (thermoplastic) tubing having a constant profile along its length.

Tube 410 is used to join the secondary passageway 160 of ventilation tube 120 and the secondary passageway 260 of the hub connection fitting first body 204 particularly as the secondary passageway 160 of ventilation tube 120 and the secondary passageway 260 of the hub connection fitting first body 204 are not coaxial, and the flexibility of the tube 410 permits joining of the two laterally offset secondary passageways 160, 260.

Tube 410 is dimensioned to be inserted into the secondary passageway 160 of ventilation tube 120 and the secondary passageway 260 of hub connection fitting first body 204 such that the outer cylindrical surface of the tube 410 forms an interference (frictionally) press fit seal with the semi-circular sidewall 162 of secondary passageway 160 of ventilation tube 120, as well as the sidewall of secondary passageway 260 of hub connection fitting first body 204.

As shown, tubular light guide 400 may be disposed in the secondary passageway 160 of ventilation tube 120, the secondary passageway 260 of hub connection fitting first body 204 and the tube passageway 412 of the intermediate tube 410. As shown, tubular light guide 400 may have an outer diameter which is less than the inner diameter of secondary passageways 160, 260, as well as the tube passageway 412, to permit airflow from cuff inflation device 60 to flow along the overall passage to inflate the inflation cuff 62.

In order to seal a proximal end of the secondary passageway 260 of hub connection fitting first body 204 containing tubular light guide 400 (adjacent the proximal end 402 of the tubular light guide 400) against air leaks in the presence of air pressure to inflate inflation cuff 62, an elastically deformable flanged annular bushing 420 may be inserted into the secondary passageway 260 of hub connection fitting first body 204. The outside diameter of the annular bushing 420 may form an interference (frictionally) press fit seal with the sidewall of secondary passageway 260 of hub connection fitting first body 204, while the inner diameter of the annual bushing 420 may form an interference (frictionally) press fit seal with the cylindrical side-wall of the tubular light guide 400. The annular bushing 420 may be formed of a light transmissive polymer material such as substantially transparent silicone.

Referring to FIGS. 30A-30F, at the distal end region 143 of the ventilation tube 120, the secondary passageway 160 is sealed/occluded distal to inflation cuff inlet/outlet opening aperture 64 by a plug 430 of light transmissive (e.g. substantially transparent) polymer material. The plug 430 may be interference (frictionally) fit with the inside diameter of the semi-circular sidewall 162 as to form a fluid (air) light seal, i.e. a hermetic seal, between the plug 430 and the ventilation tube 120. The plug 430 may be formed separate from the ventilation tube 120 or formed as one-piece therewith. In the event of being formed in one piece, a distal end region 143 of the ventilation tube 120 may be heated and formed to close the secondary passageway 160 and provide the plug 430. The distal end 404 of tubular light guide 400 may terminate within secondary passageway 160 adjacent the plug 430, e.g. less than 3 mm.

If tubular light guide 400 is made of a bendable, albeit also breakable, material, such as if formed of a glass optical fiber, then it may be desirable to design the tubular light guide 400 shorter than the overall length of the secondary passageway 160 in which it resides as set forth above, and merely insert the tubular light guide 400 in secondary passageways 160 such that the tubular light guide 400 may slide freely therein. In such case, the tubular light guide 400 may not be bonded to the male connector portion 262 or semi-circular sidewall 162 of either secondary passageway 260 or 160, respectively, but be retained in the secondary passageway 260, 160 by the annular bushing 420 at the proximal end of the secondary passageway 260 and the plug 430 at the distal end of the secondary passageway 160. As a result, the tubular light guide 400 may be less opt to break when ventilation tube 120 undergoes bending. In the event it becomes desirable to bond the tubular light guide 400 to the male connector portion 262 and/or semi-circular side-wall 162 of either secondary passageway 260 or 160, respectively, the tubular light guide 400 should not be bonded at more than one fixed point, again to inhibit the likelihood of breaking when ventilation tube 120 undergoes bending.

In FIGS. 30A-30F, there are shown various embodiments of plug 430. As shown in FIG. 30A, the plug body 432 of plug 430 is recessed from the distal end 146 of the ventilation tube 120. In FIG. 30B, the plug 430 is moved distally such that the plug body 432 is located at the distal end 146 of the ventilation tube 120. In FIG. 30C, the plug body 432 may have a blind recess 434 therein to receive tubular light guide 400. If tubular light guide 400 is to be connected to the plug body 432, such may provide with an interference therewith, or a sealing/adhesive composition being placed therein. In FIG. 30D, rather than having a blind recess 434, plug body 183 may include a through-hole 436 which extends completely through plug body 432. In such regards, the distal end 404 of tubular light guide 400 may be located at the distal end 146 of the ventilation tube 120. In FIG. 30E, rather than the distal end 404 of tubular light guide 400 being recessed or at (parallel with) the distal end 146 of the ventilation tube 120, the distal end 404 of tubular light guide 400 may extend beyond the distal end 146 of the ventilation tube 120 (e.g. by 1 mm or less). In FIG. 30F, in another embodiment, the ventilation tube 120 is shown to have a plurality of tubular light guides 400, with the tubular light guide 400 on the left having a plug 430 adjacent the distal end 404 thereof, and the tubular light guide 400 on the right not having a plug 430. Both tubular light guides 400 may be used to emit light.

Referring to FIG. 31, prior to the connector 186 (which connects port 180 to the analyzing/monitoring apparatus 30 or the drug delivery device 50), the fluid line 178 may include two tubes 182 connectable and disconnectable by mating first and second mating connectors 188a, 188b (e.g. Luer connectors).

First connector 188a may more particularly include a valve 190 which opens when the first and second connectors 188a, 188b are connected to allow exhaled gas(es) from the patient to travel within the tube 182 towards analyzing/monitoring apparatus 30, or which opens which opens when the first and second connectors 188a, 188b are connected to allow a drug to be delivered from drug delivery device 50 to travel within the tube 182 to the patient. First connector 188a closes the valve 190 and passageway 184 in the event of disconnection from second connector 188b. Upon disconnection from second connector 188b, first connector 188a closes the valve 190 to inhibit a pressure loss within the medical system 10.

An exemplary valve 190 within first connector 188a is shown in FIGS. 32A-32B. As shown, valve 190 comprises a plug 194 (shown as a spherical ball) which is biased to the closed position by bias member 192 (shown as a helically wound compression spring). When second connector 188b (or a drug delivery device 30 such as syringe 70 as shown) is connected to first connector 188a, the second connector 188b (or the syringe 70) has a prong which contacts and retracts the plug 194 against the bias force of the bias member 192 to open the passageway 184 as shown in FIG. 32B.

Another exemplary valve 190 is shown in FIGS. 32C-32D. Valve 190 may be provided by a two-way (rotatable) stopcock valve 196, in which case the first and second connectors 188a, 188b with the valve may be eliminated. As shown in FIG. 32C, the stopcock valve 196 is closed such that the passageway 184 is closed. and in FIG. 32D the stopcock valve 196 is open (rotated 90 degrees) such that the passageway 184 is open.

During use of port 180 particularly as a fluid sampling port, in the event passageway 184 prior to first connector 188a becomes clogged with mucus, saliva or other secretions, the first and second connectors 188a, 188b may be disconnected from one another without a change in pressure (positive or negative) within ventilation passageway 250. Thereafter, a syringe 70 may be connected to first connector 188*a* to reopen the valve and inject air into passageway 184 to remove the secretions therein by forcing them back to the ventilation passageway 250. Thereafter, the syringe 70 may be disconnected from first connector 188*a*, and first connector 188*a* may be reconnected with second connector 188*b*. Alternatively, where the first and second connectors 188*a*, 188*b* are eliminated, syringe 70 may be connected to tube 182 downstream of the stopcock valve 196 (i.e. between the stopcock valve 196 and analyzing/monitoring apparatus 30), such as to connector 186.

Referring now to FIGS. 33-40, there is shown another embodiment of a medical device 100 of a medical system 10 according to the present disclosure. More particularly, medical device 100 comprises an airway management medical device, particularly a ventilation tube apparatus 110 in a form of an endotracheal tube apparatus.

As shown, the port 180 comprises an injection molded (plastic), T-shaped, fluid sampling port fitment 500. Fluid sampling port fitment 500 may be substantially transparent and formed of a rigid thermoplastic such as acrylic (polymethyl methacrylate) or polycarbonate. Fluid sampling port fitment 500 may also be formed of polypropylene, polyethylene, polyamide or polyacetal.

The fluid sampling port fitment 500 of the port 180 is movable, and more particularly slidable, relative to, and more particularly within, the hub connection fitting body 202. More particularly, the fluid sampling port fitment 500 of the 180 is linearly, translationally and transversely movable relative to the hub connection fitting body 202, as well as the longitudinal axis 150 (shown as the center axis) of ventilation passageway formed by passageways 22, 134 and 250.

Even more particularly, the fluid sampling port fitment 500 of the port 180 is movable from a central/medial region of the ventilation passageway 250 to a lateral region of the ventilation passageway 250 where the lateral region is further from the longitudinal axis 150 than the central/medial region. In this manner, when the fluid sampling port fitment 500 of the port 180 is moved laterally during intubation, the ventilation passageway 250 is better opened for passage of an elongated medical instrument 80 to be disposed within the ventilation passageway 250 for patient/host treatment, such as a ventilation (endotracheal) tube (insertion and/or extraction) guide 82, e.g. introducer, bougie, stylet (see e.g., FIG. 38), to assist with intubation. Elongated medical instrument 80, and more particularly ventilation tube guide 82, may be understood as part of the medical device 100, and may be provided as part of a medical device kit with ventilation tube apparatus 110.

As shown, the fluid sampling port fitment 500 forms a T-shaped secondary passageway 510, comprising a longitudinal passageway 512 and a transverse passageway 514. Longitudinal passageway 512 extends along, and more particularly parallel to, the longitudinal axis 150. Longitudinal passageway 512 is open at opposing ends to ventilation passageway 250 and is bisected by transverse passageway 514. The transverse passageway 514 is transverse, and more particularly perpendicular, to the longitudinal axis 150 and the longitudinally passageway 512.

The longitudinal passageway 512 is formed by a longitudinal, circular (cylindrical) annular tubular wall 522 and the transverse passageway 514 is formed by a transverse, circular (cylindrical), annular tubular wall 524. The transverse tubular wall 524 extends through a cylindrical cavity 530 formed by cylindrical bore 532 and cylindrical counter-bore 534. In certain embodiments, half of the longitudinal tubular wall 522 and longitudinal passageway 512 may be completely eliminated, in which case the fluid sampling port fitment 500 is L-shaped. In other certain embodiments, the longitudinal tubular wall 522 and longitudinal passageway 512 may be completely eliminated, leaving only the transverse tubular wall 524 and transverse passageway 514.

The outer end face 536 of the transverse tubular wall 524 is permanently joined, and more particularly butt welded, to an end face of the tube 182, particularly such that transverse passageway 514 and tube passageway 184 are aligned for transmission of exhaled sample gases from ventilation passageway 250 to analyzing/monitoring apparatus 30.

Within cylindrical counter-bore 534 is further disposed a circular flange 526 of the transverse tubular wall 524, a bias member 540 (in a form of a cylindrical coil (helical) compression spring which is wound around the transverse tubular wall 524), an O-ring annular gasket 550 and an annular closure cover 560. The gasket 550 inhibits fluid leakage from the ventilation passageway 250. The closure cover 560 closes the cylindrical counter-bore 534. The closure cover 560 also provided a reaction surface/support for the bias member 540 to compress against, as does the circular flange 526, as explained in greater detail below.

Adjacent the outer face of closure cover 560, a rotatable knob 570 is mechanically rotatably fastened to transverse tubular wall 524 by a snap-fit connection. As shown, rotatable knob 570 has a rectangular knob body 572 having a centrally disposed cylindrical through-hole 574 with an undercut recess 576, which extends around a circumference of the through-hole 574. As shown, the undercut recess 576 of the rotatable knob 570 is occupied by semi-circular rib 528 which extends around the circumference of transverse tubular wall 524 of fluid sampling port fitment 500. In this manner, the rotatable knob 570 and the transverse tubular wall 524 are mechanically fastened against separation along the longitudinal axis of the transverse tubular wall 524, but the rotatable knob 570 is still rotatable around the transverse tubular wall 524.

As shown in FIGS. 35-37, the rotatable knob 570, and more particularly the rectangular knob body 572, is disposed between two parallel stand-offs 580 formed in the hub connection fitting body 202. disposed on opposite sides of the rectangular knob body 572. Also as shown the fluid sampling port fitment 500 is in a first position disposed in the center of the ventilation passageway 250.

During operation, the rotatable knob 570 may be grasped and pulled transverse to the longitudinal axis 150, against the bias (force) of the bias member 540 which elastically compresses. In this manner, as shown in FIGS. 38-40, the fluid sampling port fitment 500 is moved away from a central/medial region of the ventilation passageway 250 to a lateral region of the ventilation passageway 250 where the lateral region is further from the longitudinal axis 150 than the central/medial region. In this manner, when the fluid sampling port fitment 500 is moved laterally with translational motion to a second position during intubation, the ventilation passageway 250 is better opened for passage of the elongated medical instrument 80 (see e.g., FIG. 38) to assist with intubation.

The fluid sampling port fitment 500 of the port 180 may then be locked in the second position by rotating the rotatable knob 570 ninety degrees (90°) at which time the rectangular knob body 572 of the rotatable knob 570 will overlie and be supported on/by the stand-offs 580 against the bias the bias member. The rectangular knob body 572 is rotatable independent of the fluid sampling port fitment 500 and tube 182. At this time, rotatable knob 570 may be released without the fluid sampling port fitment 500 moving back to the central/medial region of the ventilation passageway 250.

Thereafter, once the ventilation tube 120 is properly positioned and the elongated medical instrument 80 withdrawn, the port 180 may then be unlocked from the second position by rotating the rotatable knob 570 ninety degrees (90°) at which time the rectangular knob body 572 of the rotatable knob 570 will fit between the stand-offs 580 and releasing the rotatable knob 570. The bias member 540 will then decompress and move the fluid sampling port fitment 500 back to the central/medial region of the ventilation passageway 250 closer to the longitudinal axis 150.

In another embodiment, as shown in FIG. 41, in the second position, the fluid sampling port fitment 500 may be at least partially or more preferably completely, disposed in a recess 590 formed in the hub connection fitting body 202, such that it may not occlude the ventilation passageway 250 at least partially or completely. As shown, the fluid sampling port fitment 500 is substantially flush (e.g. within 0.1 mm), and more particularly flush (i.e. in the same plane), with the sidewall 252 of the ventilation passage 250, formed by the hub connection fitting body 202.

In such regards, the ventilation passageway 250 is completely opened for passage of the elongated medical instrument 80 to assist with intubation without any occlusion by the fluid sampling port fitment 500.

In another embodiment, as shown in FIGS. 42-46, the port 180 comprises a fluid sampling port fitment 598. The fluid sampling port fitment 598 may comprise, essentially consist of, or consist of a tube 600. Tube 600 may be an extruded flexible/bendable (elastically deformable and recoverable) tubing segment of extruded (thermoplastic) tubing having a constant profile along its length. Exemplary thermoplastic polymer compositions for tube 600 may include plasticized polyvinyl chloride, polyolefins (e.g. polypropylene, polyethylene) and thermoplastic elastomers. Alternatively, or in addition to, the tube 600 may be formed of a polymer composition having a Shore A durometer hardness, as measured by ASTM D2240-15 (2021), in a range of 40-95 Shore A durometer hardness, and more particularly in the range of 50-90 Shore A durometer hardness.

As shown in FIG. 42, in a first position, a longitudinal axis 610 of the tube 600 is substantially transverse (e.g. within 20 degrees of being perpendicular), and more particularly perpendicular (orthogonal), to the longitudinal axis 150 of the ventilation passageway 250. As shown, tube 600 has a tube annular wall 602, shown to be circular and cylindrical, defining a tube passageway 604, provided by a center lumen of the tube 600. The tube annular wall 602 may be connected to the hub connection fitting body 202 within cylindrical bore 532 as to be fixed stationary (inseparable) therewith and form a hermetic seal therebetween, particularly by any combination of interference fit, adhesive bond and welding (e.g. ultrasonically welded) to the hub connection fitting body 202 within cylindrical bore 532. The tube 600 may have an outer diameter 606 in a range of 0.50 mm to 3 mm (including all ranges and increments there between), and more particularly in a range of 0.60 mm to 2 mm (including all ranges and increments there between), and more particularly 1 mm to 1.5 mm (including all ranges and increments there between). The tube 600 may have an inner diameter 608 (the diameter of tube passageway 604) in a range of 0.25 mm to 2 mm (including all ranges and increments there between), and more particularly 0.35 mm to 1.5 mm, and more particularly 0.5 mm to 1 mm (including all ranges and increments there between). The distal end (terminal) face 616 of the tube 600 includes a distal end (single) sample inlet (opening) 620 to tube passageway 604.

As shown in FIG. 42, the tube 600 having a first position, extends through the cylindrical bore 532 formed in the hub connection fitting 200, particularly disposed in hub connection fitting body 202, and into ventilation passageway 250 from the sidewall 252 which defines the ventilation passage 250, particularly linearly in a transverse plane 614 which is perpendicular to the longitudinal axis 150.

As best shown in FIG. 43, the ventilation passageway 250 has a cross-sectional dimension 256 (which may also be referred to as a cross dimension) perpendicular to the longitudinal axis 150, shown parallel with the longitudinal axis 610 of the tube 600, which may be understood as being equal to a diameter of the ventilation passageway 250. More particularly, as shown, the cross-sectional dimension 256 of the ventilation passageway 250 may be in the same transverse plane 614 as the tube 600 within the ventilation passageway 250, and particularly the longitudinal axis 610 thereof.

In various embodiments, the tube 600, and more particularly the distal end sample inlet (opening) 620, may particularly extend into the ventilation passageway 250 at a distance in a range of 5% to 95% of the cross-sectional dimension 256 (including all ranges and increments there between); 5% to 90% of the cross-sectional dimension 256 (including all ranges and increments there between); 5% to 85% of the cross-sectional dimension 256 (including all ranges and increments there between); 5% to 80% of the cross-sectional dimension 256 (including all ranges and increments there between); 5% to 75% of the cross-sectional dimension 256 (including all ranges and increments there between); 5% to 70% of the cross-sectional dimension 256 (including all ranges and increments there between); 5% to 65% of the cross-sectional dimension 256 (including all ranges and increments there between); 5% to 60% of the cross-sectional dimension 256 (including all ranges and increments there between); 5% to 55% of the cross-sectional dimension 256 (including all ranges and increments there between); 10% to 95% of the cross-sectional dimension 256 (including all ranges and increments there between); 10% to 90% of the cross-sectional dimension 256 (including all ranges and increments there between); 10% to 85% of the cross-sectional dimension 256 (including all ranges and increments there between); 10% to 80% of the cross-sectional dimension 256 (including all ranges and increments there between); 10% to 75% of the cross-sectional dimension 256 (including all ranges and increments there between); 10% to 70% of the cross-sectional dimension 256 (including all ranges and increments there between); 10% to 65% of the cross-sectional dimension 256 (including all ranges and increments there between); 10% to 60% of the cross-sectional dimension 256 (including all ranges and increments there between); 10% to 55% of the cross-sectional dimension 256 (including all ranges and increments there between); 15% to 95% of the cross-sectional dimension 256 (including all ranges and increments there between); 15% to 90% of the cross-sectional dimension 256 (including all ranges and increments there between); 15% to 85% of the cross-sectional dimension 256 (including all ranges and increments there between); 15% to 80% of the cross-sectional dimension 256 (including all ranges and increments there between); 15% to 75% of the cross-sectional dimension 256 (including all ranges and increments there between); 15% to 70% of the cross-sectional dimension 256 (including all ranges and increments there between); 15% to 65% of the cross-sectional dimension 256 (including all ranges and increments there between); 15% to 60% of the cross-sectional dimension 256 (including all ranges and increments there between); 15% to 55% of the cross-sectional dimension 256 (including all ranges and increments there between); 20% to 95% of the cross-sectional dimension 256 (including all ranges and increments there between); 20% to 90% of the cross-sectional dimension 256 (including all ranges and increments there between); 20% to 85% of the cross-sectional dimension 256 (including all ranges and increments there between); 20% to 80% of the cross-sectional dimension 256 (including all ranges and increments there between); 20% to 75% of the cross-sectional dimension 256 (including all ranges and increments there between); 20% to 70% of the cross-sectional dimension 256 (including all ranges and increments there between); 20% to 65% of the cross-sectional dimension 256 (including all ranges and increments there between); 20% to 60% of the cross-sectional dimension 256 (including all ranges and increments there between); 20% to 55% of the cross-sectional dimension 256 (including all ranges and increments there between); 25% to 95% of the cross-sectional dimension 256 (including all ranges and increments there between); 25% to 90% of the cross-sectional dimension 256 (including all ranges and increments there between); 25% to 85% of the cross-sectional dimension 256 (including all ranges and increments there between); 25% to 80% of the cross-sectional dimension 256 (including all ranges and increments there between); 25% to 75% of the cross-sectional dimension 256 (including all ranges and increments there between); 25% to 70% of the cross-sectional dimension 256 (including all ranges and increments there between); 25% to 65% of the cross-sectional dimension 256 (including all ranges and increments there between); 25% to 60% of the cross-sectional dimension 256 (including all ranges and increments there between); 25% to 55% of the cross-sectional dimension 256 (including all ranges and increments there between); 30% to 95% of the cross-sectional dimension 256 (including all ranges and increments there between); 30% to 90% of the cross-sectional dimension 256 (including all ranges and increments there between); 30% to 85% of the cross-sectional dimension 256 (including all ranges and increments there between); 30% to 80% of the cross-sectional dimension 256 (including all ranges and increments there between); 30% to 75% of the cross-sectional dimension 256 (including all ranges and increments there between); 30 to 70% of the cross-sectional dimension 256 (including all ranges and increments there between); 30% to 65% of the cross-sectional dimension 256 (including all ranges and increments there between); 30% to 60% of the cross-sectional dimension 256 (including all ranges and increments there between); 30% to 55% of the cross-sectional dimension 256 (including all ranges and increments there between); 35% to 95% of the cross-sectional dimension 256 (including all ranges and increments there between) 35% to 90% of the cross-sectional dimension 256 (including all ranges and increments there between); 35% to 85% of the cross-sectional dimension 256 (including all ranges and increments there between); 35% to 80% of the cross-sectional dimension 256 (including all ranges and increments there between); 35% to 75% of the cross-sectional dimension 256 (including all ranges and increments there between); 35% to 70% of the cross-sectional dimension 256 (including all ranges and increments there between); 35% to 65% of the cross-sectional dimension 256 (including all ranges and increments there between); 35% to 60% of the cross-sectional dimension 256 (including all ranges and increments there between); 35% to 55% of the cross-sectional dimension 256 (including all ranges and increments there between); 40% to 95% of the cross-sectional dimension 256 (including all ranges and increments there between); 40% to 90% of the cross-sectional dimension 256 (including all ranges and increments there between); 40% to 85% of the cross-sectional dimension 256 (including all ranges and increments there between); 40% to 80% of the cross-sectional dimension 256 (including all ranges and increments there between); 40% to 75% of the cross-sectional dimension 256 (including all ranges and increments there between); 40% to 70% of the cross-sectional dimension 256 (including all ranges and increments there between); 40% to 65% of the cross-sectional dimension 256 (including all ranges and increments there between); 40% to 60% of the cross-sectional dimension 256 (including all ranges and increments there between); 40% to 55% of the cross-sectional dimension 256 (including all ranges and increments there between); 45% to 95% of the cross-sectional dimension 256 (including all ranges and increments there between); 45% to 90% of the cross-sectional dimension 256 (including all ranges and increments there between); 45% to 85% of the cross-sectional dimension 256 (including all ranges and increments there between); 45% to 80% of the cross-sectional dimension 256 (including all ranges and increments there between); 45% to 75% of the cross-sectional dimension 256 (including all ranges and increments there between); 45% to 70% of the cross-sectional dimension 256 (including all ranges and increments there between); 45% to 65% of the cross-sectional dimension 256 (including all ranges and increments there between); 45% to 60% of the cross-sectional dimension 256 (including all ranges and increments there between); and 45% to 55% of the cross-sectional dimension 256 (including all ranges and increments there between). Other percentages may include, alone or in any combination, 5% or more (which may also be set forth as at least 5%), 10% or more; 15% or more; 20% or more; 25% or more; 30% or more; 35% or more; 40% or more; 45% or more; 50% or more; 55% or more; 60% or more; 65% or more; 70% or more; 75% or more; 80% or more; 85% or more; 90% or more; 95% or more; as well as 95% or less (which may also be set forth as at most 95%); 90% or less; 85% or less; 80% or less; 75% or less; 70% or less; 65% or less; 60% or less; 55% or less; 50% or less; 45% or less; 40% or less; 35% or less; 30% or less; 25% or less; 20% or less; 15% or less; 10% or less; and 5% or less. As shown, the tube 600, as well as the distal end sample inlet (opening) 620 extends into the ventilation passageway 250 at a distance of 50% of the cross-sectional dimension 256.

With regards to particular dimension, tube 600, and more particularly the distal end sample inlet (opening) 620, may extend into the ventilation passageway 250 at a lateral distance 612 (which may also be referred to as a cross-distance or transverse distance) in a range of 0.5 mm to 8 mm (including all ranges and increments there between); 0.5 mm to 7 mm (including all ranges and increments there between); 0.5 mm to 6 mm (including all ranges and increments there between); 0.5 mm to 5 mm (including all ranges and increments there between); 0.5 mm to 4 mm (including all ranges and increments there between); 0.5 mm to 3 mm (including all ranges and increments there between); 0.5 mm to 2 mm (including all ranges and increments there between); 0.5 mm to 1 mm (including all ranges and increments there between); 1 mm to 8 mm (including all ranges and increments there between); 1 mm to 7 mm (including all ranges and increments there between); 1 mm to 6 mm (including all ranges and increments there between); 1 mm to 5 mm (including all ranges and increments there between); 1 mm to 4 mm (including all ranges and increments there between); 1 mm to 3 mm (including all ranges and increments there between); 1 mm to 2 mm (including all ranges and increments there between); 2 mm to 8 mm (including all ranges and increments there between); 2 mm to 7 mm (including all ranges and increments there between); 2 mm to 6 mm (including all ranges and increments there between); 2 mm to 5 mm (including all ranges and increments there between); 2 mm to 4 mm (including all ranges and increments there between); 2 mm to 3 mm (including all ranges and increments there between); 3 mm to 8 mm (including all ranges and increments there between); 3 mm to 7 mm (including all ranges and increments there between); 3 mm to 6 mm (including all ranges and increments there between); 3 mm to 5 mm (including all ranges and increments there between); and 3 mm to 4 mm (including all ranges and increments there between). Other dimensions may include, alone or in any combination, 0.5 mm or more (which may also be set forth as at least 0.5 mm), 1 mm or more; 2 mm or more; 3 mm or more; 4 mm or more, 5 mm or more, 6 mm or more; 7 mm or more; and 8 mm or more; 9 mm or more; 10 mm or more; as well as 10 mm or less (which may also be set forth as at most 10 mm); 9 mm or less, 8 mm or less, 7 mm or less, 6 mm or less, 5 mm or less, 4 mm or less, 3 mm or less, 2 mm or less; and 1 mm or less. The preferred lateral distance 612 will vary with the size of the medical device 100, e.g. adult or pediatric. In still other embodiments, the end (terminal) face 616 of the tube 600 may not be disposed in the ventilation passageway 250, but rather be substantially flush (e.g. within 0.1 mm of being flush, protruding or recessed) or more preferably flush (i.e. in the same plane) with the sidewall 252 of the ventilation passageway 250.

As shown in FIG. 43, the total cross-sectional area 254 of the ventilation passageway 250 in the transverse plane 614 may be divided into an inner cross-sectional area region 254*a* and an outer cross-sectional area region 254*b*. As shown, distal end sample inlet (opening) 620 is disposed in the inner cross-sectional area region 254*a*, which is completely surrounded the outer cross-sectional area region 254*b* in a form of an (annular or 360 degree) enclosed ring. In such regards, the inner cross-sectional area region 254*a* is spaced from, and not defined by, the sidewall 252. As a result, the distal end sample inlet (opening) 620 is less apt to be influenced by turbulent airflow effects which may occur in the ventilation passageway 250 arising from the sidewall 252. Furthermore, the airflow through the center of the ventilation passageway 250 may be understood to flow faster than the airflow closer to the sidewall 252 due to drag effects resulting from the sidewall 252.

In certain embodiments, the inner cross-sectional area region 254*a* may be in a range of 5% to 95% of the total cross-sectional area 254 (including all ranges and increments there between); 5% to 90% of the total cross-sectional area 254 (including all ranges and increments there between); 5% to 85% of the total cross-sectional area 254 (including all ranges and increments there between); 5% to 80% of the total cross-sectional area 254 (including all ranges and increments there between); 5% to 75% of the total cross-sectional area 254 (including all ranges and increments there between); 5% to 70% of the total cross-sectional area 254 (including all ranges and increments there between); 5% to 65% of the total cross-sectional area 254

(including all ranges and increments there between); 5% to 60% of the total cross-sectional area 254 (including all ranges and increments there between); 5% to 55% of the total cross-sectional area 254 (including all ranges and increments there between); 5% to 50% of the total cross-sectional area 254 (including all ranges and increments there between); 5% to 45% of the total cross-sectional area 254 (including all ranges and increments there between); 5% to 40% of the total cross-sectional area 254 (including all ranges and increments there between); 5% to 35% of the total cross-sectional area 254 (including all ranges and increments there between); 5% to 30% of the total cross-sectional area 254 (including all ranges and increments there between); 5% to 25% of the total cross-sectional area 254 (including all ranges and increments there between); and 5% to 20% of the total cross-sectional area 254 (including all ranges and increments there between).

In certain embodiments, the inner cross-sectional area region 254*a* may be in a range of 10% to 95% of the total cross-sectional area 254 (including all ranges and increments there between); 10% to 90% of the total cross-sectional area 254 (including all ranges and increments there between); 10% to 85% of the total cross-sectional area 254 (including all ranges and increments there between); 10% to 80% of the total cross-sectional area 254 (including all ranges and increments there between); 10% to 75% of the total cross-sectional area 254 (including all ranges and increments there between); 10% to 70% of the total cross-sectional area 254 (including all ranges and increments there between); 10% to 65% of the total cross-sectional area 254 (including all ranges and increments there between); 10% to 60% of the total cross-sectional area 254 (including all ranges and increments there between); 10% to 55% of the total cross-sectional area 254 (including all ranges and increments there between); 10% to 50% of the total cross-sectional area 254 (including all ranges and increments there between); 10% to 45% of the total cross-sectional area 254 (including all ranges and increments there between); 10% to 40% of the total cross-sectional area 254 (including all ranges and increments there between); 10% to 35% of the total cross-sectional area 254 (including all ranges and increments there between); 10% to 30% of the total cross-sectional area 254 (including all ranges and increments there between); 10% to 25% of the total cross-sectional area 254 (including all ranges and increments there between); and 10% to 20% of the total cross-sectional area 254 (including all ranges and increments there between).

In certain embodiments, the inner cross-sectional area region 254*a* may be in a range of 15% to 95% of the total cross-sectional area 254 (including all ranges and increments there between); 15% to 90% of the total cross-sectional area 254 (including all ranges and increments there between); 15% to 85% of the total cross-sectional area 254 (including all ranges and increments there between); 15% to 80% of the total cross-sectional area 254 (including all ranges and increments there between); 15% to 75% of the total cross-sectional area 254 (including all ranges and increments there between); 15% to 70% of the total cross-sectional area 254 (including all ranges and increments there between); 15% to 65% of the total cross-sectional area 254 (including all ranges and increments there between); 15% to 60% of the total cross-sectional area 254 (including all ranges and increments there between); 15% to 55% of the total cross-sectional area 254 (including all ranges and increments there between); 15% to 50% of the total cross-sectional area 254 (including all ranges and increments there between); 15% to 45% of the total cross-sectional area 254

(including all ranges and increments there between); 15% to 40% of the total cross-sectional area 254 (including all ranges and increments there between); 15% to 35% of the total cross-sectional area 254 (including all ranges and increments there between); 15% to 30% of the total cross-sectional area 254 (including all ranges and increments there between); 15% to 25% of the total cross-sectional area 254 (including all ranges and increments there between); and 15% to 20% of the total cross-sectional area 254 (including all ranges and increments there between).

In certain embodiments, the inner cross-sectional area region 254a may be in a range of 20% to 95% of the total cross-sectional area 254 (including all ranges and increments there between); 20% to 90% of the total cross-sectional area 254 (including all ranges and increments there between); 20% to 85% of the total cross-sectional area 254 (including all ranges and increments there between); 20% to 80% of the total cross-sectional area 254 (including all ranges and increments there between); 20% to 75% of the total cross-sectional area 254 (including all ranges and increments there between); 20% to 70% of the total cross-sectional area 254 (including all ranges and increments there between); 20% to 65% of the total cross-sectional area 254 (including all ranges and increments there between); 20% to 60% of the total cross-sectional area 254 (including all ranges and increments there between); 20% to 55% of the total cross-sectional area 254 (including all ranges and increments there between); 20% to 50% of the total cross-sectional area 254 (including all ranges and increments there between); 20% to 45% of the total cross-sectional area 254 (including all ranges and increments there between); 20% to 40% of the total cross-sectional area 254 (including all ranges and increments there between); 20% to 35% of the total cross-sectional area 254 (including all ranges and increments there between); 20% to 30% of the total cross-sectional area 254 (including all ranges and increments there between); and 20% to 25% of the total cross-sectional area 254 (including all ranges and increments there between).

In certain embodiments, the inner cross-sectional area region 254a may be in a range of 25% to 95% of the total cross-sectional area 254 (including all ranges and increments there between); 25% to 90% of the total cross-sectional area 254 (including all ranges and increments there between); 25% to 85% of the total cross-sectional area 254 (including all ranges and increments there between); 25% to 80% of the total cross-sectional area 254 (including all ranges and increments there between); 25% to 75% of the total cross-sectional area 254 (including all ranges and increments there between); 25% to 70% of the total cross-sectional area 254 (including all ranges and increments there between); 25% to 65% of the total cross-sectional area 254 (including all ranges and increments there between); 25% to 60% of the total cross-sectional area 254 (including all ranges and increments there between); 25% to 55% of the total cross-sectional area 254 (including all ranges and increments there between); 25% to 50% of the total cross-sectional area 254 (including all ranges and increments there between); 25% to 45% of the total cross-sectional area 254 (including all ranges and increments there between); 25% to 40% of the total cross-sectional area 254 (including all ranges and increments there between); 25% to 35% of the total cross-sectional area 254 (including all ranges and increments there between); and 25% to 30% of the total cross-sectional area 254 (including all ranges and increments there between).

In certain embodiments, the inner cross-sectional area region 254a may be in a range of 30% to 95% of the total cross-sectional area 254 (including all ranges and increments there between); 30% to 90% of the total cross-sectional area 254 (including all ranges and increments there between); 30% to 85% of the total cross-sectional area 254 (including all ranges and increments there between); 30% to 80% of the total cross-sectional area 254 (including all ranges and increments there between); 30% to 75% of the total cross-sectional area 254 (including all ranges and increments there between); 30% to 70% of the total cross-sectional area 254 (including all ranges and increments there between); 30% to 65% of the total cross-sectional area 254 (including all ranges and increments there between); 30% to 60% of the total cross-sectional area 254 (including all ranges and increments there between); 30% to 55% of the total cross-sectional area 254 (including all ranges and increments there between); 30% to 50% of the total cross-sectional area 254 (including all ranges and increments there between); 30% to 45% of the total cross-sectional area 254 (including all ranges and increments there between); 30% to 40% of the total cross-sectional area 254 (including all ranges and increments there between); and 30% to 35% of the total cross-sectional area 254 (including all ranges and increments there between).

In certain embodiments, the inner cross-sectional area region 254a may be in a range of 35% to 95% of the total cross-sectional area 254 (including all ranges and increments there between); 35% to 90% of the total cross-sectional area 254 (including all ranges and increments there between); 35% to 85% of the total cross-sectional area 254 (including all ranges and increments there between); 35% to 80% of the total cross-sectional area 254 (including all ranges and increments there between); 35% to 75% of the total cross-sectional area 254 (including all ranges and increments there between); 35% to 70% of the total cross-sectional area 254 (including all ranges and increments there between); 35% to 65% of the total cross-sectional area 254 (including all ranges and increments there between); 35% to 60% of the total cross-sectional area 254 (including all ranges and increments there between); 35% to 55% of the total cross-sectional area 254 (including all ranges and increments there between); 35% to 50% of the total cross-sectional area 254 (including all ranges and increments there between); 35% to 45% of the total cross-sectional area 254 (including all ranges and increments there between); and 35% to 40% of the total cross-sectional area 254 (including all ranges and increments there between).

In certain embodiments, the inner cross-sectional area region 254a may be in a range of 40% to 95% of the total cross-sectional area 254 (including all ranges and increments there between); 40% to 90% of the total cross-sectional area 254 (including all ranges and increments there between); 40% to 85% of the total cross-sectional area 254 (including all ranges and increments there between); 40% to 80% of the total cross-sectional area 254 (including all ranges and increments there between); 40% to 75% of the total cross-sectional area 254 (including all ranges and increments there between); 40% to 70% of the total cross-sectional area 254 (including all ranges and increments there between); 40% to 65% of the total cross-sectional area 254 (including all ranges and increments there between); 40% to 60% of the total cross-sectional area 254 (including all ranges and increments there between); 40% to 55% of the total cross-sectional area 254 (including all ranges and increments there between); 40% to 50% of the total cross-sectional area 254 (including all ranges and increments there between); and 40% to 45% of the total cross-sectional area 254 (including all ranges and increments there between).

Other percentages may include, alone or in any combination, 5% or more (which may also be set forth as at least 5%), 10% or more; 15% or more; 20% or more; 25% or more; 30% or more; 35% or more; 40% or more; 45% or more; 50% or more; 55% or more; 60% or more; 65% or more; 70% or more; 75% or more; 80% or more; 85% or more; 90% or more; 95% or more; as well as 95% or less (which may also be set forth as at most 95%); 90% or less; 85% or less; 80% or less; 75% or less; 70% or less; 65% or less; 60% or less; 55% or less; 50% or less; 45% or less; 40% or less; 35% or less; 30% or less; 25% or less; 20% or less; 15% or less; 10% or less; and 55% or less.

As shown by FIGS. 44-46, rather than the fluid sampling port fitment 598 being movable laterally out of the way of the elongated medical instrument 80 (e.g. ventilation tube guide 82) by translational motion (relative to the hub connection fitting body 202) as with the embodiments of FIGS. 33-41, the fluid sampling port fitment 598 of the embodiment of FIGS. 42-46 moves laterally from a first position (FIG. 42) to a second position disposed laterally of the first position (FIG. 44) with deformation (from bending motion), and more particularly elastic deformation of the tube 600 (relative to the hub connection fitting body 202), particularly in response to contact or otherwise being acted upon (e.g. by being pushed), by the elongated medical instrument 80 being inserted down the ventilation passageway 250, particularly the center, from the proximal end of the ventilation tube apparatus 110 towards the distal end of the ventilation tube apparatus 110.

Upon the elongated medical instrument 80 contacting the tube 600, the tube 600 sufficiently elastically deforms relative to the elongated medical instrument 80, particularly away from, and more particularly, out of, the insertion path of the elongated medical instrument 80 in response to the elongated medical instrument 80 contacting therewith, to provide clearance for the elongated medical instrument 80 and enable the elongated medical instrument 80 to extend past the tube 600, such that the tube 600 does not fracture or otherwise break in response to the passing of the elongated medical instrument 80 past the tube 600. Once past the tube 600, the elongated medical instrument 80 is inserted down the ventilation passageway 134 of the ventilation tube 120, and extended from the distal end 146 of the ventilation tube120.

Thereafter, once the ventilation tube apparatus 110 is properly positioned in the airway of the patient/host, the elongated medical instrument 80 is withdrawn from the ventilation tube apparatus 110. As the elongated medical instrument 80 is being withdrawn and through the hub connection fitting 200, or otherwise out of contact with the tube 600 during or thereafter, the tube 600 elastically recovers and transitions towards the first position, which may include substantially towards the first position within one (1) hour; and more particularly within thirty (30) minutes; and more particularly within fifteen (15) minutes, and more particularly within five (5) minutes, and more particularly within two (2) minutes, and more particularly within one (1) minute after removal/elimination of contact of the elongated medical instrument 80 therewith (e.g. at least 20% of the distance back/recovery to the first position and more particularly at least 30% of the distance back/recovery to the first position and more particularly at least 40% of the distance back/recovery to the first position and more particularly at least 50% of the distance back/recovery to the first position and more particularly at least 60% of the distance back/recovery to the first position and more particularly at least 70% of the distance back/recovery to the first position and more particularly at least 80% of the distance back/recovery to the first position and more particularly at least 90% of the distance back/recovery to the first position), which may further include to the first position (i.e. the same position before deformation or 100% distance back/recovery).

As shown in FIG. 44, the tube 600 may deform (bend) at a deformation distance 630, which is shown as a longitudinal distance within ventilation passageway 250. As shown, the tube 600 may deform at a deformation distance 630 greater than or equal to 0.5 mm, which may include a range of 0.5 mm to 8 mm (including all ranges and increments there between); 0.5 mm to 7 mm (including all ranges and increments there between); 0.5 mm to 6 mm (including all ranges and increments there between); 0.5 mm to 5 mm (including all ranges and increments there between); 0.5 mm to 4 mm (including all ranges and increments there between); 0.5 mm to 3 mm (including all ranges and increments there between); 0.5 mm to 2 mm (including all ranges and increments there between); and 0.5 mm to 1 mm (including all ranges and increments there between).

More particularly, the tube 600 may deform at a deformation distance 630 greater than or equal to 1 mm, which may include a range of 1 mm to 8 mm (including all ranges and increments there between); 1 mm to 7 mm (including all ranges and increments there between); 1 mm to 6 mm (including all ranges and increments there between); 1 mm to 5 mm (including all ranges and increments there between); 1 mm to 4 mm (including all ranges and increments there between); 1 mm to 3 mm (including all ranges and increments there between); and 1 mm to 2 mm (including all ranges and increments there between).

Even more particularly, the tube 600 may vertically deform at a deformation distance 630 greater than or equal to 1.5 mm, which may include a range of 1.5 mm to 8 mm (including all ranges and increments there between); 1.5 mm to 7 mm (including all ranges and increments there between); 1.5 mm to 6 mm (including all ranges and increments there between); 1.5 mm to 5 mm (including all ranges and increments there between); 1.5 mm to 4 mm (including all ranges and increments there between); 1.5 mm to 3 mm (including all ranges and increments there between); and 1.5 mm to 2 mm (including all ranges and increments there between). Other dimensions may include, alone or in any combination, 0.5 mm or more (which may also be set forth as at least 0.5 mm), 1 mm or more; 2 mm or more; 3 mm or more; 4 mm or more, 5 mm or more, 6 mm or more; 7 mm or more; and 8 mm or more; 9 mm or more; 10 mm or more; as well as 10 mm or less (which may also be set forth as at most 10 mm); 9 mm or less, 8 mm or less, 7 mm or less, 6 mm or less, 5 mm or less, 4 mm or less, 3 mm or less, 2 mm or less; 1 mm or less; and 0.5 mm or less.

The deformation distance 630 will depend, to a certain degree, on the lateral distance 612 into the ventilation passageway 250.

Also as shown in FIG. 44, the tube 600 may deform (bend) at a deformation angle 640. As shown, the deformation angle 640 may be measured by the angular change in the orientation of the end (terminal) face 616 of the tube 600. As shown, the end (terminal) face 616 of the tube 600 is shown to be perfectly vertical in FIG. 42, while in FIG. 44, the end (terminal) face 616 of the tube 600 is shown to be perfectly horizontal, thus changing orientation by 90 degrees.

While the deformation angle 640 is shown to be 90 degrees, the deformation angle 640 will depend, to a certain degree, on the lateral distance 612 into the ventilation passageway 250. Thus, the tube 600 may deform at a deformation angle 640 greater than or equal to 5 degrees, which may include a range of 5 degrees to 90 degrees (including all ranges and increments there between); 5 degrees to 85 degrees (including all ranges and increments there between); 5 degrees to 80 degrees (including all ranges and increments there between); 5 degrees to 75 degrees (including all ranges and increments there between); 5 degrees to 70 degrees (including all ranges and increments there between); 5 degrees to 65 degrees (including all ranges and increments there between); 5 degrees to 60 degrees (including all ranges and increments there between); 5 degrees to 55 degrees (including all ranges and increments there between); 5 degrees to 50 degrees (including all ranges and increments there between); 5 degrees to 45 degrees (including all ranges and increments there between); 5 degrees to 40 degrees (including all ranges and increments there between); 5 degrees to 35 degrees (including all ranges and increments there between); 5 degrees to 30 degrees (including all ranges and increments there between); 5 degrees to 25 degrees (including all ranges and increments there between); 5 degrees to 20 degrees (including all ranges and increments there between); 5 degrees to 15 degrees (including all ranges and increments there between); and 5 degrees to 10 degrees (including all ranges and increments there between).

More particularly, the tube 600 may deform at a deformation angle 640 greater than or equal to 10 degrees, which may include a range of 10 degrees to 90 degrees (including all ranges and increments there between); 10 degrees to 85 degrees (including all ranges and increments there between); 10 degrees to 80 degrees (including all ranges and increments there between); 10 degrees to 75 degrees (including all ranges and increments there between); 10 degrees to 70 degrees (including all ranges and increments there between); 10 degrees to 65 degrees (including all ranges and increments there between); 10 degrees to 60 degrees (including all ranges and increments there between); 10 degrees to 55 degrees (including all ranges and increments there between); 10 degrees to 50 degrees (including all ranges and increments there between); 10 degrees to 45 degrees (including all ranges and increments there between); 10 degrees to 40 degrees (including all ranges and increments there between); 10 degrees to 35 degrees (including all ranges and increments there between); 10 degrees to 30 degrees (including all ranges and increments there between); 10 degrees to 25 degrees (including all ranges and increments there between); 10 degrees to 20 degrees (including all ranges and increments there between); and 10 degrees to 15 degrees (including all ranges and increments there between).

More particularly, the tube 600 may deform at a deformation angle 640 greater than or equal to 15 degrees, which may include a range of 15 degrees to 90 degrees (including all ranges and increments there between); 15 degrees to 85 degrees (including all ranges and increments there between); 15 degrees to 80 degrees (including all ranges and increments there between); 15 degrees to 75 degrees (including all ranges and increments there between); 15 degrees to 70 degrees (including all ranges and increments there between); 15 degrees to 65 degrees (including all ranges and increments there between); 15 degrees to 60 degrees (including all ranges and increments there between); 15 degrees to 55 degrees (including all ranges and increments there between); 15 degrees to 50 degrees (including all ranges and increments there between); 15 degrees to 45 degrees (including all ranges and increments there between); 15 degrees to 40 degrees (including all ranges and increments there between); 15 degrees to 35 degrees (including all ranges and increments there between); 15 degrees to 30 degrees (including all ranges and increments there between); 15 degrees to 25 degrees (including all ranges and increments there between); and 15 degrees to 20 degrees (including all ranges and increments there between).

More particularly, the tube 600 may deform at a deformation angle 640 greater than or equal to 20 degrees, which may include a range of 20 degrees to 90 degrees (including all ranges and increments there between); 20 degrees to 85 degrees (including all ranges and increments there between); 20 degrees to 80 degrees (including all ranges and increments there between); 20 degrees to 75 degrees (including all ranges and increments there between); 20 degrees to 70 degrees (including all ranges and increments there between); 20 degrees to 65 degrees (including all ranges and increments there between); 20 degrees to 60 degrees (including all ranges and increments there between); 20 degrees to 55 degrees (including all ranges and increments there between); 20 degrees to 50 degrees (including all ranges and increments there between); 20 degrees to 45 degrees (including all ranges and increments there between); 20 degrees to 40 degrees (including all ranges and increments there between); 20 degrees to 35 degrees (including all ranges and increments there between); 20 degrees to 30 degrees (including all ranges and increments there between); and 20 degrees to 25 degrees (including all ranges and increments there between). Other angles may include, alone or in any combination, 5 degrees or more (which may also be set forth as at least 5 degrees); 10 degrees or more; 15 degrees or more; 20 degrees or more; 25 degrees or more; 30 degrees or more; 35 degrees or more; 40 degrees or more; 45 degrees or more; 50 degrees or more; 55 degrees or more; 60 degrees or more; 65 degrees or more; 70 degrees or more; 75 degrees or more; 80 degrees or more; 85 degrees or more; 90 degrees or more; as well as 90 degrees or less (which may also be set forth as at most 90 degrees); 85 degrees or less; 80 degrees or less; 75 degrees or less; 70 degrees or less; 65 degrees or less; 60 degrees or less; 55 degrees or less; 50 degrees or less; 45 degrees or less; 40 degrees or less; 35 degrees or less; 30 degrees or less; 25 degrees or less; 20 degrees or less; 15 degrees or less; 10 degrees or less; and 5 degrees or less.

It should be understood that the deformation of the tube 600 to provide clearance for the passing of elongated medical instrument 80 is not limited to vertically downward deformation i.e. towards the ventilation tube 120 or the distal end of the ventilation tube apparatus 110, as shown in FIG. 44, away from the transverse plane 614. For example, as shown in FIG. 45, the tube 600 to is deformed vertically upward away from the ventilation tube 120 and towards the proximal end of the ventilation tube apparatus 110 away from the transverse plane 614. Such may be achieved particularly in response to contact or otherwise being acted upon (e.g. by being pushed) by the elongated medical instrument 80 being inserted down the ventilation passageway 250, particularly the center, from the distal end of the ventilation tube apparatus 110 towards the proximal end of the ventilation tube apparatus 110.

In light of the foregoing, it should be understood that the end (terminal) face 616 of the tube 600 moves from extending along the longitudinal axis 150 substantially parallel therewith (e.g., within 20 degrees of being parallel) to being substantially transverse therewith (e.g. within 20 degrees of being perpendicular). As shown, the end (terminal) face 616 of the tube 600 changes orientation by 90 degrees.

Moreover, it should be understood that the deformation of the tube 600 to provide clearance for the passing of elongated medical instrument 80 is not limited to vertical deformation, but that clearance may also be provided by horizontal deformation. For example, as shown in FIG. 46, the tube 600 to is deformed in the transverse plane 614 lateral of the elongated medical instrument 80, particularly by initially inserting the elongated medical instrument 80 into ventilation passageway 250 lateral of the tube 600 without contacting the tube 600 (shown by the phantom (dashed-line) circle), then moving the elongated medical instrument 80 laterally towards the center (shown by the cross-sectional circle) such that the tube 600 deforms (bends), to the left or the right of the elongated medical instrument 80, towards sidewall 252 of the ventilation passage 250, formed by the hub connection fitting body 202. In light of the foregoing, it should be understood that the end (terminal) face 616 of the tube 600 remains substantially parallel with the longitudinal axis 150 (e.g., within 20 degrees of being parallel) before and after being deformed (bent).

In light of the foregoing, it should be understood that, depending on how the elongated medical instrument 80 contacts the tube 600, the tube 600 may be deformed vertically, horizontally, or a combination thereof (i.e. a deformation with both vertical and horizontal directional components). For example, combining two motions of the elongated medical instrument 80 to deform the tube 600, such as motion along the longitudinal axis 150 and motion transverse to the longitudinal axis 150 as described above. It should also be understood that the tube 600 is repeatably deformable and recoverable in response to repeated contacts by the elongated medical instrument 80, and not limited to be deformable and recoverable only in response to one contact by the elongated medical instrument 80.

It should also be understood that the vertically downward deformation distance 630 and deformation angle 640, along with the disclosed numerical values and ranges, discussed with regards to FIG. 44 apply equally to the vertically upward deformation distance 632 and deformation angle 642 of FIG. 45, and the horizontal deformation distance 634 and deformation angle 644 of FIG. 46.

Referring to FIG. 47, there is shown another tube 600 having a plurality of side (transverse) passageways 622 in fluid communication with (longitudinal) tube passageway 604, with each having a side (transverse) sample inlet (opening) 624 thereto to collect exhaled gas(es) of the host/patient.

It should also be understood that the elongated medical instrument 80 being disposed in the ventilation passageway 134, 250 of ventilation tube apparatus 110 may be the result of differing procedures. For example, as already disclosed, the elongated medical instrument 80 may be inserted/slid into the ventilation passageway 134, 250 and extend from the distal end 146 of the ventilation tube120 ("preloaded") before the assembly is inserted into the airway of the patient/host. Thereafter, after the assembly is inserted into the airway of the patient/host and once the ventilation tube apparatus 110 is properly positioned in the airway of the patient/host for ventilation, the elongated medical instrument 80 may be removed from the ventilation passageway 134, 250 by extracting/sliding it out of the ventilation passageway 134, 250 and hence out of the patient/host.

Alternatively, or in addition to, if a ventilation tube apparatus 110 is already properly positioned in the airway of the patient/host, the elongated medical instrument 80 may be inserted/slid into the ventilation passageway 134, 250 and extend from the distal end 146 of the ventilation tube 120. The ventilation tube apparatus 110 may then be removed out of the airway of the patient/host by extracting/sliding the ventilation tube apparatus 110 up and out of the patient/host along the length of the elongated medical instrument 80 while the elongated medical instrument 80 remains in the patient host. Once the (used first) ventilation tube apparatus 110 has been removed from the airway of the patient/host, another (unused/sterile second) ventilation tube apparatus 110 may be inserted into the airway of the patient/host by sliding the ventilation tube apparatus 110 along the length of elongated medical instrument 80 as it progresses into the airway.

Moreover, it should be understood that the elongated medical instrument 80 may not be limited to a ventilation tube guide 82 being inserted into and/or extracted from the ventilation passageway 134, 250 of ventilation tube apparatus 110, requiring movement of the fluid sampling port fitment 500, 598. For example, elongated medical instrument 80 may also comprise a catheter 84 having a lumen 86, shown in FIG. 48, such as a suction catheter. Catheter 84 may be inserted down the ventilation passageway 134, 250 of ventilation tube apparatus 110 to remove secretions such as mucus, and other occlusions, from the ventilation passageway 134, 250 through the lumen 86 and then removed from the ventilation passageway 134, 250.

Referring to FIGS. 49-50, there is shown another embodiment of a hub connection fitting 200 according to the present disclosure, without respirator (ventilator) tube 22; ventilation tube 120 or tube 600 attached thereto. As shown, hub connection fitting 200 includes a lateral (thumb) platform 280 to assist to assist with positioning during intubation. It should be understood that lateral (thumb) platform 280 may be used in combination with other embodiments of the hub connection fitting 200 disclosed herein.

As shown, hub connection fitting body 202 includes distal body portion cylindrical recess 231 to receive the ventilation tube 120 therein. Alternatively, as shown in FIGS. 51 and 52, cylindrical recess 231 may receive hub connection fitting second body 206. Also, as discussed above, one of a plurality of different hub connection fitting second bodies 206 may be permanently (inseparable) fastened to hub connection fitting first body 204, which now may be referred to as hub connection fitting body 202, each with a different diameter of the hub connection fitting second body counter-bore recess 219 to facilitate use of a different diameter ventilation tube 120 (e.g. pediatric, adolescent, adult), respectively, which may have different colors to facilitate quick identification of the size of the ventilation tube 120.

Hub connection fitting first body 204 and a hub connection fitting second body 206, may both be formed of injection molded thermoplastic, such as polypropylene, polyethylene, polyamide or polyacetal. The hub connection fitting first body 204 and the hub connection fitting second body 206 are permanently (inseparable) assembled/fastened together, particularly by welding (e.g. ultrasonic welding) or use of adhesive.

As shown in FIG. 52, hub connection fitting second body 206 is assembled to ventilation tube 120 by being inserted into ventilation passageway 134. In the embodiment shown in FIGS. 51-52, the ventilation tube apparatus 110 is an extraglottic breathing tube apparatus (a/k/a extraglottic airway device (EAD), and more particularly supraglottic breathing tube apparatus (a/k/a supraglottic airway device (SAD)), and the ventilation tube 120 may be referred to as an extraglottic or supraglottic ventilation tube. Other supraglottic airway devices may include the supraglottic airway laryngopharyngeal tube (SALT), which may also be referred to as a supraglottic airway laryngeal tube; the laryngeal mask airway (LMA), which may also be referred to as a laryngeal mask; and the laryngeal tube (LT).

Referring to FIGS. 53-54, there is shown another embodiment of a hub connection fitting 200 according to the present disclosure, also without respirator (ventilator) tube 22; ventilation tube 120 or tube 600 attached thereto. The embodiment shown in FIGS. 53-54 may be particularly suited to work with a laryngeal mask airway (LMA) which incorporates a drain tube in addition to a ventilation tube.

The hub connection fitting second body 206 comprises a secondary passageway 278 lateral of the ventilation passageway 250. Ventilation passageway 250 is configured to be in fluid communication with to a ventilation tube 120, while secondary passageway 278 is configured to provide a passageway for an ancillary device such as a suction/drain device.

While a preferred embodiment(s) of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS

10 medical system
20 respirator apparatus
22 passageway
24 respirator tube
26 sidewall
30 analyzing/monitoring apparatus
50 drug delivery device
60 cuff inflation device
62 inflation cuff
64 inflation cuff inlet/outlet opening aperture
70 syringe
80 elongated medical instrument
82 ventilation tube guide
84 catheter
86 lumen
100 medical device
110 airway management medical device/ventilation tube apparatus
120 ventilation tube
122 outer cylindrical sidewall
124 outer surface
126 inner surface
130 outer diameter
132 inner diameter
134 ventilation passageway
140 proximal end opening
141 cylindrical proximal end region
142 proximal end
143 distal end region
144 distal end opening
146 distal end
150 longitudinal axis
160 secondary passageway
162 semi-circular sidewall
168 cuff inflation fluid line
170 cuff inflation port
172 tube

174 passageway
176 cuff inflation port connector
178 fluid line
180 port
182 tube
184 passageway
186 connector
188*a* first connector
188*b* second connector
190 valve
192 bias member
194 plug
196 stopcock valve
200 hub connection fitting
202 hub connection fitting body
204 hub connection fitting first body
206 hub connection fitting second body
208 hub connection fitting body cavity
210 hub connection fitting first body outer annular ring
211 hub connection fitting first body annular recess
212 hub connection fitting first body inner annular ring
hub connection fitting first body circular shoulder 213
214 hub connection fitting first body counter-bore recess
215 hub connection fitting second body outer annular ring
216 hub connection fitting second body annular recess
217 hub connection fitting second body inner annular ring
218 hub connection fitting second body circular shoulder
219 hub connection fitting second body counter-bore recess
220 proximal body portion
230 distal body portion
231 cylindrical recess
232 inner cylindrical surface
240 intermediate/middle body portion
244 aperture
246 frame
250 ventilation passageway
252 sidewall
254 total cross-sectional area
254*a* inner cross-sectional area region
254*b* outer cross-sectional area region
256 cross-sectional dimension
260 secondary passageway
262 male connector portion
264 counter-bore
270 secondary passageway
274 counter-bore
276 tubular wall
278 secondary passageway
280 lateral (thumb) platform
290 fluid sampling port fitment
300 lighting apparatus
302 light-emitting device
304 light-source module
306 light source
316 slide switch
318 slide switch body
320 slide switch electrical contact
330 power source
332 power source holder
340 electrical (wire) conductor
342 electrical (wire) conductor
344 wall
346 plug receptacle
350 cuff inflation port fitment
370 light-source module cavity/receptacle
374 printed circuit board 378 housing
380 cavity
382 battery holder
384 non-conductive liner
386 pull tab
388 elongated aperture
400 tubular light guide
402 proximal end
404 distal end
406 gap
410 tube
412 tube passageway
420 annular bushing
430 plug
432 plug body
434 blind recess
436 through-hole
500 fluid sampling port fitment
510 T-shaped secondary passageway
512 longitudinal passageway
514 transverse passageway
522 longitudinal tubular wall
524 transverse tubular wall
526 circular flange
528 semi-circular rib
530 cylindrical cavity
532 cylindrical bore
534 cylindrical counter-bore
536 outer end face
540 bias member
550 gasket
560 closure cover
570 rotatable knob
572 rectangular knob body
574 through-hole
576 undercut recess
580 stand-off
590 recess
598 fluid sampling port fitment
600 fluid sampling and/or drug delivery port tube
602 tube annular wall
604 tube passageway
606 outer diameter
608 inner diameter
610 longitudinal axis
612 lateral distance
614 transverse plane
616 end (terminal) face
620 distal end sample inlet (opening)
622 side (transverse) passageway
624 side (transverse) sample inlet (opening)
630 (vertically down) deformation distance
632 (vertically up) deformation distance
634 (horizontal) deformation distance
640 (vertically down) deformation angle
642 (vertically up) deformation angle
644 (horizontal) deformation angle

What is claimed is:

1. A medical device, comprising:
a breathing tube apparatus having a proximal end and a distal end, and further comprising
  a ventilation tube having a proximal end and a distal end, wherein the ventilation tube is configured to be inserted into an airway of a human body;
  a connection fitting body connected to the ventilation tube, wherein the connection fitting body is disposed adjacent the proximal end of the ventilation tube, and wherein the connection fitting body provides the proximal end of the breathing tube apparatus;
a ventilation passageway, wherein the ventilation passageway is disposed in the connection fitting body and disposed in the ventilation tube;
an exhaled gas(es) sampling port, wherein the exhaled gas(es) sampling port is configured to be connected to an exhaled gas(es) sampling device configured to detect a presence of carbon dioxide in an exhaled gas(es) sample;
wherein the exhaled gas(es) sampling port comprises an elastically deformable tube having a tube passageway and at least one sample inlet to the tube passageway, the tube passageway in fluid communication with the ventilation passageway in the connection fitting body via the at least one sample inlet;
wherein the elastically deformable tube extends into the ventilation passageway from the connection fitting body;
wherein the elastically deformable tube is sufficiently elastically deformable to elastically deform when contacted by an elongated medical instrument in the ventilation passageway to provide clearance for the elongated medical instrument to pass by the elastically deformable tube.

2. The medical device of claim 1, further comprising the elongated medical instrument.

3. The medical device of claim 2, wherein the elongated medical instrument is a guide, an introducer, a bougie, a stylet or a catheter.

4. The medical device of claim 1, wherein the ventilation passageway in the connection fitting body has a longitudinal axis;
wherein the elastically deformable tube has a longitudinal axis; and
wherein the longitudinal axis of the elastically deformable tube is substantially transverse to the longitudinal axis of the ventilation passageway in the connection fitting body.

5. The medical device of claim 4, wherein the longitudinal axis of the elastically deformable tube is perpendicular to the longitudinal axis of the ventilation passageway in the connection fitting body.

6. The medical device of claim 1, wherein the elastically deformable tube extends into the ventilation passageway from the connection fitting body at a distance of at least 0.5 mm.

7. The medical device of claim 1, wherein the elastically deformable tube is elastically deformable towards at least one of the distal end of the breathing tube apparatus, the proximal end of the breathing tube apparatus, or a sidewall which forms the ventilation passageway in the connection fitting body.

8. The medical device of claim 1, wherein the elastically deformable tube is moveable from a first position in the ventilation passageway in the connection fitting body to a second position in the ventilation passageway in the connection fitting body by elastic deformation of the elastically deformable tube; and
wherein the elastically deformable tube is moveable from the second position in the ventilation passageway in the connection fitting body towards the first position in the ventilation passageway in the connection fitting body by elastic recovery of the elastically deformable tube.

9. The medical device of claim 1, wherein the elastically deformable tube is elastically deformable in the ventilation passageway in the connection fitting body at a deformation distance; and wherein the deformation distance is greater than or equal to 0.5 mm.

10. The medical device of claim 1, wherein the elastically deformable tube is elastically deformable in the ventilation passageway in the connection fitting body at a deformation angle; and wherein the deformation angle is greater than or equal to 5 degrees.

11. The medical device of claim 1, wherein the ventilation passageway in the connection fitting body has a longitudinal axis;

wherein the ventilation passageway in the connection fitting body has a total cross-sectional area transverse to the longitudinal axis;

wherein the total cross-sectional area has an inner cross-sectional area region and an outer cross-sectional area region;

wherein the outer cross-sectional area region forms an enclosed ring around the inner cross-sectional area region;

wherein the inner cross-sectional area region is in a range of 5% to 95% of the total cross-sectional area;

wherein the at least one sample inlet is disposed in the inner cross-sectional area region.

12. The medical device of claim 1, wherein the ventilation passageway in the connection fitting body has a longitudinal axis;

wherein the ventilation passageway in the connection fitting body has a cross-sectional dimension perpendicular to the longitudinal axis; and wherein the elastically deformable tube and/or the at least one sample inlet extends into the ventilation passageway in the connection fitting body at a distance in a range of 5% to 95% of the cross-sectional dimension of the ventilation passageway in the connection fitting body.

13. The medical device of claim 1, wherein the elastically deformable tube is extruded tubing.

14. The medical device of claim 1, wherein the elastically deformable tube has an outer diameter in a range of 0.50 mm to 3 mm; and/or wherein the tube passageway has a diameter of in a range of 0.25 mm to 2 mm.

15. The medical device of claim 1, wherein the elastically deformable tube is formed of a thermoplastic polymer composition.

16. The medical device of claim 1, wherein the elastically deformable tube has a Shore A durometer hardness, as measured by ASTM D2240-15 (2021), in a range of 40-95 Shore A durometer hardness.

17. The medical device of claim 1, wherein the elastically deformable tube and the connection fitting body are connected as to form a hermetic seal.

18. The medical device of claim 1, wherein the elastically deformable tube and the connection fitting body are at least one of interference fit, bonded or welded together.

19. The medical device of claim 1, wherein the elastically deformable tube has a circular, annular wall which surrounds the tube passageway; and wherein the circular, annular wall of the elastically deformable tube extends through a bore in the connection fitting body.

20. The medical device of claim 1, wherein the breathing tube apparatus is an endotracheal breathing tube apparatus, an extraglottic breathing tube apparatus or a supraglottic breathing tube apparatus.

21. The medical device of claim 1, wherein the elastically deformable tube extends into the ventilation passageway from the connection fitting body at a distance of at least 1 mm.

22. The medical device of claim 1, wherein the elastically deformable tube extends into the ventilation passageway from the connection fitting body at a distance of at least 2 mm.

23. The medical device of claim 1, wherein the elastically deformable tube extends into the ventilation passageway from the connection fitting body at a distance in a range of 0.5 mm to 8 mm.

24. A method, comprising:

obtaining a breathing tube apparatus having a proximal end and a distal end, and further comprising a ventilation tube having a proximal end and a distal end, wherein the ventilation tube is configured to be inserted into an airway of a human body;

a connection fitting body connected to the ventilation tube, wherein the connection fitting body is disposed adjacent the proximal end of the ventilation tube, and wherein the connection fitting body provides the proximal end of the breathing tube apparatus;

a ventilation passageway, wherein the ventilation passageway is disposed in the connection fitting body and disposed in the ventilation tube;

an exhaled gas(es) sampling port, wherein the exhaled gas(es) sampling port is configured to be connected to an exhaled gas(es) sampling device configured to detect a presence of carbon dioxide in an exhaled gas(es) sample;

wherein the exhaled gas(es) sampling port comprises an elastically deformable tube having a tube passageway and at least one sample inlet to the tube passageway, the tube passageway in fluid communication with the ventilation passageway in the connection fitting body via the at least one sample inlet;

wherein the elastically deformable tube extends into the ventilation passageway from the connection fitting body;

inserting an elongated medical instrument into the ventilation passageway in the connection fitting body;

contacting the elastically deformable tube with the elongated medical instrument; and moving the elastically deformable tube with the elongated medical instrument when the elongated medical instrument is disposed in the ventilation passageway of the connection fitting body.

25. The method of claim 24, wherein, during moving of the elastically deformable tube with the elongated medical instrument, the elastically deformable tube moves from a first position to a second position; and wherein, as the elastically deformable tube moves from the first position to the second position, the elastically deformable tube undergoes elastic deformation.

26. The method of claim 25, further comprising:

moving the elastically deformable tube from the second position towards the first position.

27. The method of claim 26, wherein, as the elastically deformable tube moves from the second position towards the first position, the elastically deformable tube undergoes elastic recovery.

28. The method of claim 26, wherein moving the elastically deformable tube from the second position towards the first position occurs during and/or after withdrawing the elongated medical instrument from the breathing tube apparatus.

29. The method of claim 26, wherein moving the elastically deformable tube from the second position towards the first position occurs upon and/or after removing the elongated medical instrument from contact with the elastically deformable tube.

30. The method of claim 24, wherein, as the elastically deformable tube moves, the elastically deformable tube moves laterally in the ventilation passageway.

31. The method of claim 24, wherein, as the elastically deformable tube moves, the elastically deformable tube moves distally in the ventilation passageway.

32. The method of claim 24, wherein, as the elastically deformable tube moves, the elastically deformable tube moves proximally in the ventilation passageway.

33. The method of claim 24, further comprising:
moving the elastically deformable tube a distance greater than or equal to 0.5 mm.

34. The method of claim 24, further comprising:
moving the elastically deformable tube a distance greater than or equal to 1 mm.

35. The method of claim 24, further comprising:
moving the elastically deformable tube a distance greater than or equal to 2 mm.

36. The method of claim 24, further comprising:
moving the elastically deformable tube a distance in a range of 0.5 mm to 8 mm.

37. The method of claim 24, wherein the elastically deformable tube extends into the ventilation passageway from the connection fitting body at a distance of at least 0.5 mm.

38. The method of claim 24, wherein the elastically deformable tube extends into the ventilation passageway from the connection fitting body at a distance of at least 1 mm.

39. The method of claim 24, wherein the elastically deformable tube extends into the ventilation passageway from the connection fitting body at a distance of at least 2 mm.

40. The method of claim 24, wherein the elastically deformable tube extends into the ventilation passageway from the connection fitting body at a distance in a range of 0.5 mm to 8 mm.

41. The method of claim 24, wherein the elongated medical instrument is a guide, an introducer, a bougie, a stylet or a catheter.

* * * * *